United States Patent
Flood et al.

(10) Patent No.: US 10,077,233 B2
(45) Date of Patent: *Sep. 18, 2018

(54) POLY-CYANOSTILBENE MACROCYCLES

(71) Applicant: Indiana University Research and Technology Corporation, Indianapolis, IN (US)

(72) Inventors: Amar H. Flood, Bloomington, IN (US); Semin Lee, Bloomington, IN (US); Kevin McDonald, Oak Park, IL (US)

(73) Assignee: INDIANA UNIVERSITY RESEARCH AND TECHNOLOGY CORPORATION, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/645,721

(22) Filed: Jul. 10, 2017

(65) Prior Publication Data
US 2017/0313652 A1    Nov. 2, 2017

Related U.S. Application Data

(63) Continuation-in-part of application No. 14/767,570, filed as application No. PCT/US2014/016332 on Feb. 13, 2014, now Pat. No. 9,701,621.

(60) Provisional application No. 61/764,238, filed on Feb. 13, 2013.

(51) Int. Cl.
| | | |
|---|---|---|
| *C07D 213/57* | (2006.01) | |
| *C07C 255/47* | (2006.01) | |
| *C07F 7/18* | (2006.01) | |
| *C07D 249/06* | (2006.01) | |

(52) U.S. Cl.
CPC .......... *C07C 255/47* (2013.01); *C07D 213/57* (2013.01); *C07D 249/06* (2013.01); *C07F 7/1852* (2013.01); *C07C 2603/90* (2017.05)

(58) Field of Classification Search
CPC .. C07D 213/57; C07D 249/04; C07D 249/06; C07F 7/08; C07F 7/18; C07F 7/1852; C07C 255/47; C07C 2603/90
See application file for complete search history.

(56) References Cited

U.S. PATENT DOCUMENTS

| | | |
|---|---|---|
| 3,781,279 A | 12/1973 | Crounse et al. |
| 5,750,577 A | 5/1998 | Georghiou |
| 6,534,135 B1 | 3/2003 | Cherkaoui |
| 7,592,475 B2 | 9/2009 | Park et al. |
| 7,655,961 B2 | 2/2010 | Marrocco, III et al. |
| 8,101,804 B2 | 1/2012 | Schouteeten et al. |
| 9,701,621 B2* | 7/2017 | Flood .................. C07C 255/47 |
| 2007/0125712 A1 | 6/2007 | Little et al. |
| 2007/0149799 A1 | 6/2007 | Park et al. |
| 2010/0301310 A1 | 12/2010 | Noguchi et al. |

OTHER PUBLICATIONS

Alcalde, E., Ayala, C., Dinarès, I. & Mesquida, N. Polynucleating open-chain systems with imidazole and proton-ionizable 1,2,4-triazole structural motifs. J. Org. Chem. 66, 2291-2295 (2001).
An, B.-K., Kwon, S.-K., Jung, S.-D. & Park, S. Y. Enhanced emission and its switching in fluorescent organic nanoparticles. J. Am. Chem. Soc. 124, 14410-14415 (2002).
An, BK et al., pi-Conjugated Cyanostilbene Derivatives: A Unique Self-Assembly Motif for Molecular Nanostructures with Enhanced Emission and Transport, Accounts of Chem. Res. 45(4):544-554 (2011).
Ashton, P. R. et al. Self-assembling [2]- and [3]rotaxanes from secondary dialkylammonium salts and crown ethers. Chem. Eur. J. 2,729-736 (1996).
Bandera, D., Baldridge, K. K., Linden, A., Dorta, R. & Siegel, J. S. Stereoselective coordination of C5-symmetric corannulene derivatives with an enantiomerically pure [Rhl(nbd*)] metal complex. Angew. Chem. Int. Ed. 50,865-867 (2011).
Bao, R et al., Synthesis and characterization of six-arm star-shaped liquid crystalline cyclotriphosphazenes, Chinese Chemical Letters, 21:682-685 (2010).
Brak, K. & Jacobsen, E. N. Asymmetric ion-pairing catalysis. Angew. Chem. Int. Ed. 52,534-561 (2013).
Brouwer, A. M. et al. Photoinduction of fast, reversible translational motion in a hydrogen-bonded molecular shuttle. Science 291,2124-2128 (2001).

(Continued)

*Primary Examiner* — D Margaret M Seaman
(74) *Attorney, Agent, or Firm* — Klintworth & Rozenblat IP LLP

(57) ABSTRACT

The present disclosure concerns synthesis and anion binding features of poly-cyanostilbene macrocycles of Formula (I):

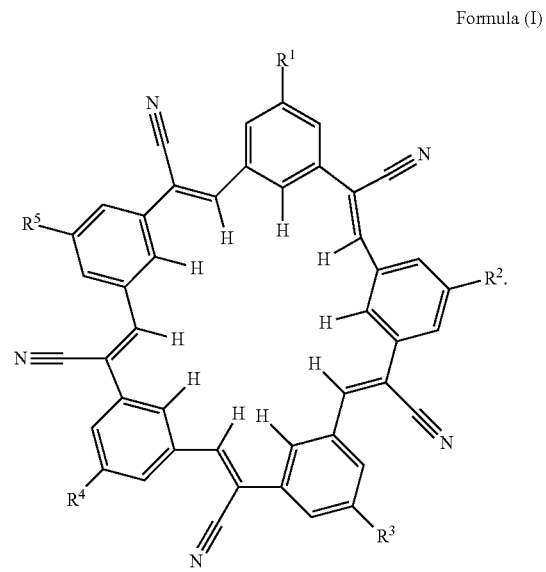

Formula (I)

8 Claims, 28 Drawing Sheets

(56) References Cited

OTHER PUBLICATIONS

Bryantsev, V. S. & Hay, B. P. Are C—H groups significant hydrogen bonding sites in anion receptors? Benzene aomplexes with Cl—, NO3—, and ClO4—. J. Am. Chem. Soc. 127,8282-8283 (2005).

Busch, D. H. The significance of complexes of macrocyclic ligands and their synthesis by ligand reactions. Rec. Chem. Progr. 25,107-126 (1964).

Craig, M. R., Claridge, T. D. W., Hutchings, M. G. & Anderson, H. L. Synthesis of a cyclodextrin azo dye [3]rotaxane as a single isomer. Chem. Commun. 1537-1538 (1999).

Cram, D. J. & Sogah, G. D. Y. Chiral crown complexes catalyse Michael addition reactions to give adducts in high optical yields. J. Chem. Soc. Chem. Commun. 625-628 (1981).

Du, Z. et al. BOP-mediated one-pot synthesis of C5-symmetric macrocyclic pyridone pentamers. Chem. Commun. 47, 12488-12490 (2011).

Etacheri, V., Marom, R., Elazari, R., Salitra, G. & Aurbach, D. Challenges in the development of advanced Li-ion batteries: a review. Energy Environ. Sci. 4,3243-3262 (2011).

Ghosh, P., Mermagen, O. & Schalley, C. A. Novel template effect for the preparation of [2]rotaxanes with functionalized centre pieces. Chem. Commun. 2628-2629 (2002).

Greer, M. A., Goodman, G., Pleus, R. C. & Greer, S. E. Health effects assessment for environmental perchlorate contamination: The dose response for inhibition of thyroidal radioiodine uptake in humans. Environ. Health Persp. 110, 927-937 (2002).

Guieu, S., Crane, A. K. & MacLachlan, M. J. Campestarenes: Novel shape-persistent Schiff base macrocycles. Chem. Commun. 47, 1169-1171 (2011).

Hanson, J. C. & Nordman, C. E. The crystal and molecular structure of corannulene, C20H10. Acta Cryst. B 32, 1147-1153 (1976).

Hayashida, O., Shivanyuk, A. & Rebek Jr., J. Molecular encapsulation of anions in a neutral receptor. Angew. Chem. Int. Ed. 41, 3423-3426 (2002).

Höger, S. Shape-persistent phenylene-acetylene macrocycles: Large rings—low yield? Angew. Chem. Int. Ed. 44, 3806-3808 (2005).

Hristova, Y. R., Smulders, M. M. J., Clegg, J. K., Breiner, B. & Nitschke, J. R. Selective anion binding by a "chameleon" capsule with a dynamically reconfigurable exterior. Chem. Sci. 2, 638-641 (2011).

Hua, Y. & Flood, A. H. Click chemistry generates privileged CH hydrogen-bonding triazoles: The latest addition to anion supramolecular chemistry. Chem. Soc. Rev. 39, 1262-1271 (2010).

Hübner, G. M., Gläser, J., Seel, C. & Vögtle, F. High-yielding rotaxane synthesis with an anion template. Angew. Chem. Int. Ed. 38, 383-386 (1999).

International Search Report for PCT/US2014/016332, dated May 21, 2014, 14 pages.

Katayev, E. A., Ustynyuk, Y. A. & Sessler, J. L. Receptors for tetrahedral oxyanions. Coord. Chem. Rev. 250, 3004-3037 (2006).

Kay, E. R., Leigh, D. A. & Zerbetto, F. Synthetic molecular motors and mechanical machines. Angew. Chem. Int. Ed. 46, 72-191 (2007).

Keaveney, C. M. & Leigh, D. A. Shuttling through anion recognition. Angew. Chem. Int. Ed. 43, 1222-1224 (2004).

Lee, C. F. et al. Hybrid organic-inorganic rotaxanes and molecular shuttles. Nature 458, 314-318 (2009).

Li, Y. & Flood, A. H. Pure C—H hydrogen bonding to chloride ions: A preorganized and rigid macrocyclic receptor. Angew. Chem. Int. Ed. 47, 2649-2652 (2008).

Li, Y., Pink, M., Karty, J. A. & Flood, A. H. Dipole-promoted and size-dependent cooperativity between pyridyl-containing triazolophanes and halides leads to persistent sandwich complexes with iodide. J. Am. Chem. Soc. 130, 17293-17295 (2008).

Ma, D. et al. Acyclic cucurbit[n]uril molecular containers enhance the solubility and bioactivity of poorly soluble pharmaceuticals. Nat. Chem. 4, 503-510 (2012).

Ogoshi, T., Kanai, S., Fujinami, S., Yamagishi, T.-a. & Nakamoto, Y. para-Bridged symmetrical pillar[5]arenes: Their Lewis acid catalyzed synthesis and host-guest property. J. Am. Chem. Soc. 130, 5022-5023 (2008).

Pedersen, C. J. Cyclic polyethers and their complexes with metal salts. J. Am. Chem. Soc. 89, 2495-2496 (1967).

Qin, B. et al. Crystallographic evidence of an unusual, pentagon-shaped folding pattern in a circular aromatic pentamer. Org. Lett. 10, 5127-5130 (2008).

Qin, B. et al. Persistently folded circular aromatic amide pentamers containing modularly tunable cation-binding cavities with high ion selectivity. J. Am. Chem. Soc. 132, 9564-9566 (2010).

Ren, C. et al. Crystallographic realization of the mathematically predicted densest all-pentagon packing lattice by C5-symmetric "sticky" fluoropentamers. Angew. Chem. Int. Ed. 50, 10612-10615 (2011).

Ren, C., Xu, S., Xu, J., Chen, H. & Zeng, H. Planar macrocyclic fluoropentamers as supramolecular organogelators. Org. Lett. 13,3840-3843 (2011).

Roobottom, H. K., Jenkins, H. D. B., Passmore, J. & Glasser, L. Thermochemical radii of complex ions. J. Chem. Educ. 76,1570-1573 (1999).

Rosenthal, M. R. The myth of the non-coordinating anion. J. Chem. Educ. 50,331-335 (1973).

Sessler, J. L. et al. A pyrrolyl-based triazolophane: A macrocyclic receptor with CH and NH donor groups that exhibits a preference for pyrophosphate anions. J. Am. Chem. Soc. 132,14058-14060 (2010).

Shen, Q.; Zhang, J.; Zhang, S.; Hao, Y.; Zhang, W.; Zhang, W.; Chen, G.; Zhang, Z.; Zhu, X. Facile one-pot/one-step technique for preparation of side-chain functionalized polymers: Combination of SET-RAFT polymerization of azide vinyl monomer and click chemistry. J. Polym. Sci., Part A: Polym. Chem. 50:1120-1126 (2012).

Shen, T et al., Naturals stilbene: an overview, Natural Product Reports, 916-935 (Jun. 2009).

Stoddart, J. F. The chemistry of the mechanical bond. Chem. Soc. Rev. 38,1802-1820 (2009).

Szumna, A. Inherently chiral concave molecules—from synthesis to applications. Chem. Soc. Rev. 39,4274-4285 (2010).

Tahara, K., Balandina, T., Furukawa, S., De Feyter, S. & Tobe, Y. Molecular pentagonal tiling: Self-assemblies of pentagonal-shaped macrocycles at liquid/solid interfaces. CrystEngComm. 13,5551-5558 (2011).

Talotta, C., Gaeta, C., Pierro, T. & Neri, P. Sequence stereoisomerism in calixarene-based pseudo[3]rotaxanes. Org. Lett. 13,2098-2101 (2011).

Tinant, B. et al. Structural study of stilbenes. 2. Crystal-structure redetermination of trans 4'-dimethylamino-4-nitro-☐-cyanostilbene C17H15N3O2. Bull. Soc. Chim. Belg. 92,403-404 (1983).

Valeur B. & Leray, I. Design principles of fluorescent molecular sensors for cation recognition. Coord. Chem. Rev. 205, 3-40 (2000).

Vander Griend, D. A., Bediako, D. K., DeVries, M. J., DeJong, N. A. & Heeringa, L. P. Detailed spectroscopic, thermodynamic, and kinetic characterization of nickel(II) complexes with 2,2'-bipyridine and 1,10-phenanthroline attained via equilibrium-restricted factor analysis. Inorg. Chem. 47, 656-662 (2007).

Wisner, J. A., Beer, P. D., Drew, M. G. B. & Sambrook, M. R. Anion-templated rotaxane formation. J. Am. Chem. Soc. 124, 12469-12476 (2002).

Yu, G. & Heeger, A. J. Charge separation and photovoltaic conversion in polymer composites with internal donor-acceptor heterojunctions. J. Appl. Phys. 78, 4510-4515 (1995).

Yuan, L. H. et al. Highly efficient, one-step macrocyclizations assisted by the folding and preorganization of precursor oligomers. J. Am. Chem. Soc. 126, 11120-11121 (2004).

Zhang, J., Pesak, D. J., Ludwick, J. L. & Moore, J. S. Geometrically-controlled and site-specifically-functionalized phenylacetylene macrocycles. J. Am. Chem. Soc. 116, 4227-4239 (1994).

Zhang, W. & Moore, J. S. Arylene ethynylene macrocycles prepared by precipitation-driven alkyne metathesis. J. Am. Chem. Soc., 126, 12796 (2004).

(56) References Cited

OTHER PUBLICATIONS

Maeda et al., Synthesis and Photochemical Properties of Stilbenophanes Tethered by Silyl Chains, Control of (2π + 2π) Photocycloaddition, Cis-Trans Photoisomerization, and Photocyclization, J. Org. Chem. 70:9693-9701 (2005).

Benson, Christopher, R., et al, "Extreme Stabilization and Redox Switching of Organic Anions and Radical Anions by Large-Cavity, CH Hydrogen-Bonding Cyanostar Macrocycles", Journal of the American Chemical Society 2016 138 (45), pp. 15057-15065. DOI: 10.1021/jacs.6b09459.

* cited by examiner

+

(i)

(ii)

MPTz

POLY-CYANOSTILBENE MACROCYCLES

CROSS-REFERENCE TO RELATED APPLICATIONS

The present application is a continuation-in-part of U.S. patent application Ser. No. 14/767,570, filed Aug. 12, 2015, now issued as U.S. Pat. No. 9,701,621, which is the National Stage of International Application No. PCT/US2014/016332, filed Feb. 13, 2014, which claims the benefit of U.S. Provisional Patent Application No. 61/764,238, filed Feb. 13, 2013, and entitled "POLY-CYANOSTILBENE MACROCYCLES." The contents of the U.S. Provisional patent application and the U.S. patent application are hereby incorporated by reference in their entirety.

STATEMENT OF GOVERNMENT INTEREST

This invention was made with government support under CHE0844441 and CHE1412401 awarded by the National Science Foundation. The government has certain rights in the invention.

FIELD OF INVENTION

This invention pertains to the synthesis and use of poly-cyanostilbene macrocycles for selective anion binding.

BACKGROUND

Ever since Pedersen's discovery that easy-to-make crown ethers provide size-selective binding to alkali cations, macrocycles have proven to be fundamental to the foundation of molecular recognition and have seeded potential applications across chemistry and biology, such as phase transfer catalysis and drug delivery. Building on their propensity for self-assembly, macrocycles also serve as precursors to interlocked molecules where host-guest complexes are captured covalently as rotaxanes and catenanes using mechanical bonding. While this diversity of usage marks macrocycles as singularly attractive synthetic and functional targets, their plentiful numbers and varieties demands that any new macrocycle deliver a distinctive cross section of supramolecular properties.

Moreover, with macrocycles serving as central precursors, the yield and the scale of their production are critical to their early assessment. Work by Busch demonstrated the power of pre-organization, whether using templates or favorable intramolecular contacts, to realize high-yielding macrocyclizations. While these principles promise macrocycles in one-pot reactions from simple building blocks that can be conducted on large scales, realization of this potential is rare. Rather, multistep reaction schemes conducted at modest scales are typical. Nevertheless, a number of macrocycles are intrinsically easy to prepare, e.g., symmetric tetraphenylporphyrins and recently Ogoshi's pillar[5]arenes, with some that can be produced on gram scales, e.g., Gong's oligoamides. Others achieve this outcome through deliberate investigation, such as Moore's production of shape-persistent arylene ethynylene macrocycles using reversible alkyne metathesis under thermodynamic control.

There are only a few semi-planar, $C_5$-symmetric macrocycles. Pentameric phenylene ethynylenes have been examined for surface self-assembly at the liquid-solid interface. Zeng's aryl-amide pentamers can be optimized for one-pot preparations, and can be tailored for selective cation binding, dense crystal packing, and gelation. MacLachlan's aryl-imine campestarene, which can be prepared in high yields in one pot, shows keto-enol tautomerism within the H-bonded imines.

BRIEF SUMMARY OF THE INVENTION

In a first aspect, a poly-cyanostilbene macrocycle of Formula (I) is disclosed:

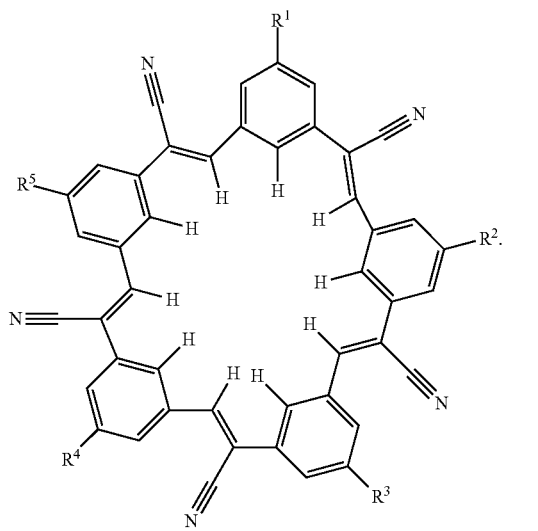

Formula (I)

The $R^1$, $R^2$, $R^3$, $R^4$, and $R^5$ are each independently selected from the group consisting of alkenyl, alkyl, alkoxy, alkyl-NH-alkyl, aryl, cycloalkyl, heteroaryl, heterocycle, haloalkyl, hydrogen, iodo, —$OR^6$, —$N(R^7R_8)$, —$CO_2R^9$, —C(O)—$N(R^{10}R^{11})$, wherein $R^6$, $R^7$, $R^8$, $R^9$, $R^{10}$, and $R^{11}$ are each independently selected from the group consisting of alkenyl, alkyl, alkoxy, alkyl-NH-alkyl, aryl, arylalkyl, cycloalkyl, heteroaryl, heterocycle, haloalkyl, and hydrogen.

In a second aspect, a poly-cyanostilbene macrocycle of Formula (IV) is disclosed:

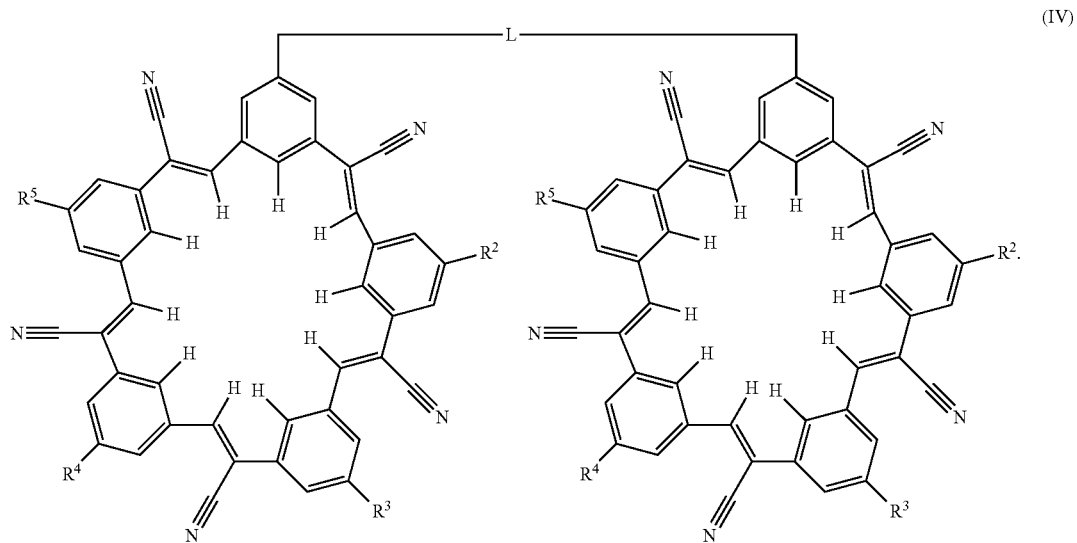

(IV)

The $R^2$, $R^3$, $R^4$, and $R^5$ are each independently selected from the group consisting of alkenyl, alkyl, alkoxy, alkyl-NH-alkyl, aryl, cycloalkyl, heteroaryl, heterocycle, haloalkyl, hydrogen, iodo, —$OR^6$, —$N(R^7R^8)$, —$CO_2R^9$, —$C(O)$—$N(R^{10}R^{11})$, wherein $R^6$, $R^7$, $R^8$, $R^9$, $R^{10}$, and $R^{11}$ are each independently selected from the group consisting of alkenyl, alkyl, alkoxy, alkyl-NH-alkyl, aryl, arylalkyl, cycloalkyl, heteroaryl, heterocycle, haloalkyl, and hydrogen, and L comprising an alkyl moiety ranging from $C_{1-30}$, said alkyl moiety comprising a saturated or unsaturated alkyl moiety, and optionally comprises substituents.

In a third aspect, a complex that includes (a) an anion and (b) a poly-cyanostilbene macrocycle of Formula (I) is disclosed:

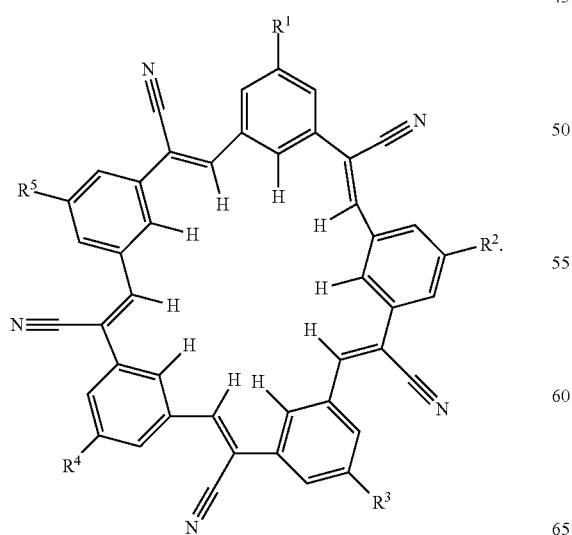

Formula (I)

The $R^1$, $R^2$, $R^3$, $R^4$, and $R^5$ are each independently selected from the group consisting of alkenyl, alkyl, alkoxy, alkyl-NH-alkyl, aryl, cycloalkyl, heteroaryl, heterocycle, haloalkyl, hydrogen, iodo, —$OR^6$, —$N(R^7R^8)$, —$CO_2R^9$, —$C(O)$—$N(R^{10}R^{11})$, wherein $R^6$, $R^7$, $R^8$, $R^9$, $R^{10}$, and $R^{11}$ are each independently selected from the group consisting of alkenyl, alkyl, alkoxy, alkyl-NH-alkyl, aryl, arylalkyl, cycloalkyl, heteroaryl, heterocycle, haloalkyl, and hydrogen.

In a fourth aspect, a complex that includes (a) an anion and (b) a poly-cyanostilbene macrocycle of Formula (IV) is disclosed:

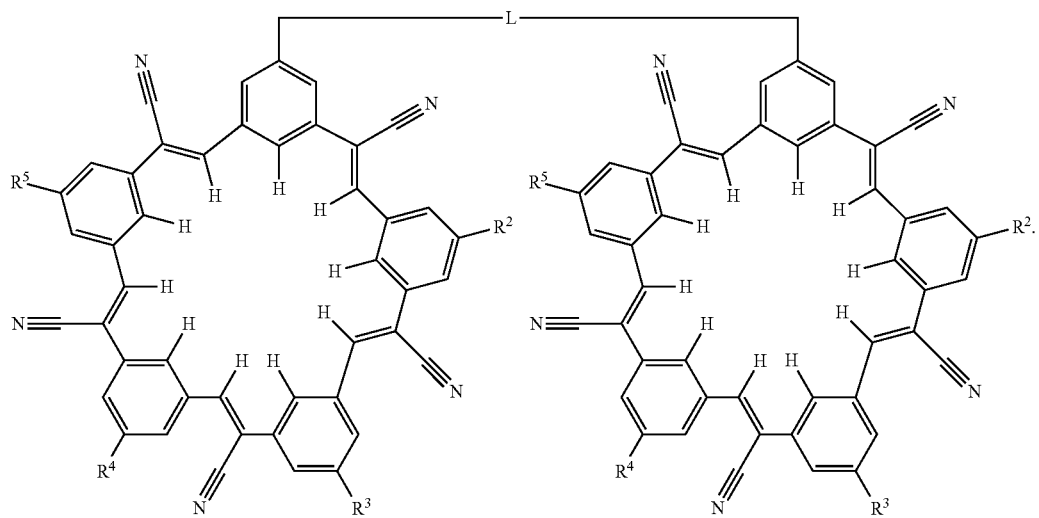

(IV)

The $R^2$, $R^3$, $R^4$, and $R^5$ are each independently selected from the group consisting of alkenyl, alkyl, alkoxy, alkyl-NH-alkyl, aryl, cycloalkyl, heteroaryl, heterocycle, haloalkyl, hydrogen, iodo, —$OR^6$, —$N(R^7R^8)$, —$CO_2R^9$, —$C(O)$—$N(R^{10}R^{11})$, wherein $R^6$, $R^7$, $R^8$, $R^9$, $R^{10}$, and $R^{11}$ are each independently selected from the group consisting of alkenyl, alkyl, alkoxy, alkyl-NH-alkyl, aryl, arylalkyl, cycloalkyl, heteroaryl, heterocycle, haloalkyl, and hydrogen, and L comprising an alkyl moiety ranging from $C_{1-30}$, said alkyl moiety comprising a saturated or unsaturated alkyl moiety, and optionally comprises substituents.

In a fifth aspect, a method of removing an anion from a solution containing the anion is disclosed. The method includes three steps. The first step includes contacting the solution with a poly-cyanostilbene macrocycle. The second step includes forming a complex, said complex comprising the anion and the poly-cyanostilbene macrocycle. The third step includes removing the complex from the solution.

DETAILED DESCRIPTION

Definitions

Figure 1A:
FIG. 1A illustrates an exemplary synthesis of "Cyanostar" (CS), a poly-cyanostilbene macrocycle with five-fold symmetry, using Knoevenagel condensation and the calculated (B3LYP/6-31G*) dipole moment and electrostatic potential.
Figure 1A:
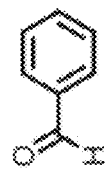
Figure 1A:
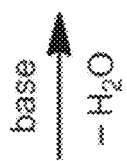
Figure 1A:
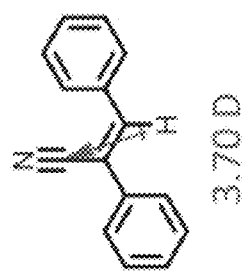
Figure 1A:
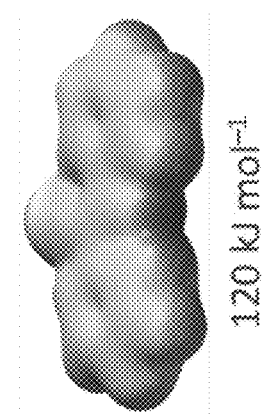

When introducing elements of aspects of the disclosure or particular embodiments, the articles "a," "an," "the," and "said" are intended to mean that there are one or more of the elements. The terms "comprising," "including," and "having" are intended to be inclusive and mean that there may be additional elements other than the listed elements. The term "or" means any one member of a particular list and also includes any combination of members of that list, unless otherwise specified.

As intended herein, the terms "substantially," "approximately," and "about" and similar terms are intended to have a broad meaning in harmony with the common and accepted usage in the art to which the subject matter of this disclosure pertains. It should be understood by those of skill in the art who review this disclosure that these terms are intended to allow a description of certain features described and claimed without restricting the scope of these features to precise numerical ranges provided. Accordingly, these terms should be interpreted as indicating that insubstantial or inconsequential modifications or alterations of the subject matter described and claimed are considered to be within the scope of the invention as recited in the appended claims.

The compounds herein described may exhibit chirality and may be isolated in optically active or racemic forms. Methods for preparing optically active forms include, for instance, resolution of racemic forms or synthesis from optically active starting materials. Many geometric isomers of olefins, C=N double bonds, and the like can also be present in the compounds described herein, and all such stable isomers are contemplated in the present invention. All chiral, diastereomeric, racemic forms and all geometric isomeric forms of a structure are intended, unless the specific stereochemistry or isomeric form is specifically indicated.

The compounds herein described may exist as salts. The term "salt," refers to salts or zwitterions of the compounds which are water or oil-soluble or dispersible. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide the salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the present compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'- dibenzylethylenediamine, ethylenediamine, ethanolamine, diethanolamine, piperidine, piperazine and the like, are contemplated as being within the scope of the present invention.

The term "substituted," as used herein, means that any one or more hydrogens on the designated atom is replaced with a selection from the indicated group, provided that the designated atom's normal valency is not exceeded, and that the substitution results in a stable compound. When a substituent is oxo (i.e., =O), then 2 hydrogens on the atom are replaced. Oxo substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent, provided that the resulting bond is present in a stable compound.

The term "hydroxy" as used herein, refers to an —OH group. The term "oxo" as used herein, refers to a =O group. The term "oxy" as used herein, refers to a —O— group. The term "sulfonyl" as used herein, refers to a —S(O)$_2$— group. The term "carbonyl" as used herein refers to a —C(O)— group. The term "carboxy" as used herein refers to a —C(O)—OH group. The term "halo" or "halogen," as used herein, refers to —Cl, —Br, —I or —F.

The term "alkenyl" as used herein, refers to a straight or branched chain hydrocarbon group containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, hexyloxy, heptyloxy, octyloxy, nonyloxy, decyloxy, undecyloxy, dodecyloxy, trisdecyloxy, tetradecyloxy, and pentadecyloxy.

The term "alkyl" as used herein, refers to a straight or branched chain hydrocarbon group containing from 1 to 15 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl and n-decyl.

The term "alkyl-NH" as used herein, refers to an alkyl group, as defined herein, appended to the parent molecular moiety through a nitrogen atom.

The term "alkyl-NH-alkyl" as used herein, refers to an alkyl-NH group, as defined herein, appended to the parent molecular moiety through an alkyl group, as defined herein.

The term "aryl" as used herein, means a phenyl group, or a bicyclic or a tricyclic fused ring system. Bicyclic fused ring systems are exemplified by a phenyl group appended to the parent molecular moiety and fused to a monocyclic cycloalkyl group, as defined herein, a phenyl group, a monocyclic heteroaryl group, as defined herein, or a monocyclic heterocycle, as defined herein. Tricyclic fused ring systems are exemplified by an aryl bicyclic fused ring system, as defined herein and fused to a monocyclic cycloalkyl group, as defined herein, a phenyl group, a monocyclic heteroaryl group, as defined herein, or a monocyclic heterocycle, as defined herein. Representative examples of aryl include, but are not limited to, anthracenyl, azulenyl, fluorenyl, indanyl, indenyl, naphthyl, phenyl and tetrahydronaphthyl.

The term "cycloalkyl" as used herein, refers to a monocyclic, bicyclic, or tricyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl and cyclooctyl. Bicyclic fused ring systems are exemplified by a cycloalkyl group appended to the parent molecular moiety, which is fused to an additional cycloalkyl group, as defined herein, a phenyl group, a heteroaryl, as defined herein, or a heterocycle as defined herein. Tricyclic fused ring systems are exemplified by a cycloalkyl bicyclic fused ring system fused to an additional cycloalkyl group, as defined herein, a phenyl group, a heteroaryl, as defined herein, or a heterocycle as defined herein. Bicyclic ring systems are also exemplified by a bridged monocyclic ring system in which two non-adjacent carbon atoms of the monocyclic ring are linked by an alkylene bridge of between one and three additional carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane and bicyclo[4.2.1]nonane. Tricyclic ring systems are also exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo[3.3.1.0$^{3,7}$]nonane and tricyclo[3.3.1.1$^{3,7}$]decane (adamantane).

The term "haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl and 2-chloro-3-fluoropentyl.

The term "heteroaryl," as used herein, refers to an aromatic monocyclic ring or an aromatic bicyclic ring system. The aromatic monocyclic rings are five or six membered rings containing at least one heteroatom independently selected from the group consisting of N, O and S. The five membered aromatic monocyclic rings have two double bonds and the six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. Representative examples of heteroaryl include, but are not limited to, benzimidazolyl, benzofuranyl, benzothiazolyl, benzothienyl, benzoxazolyl, furyl, imidazolyl, indazolyl, indolyl, indolizinyl, isobenzofuranyl, isoindolyl, isoxazolyl, isoquinolinyl, isothiazolyl, naphthyridinyl, oxadiazolyl, oxazolyl, phthalazinyl, pyridinyl, pyridazinyl, pyridyl, pyrimidinyl, pyrazinyl, pyrazolyl, pyrrolyl, quinolinyl, quinolizinyl, quinoxalinyl, quinazolinyl, tetrazolyl, thiadiazolyl, thiazolyl, thienyl, triazolyl and triazinyl.

The term "heterocycle" as used herein, refers to a non-aromatic monocyclic ring or a non-aromatic bicyclic ring. The non-aromatic monocyclic ring is a three, four, five, six, seven, or eight membered ring containing at least one heteroatom, independently selected from the group consisting of N, O and S. Representative examples of monocyclic ring systems include, but are not limited to, azetidinyl, aziridinyl, diazepinyl, dithianyl, imidazolinyl, imidazolidinyl, isothiazolinyl, isoxazolinyl, isoxazolidinyl, morpholinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydro-2H-pyranyl, tetrahydro-2H-pyran-2-yl, tetrahydro-2H-pyran-4-yl, tetrahydrothienyl, thiazolinyl, thiazolidinyl, thiomorpholinyl, 1,1-dioxidothiomorpholinyl (thiomorpholine sulfone) and thiopyranyl. The bicyclic heterocycles are exemplified by a monocyclic heterocycle appended to the parent molecular moiety and fused to a monocyclic cycloalkyl group, as defined herein, a monocyclic aryl group, a monocyclic heteroaryl group, as defined herein, or a monocyclic heterocycle, as defined herein. Bicyclic ring systems are also exemplified by a bridged monocyclic ring system in which two non-adjacent atoms of the monocyclic ring are linked by a bridge of between one and three atoms selected from the group consisting of carbon, nitrogen and oxygen. Representative examples of bicyclic ring systems include but are not limited to, for example, benzopyranyl, benzothiopyranyl, benzodioxinyl, 1,3-benzodioxolyl, cinnolinyl, 1,5-diazocanyl, 3,9-diaza-bicyclo[4.2.1]non-9-yl, 3,7-diazabicyclo[3.3.I]nonane, octahydro-pyrrolo[3,4-c]pyrrole, indolinyl, isoindolinyl, 2,3,4,5-tetrahydro-1H-benzo[c]azepine, 2,3,4,5-tetrahydro-1H-benzo[b]azepine, 2,3,4,5-tetrahydro-1H-benzo[d]azepine, tetrahydroisoquinolinyl and tetrahydroquinolinyl.

The chemical structures described herein are named according to IUPAC nomenclature rules and include art-accepted common names and abbreviations where appropriate. The IUPAC nomenclature can be derived with chemical structure drawing software programs, such as ChemDraw® (PerkinElmer, Inc.), ChemDoodle® (iChemLabs, LLC) and Marvin (ChemAxon Ltd.). The chemical structure controls in the disclosure to the extent that a compound name is misnamed or otherwise conflicts with the chemical structure disclosed herein.

Poly-Cyanostilbene Macrocycles

The present disclosure is based on the discovery of a new type of $C_5$-symmetric macrocycle based on cyanostilbene, as exemplified in FIG. 1. The discovery of a high yielding, multi-gram scale and one-pot synthesis for the macrocycles both stimulated and enabled a rapid evaluation of its properties. The poly-cyanostilbene macrocycles offer properties that are complementary to those of traditional macrocycles and that are believed to stem from their cyanostilbene repeating unit. Without wishing to be bound to any particular theory, electropositive cyanostilbene-based CH groups are believed to form H-bonds with anions inside the macrocycle cavities. The receptor's size shows a bias towards large and traditionally weakly-coordinating anions and its shallow-bowl shape and electron-deficient cyanostilbene constituents help create a π-surface that favors 2:1 sandwich complexes in mixed apolar-protic solvents.

Selection of the cyanostilbene motif was motivated initially by an interest in generalizing the concept of useful CH H-bonds of which 1,2,3-triazoles, with their activated CH donors, are exemplary. We asked: Are triazoles uniquely privileged or are there other CH donors that are just as useful? To address this question, it was recognized that any viable polarized CH bond would also need to mimic the ease with which 1,2,3-triazoles can be incorporated into pre-organized receptors; just as triazoles were employed in the preparation of triazolophanes by using click chemistry. Cyanostilbenes (FIG. 1A) emerged as exciting candidates. Beyond their ability to form intermolecular CH . . . N H-bonds in the solid state, it was discovered that they are easy to make using Knoevenagel condensation; a quality highlighted in the efficient example synthesis of poly-cyanostilbene macrocycle "cyanostar" ("CS").

Accordingly, in one aspect, there is provided a poly-cyanostilbene macrocycle of Formula (I):

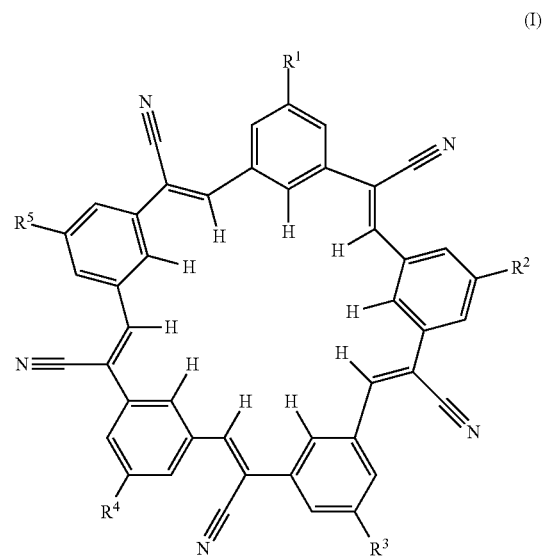

In a compound of Formula (I), $R^1$, $R^2$, $R^3$, $R^4$, and $R^5$ are each independently selected from the group consisting of alkenyl, alkyl, alkoxy, alkyl-NH-alkyl, aryl, cycloalkyl, heteroaryl, heterocycle, haloalkyl, hydrogen, iodo, —$OR^6$, —$N(R^7R^8)$, —$CO_2R^9$, —$C(O)$—$N(R^{10}R^{11})$, wherein $R^6$, $R^7$, $R^8$, $R^9$, $R^{10}$, and $R^{11}$ are each independently selected from the group consisting of alkenyl, alkyl, alkoxy, alkyl-NH-alkyl, aryl, arylalkyl, cycloalkyl, heteroaryl, heterocycle, haloalkyl, and hydrogen.

In some instances, moieties $R^1$, $R^2$, $R^3$, $R^4$, and $R^5$ are all the same R group, as illustrated below in Formula (IR):

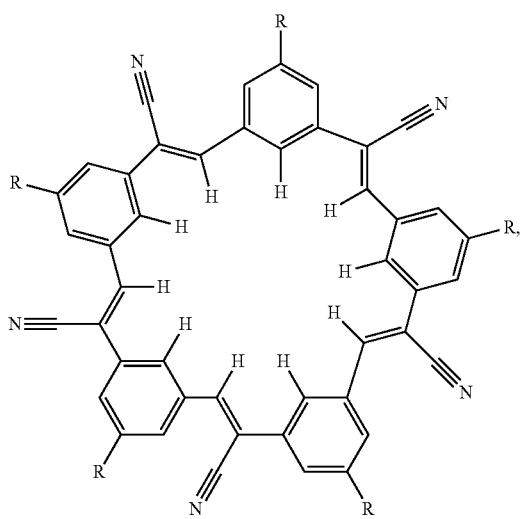

(IR)

wherein R is selected from the group consisting of alkenyl, alkyl, alkoxy, alkyl-NH-alkyl, aryl, cycloalkyl, heteroaryl, heterocycle, haloalkyl, hydrogen, iodo, —$OR^6$, —$N(R^7R^8)$, —$CO_2R^9$, —C(O)—$N(R^{10}R^{11})$, and $R^6$, $R^7$, $R^8$, $R^9$, $R^{10}$, and $R^{11}$ are each independently selected from the group consisting of alkenyl, alkyl, alkoxy, alkyl-NH-alkyl, aryl, arylalkyl, cycloalkyl, heteroaryl, heterocycle, haloalkyl, and hydrogen Substituent R may be chosen according to the properties one wishes to impart to the macrocycle. A group having a more pronounced hydrophilic or hydrophobic nature, for instance, may be chosen in order to increase a macrocycle's solubility in a given solvent or solvent mixture. Substituent characterized by different electronegativities may also be relied upon for the purpose of optimizing the complexation of a given anion. Similarly, the geometry and rigidity of the macrocycle and of its internal cavity, may be tweaked by choosing substituents characterized by differing degrees of steric hindrance. In representative examples, R may be an alkyl group having 1 to 6 carbon atoms, such as methyl, ethyl, n-propyl, iso-propyl, n-butyl, sec-butyl, iso-butyl, tert-butyl, n-pentyl, isopentyl, neopentyl, and hexyl. In an exemplary compound "cyanostar" CS, group R is a tert-butyl moiety:

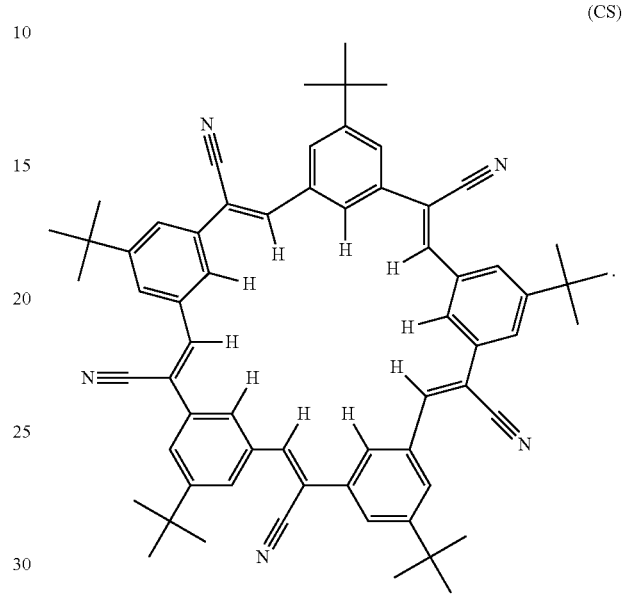

(CS)

In other exemplary embodiments, moiety R is an alkoxy group having 1 to 15 carbon atoms, such as methoxy, ethoxy, propoxy, 2-propoxy, butoxy, tert-butoxy, pentyloxy, hexyloxy, heptyloxy, octyloxy, nonyloxy, decyloxy, undecyloxy, dodecyloxy, trisdecyloxy, tetradecyloxy, and pentadecyloxy. In yet other embodiments, moiety R of macrocycles of Formula (I) and (IR) can be selected based upon the availability of known reagents from which the macrocycles are synthesized, as further explained in the synthetic schemes presented herein. For example, different R group substituents are presented in macrocycles I-1 through I-8:

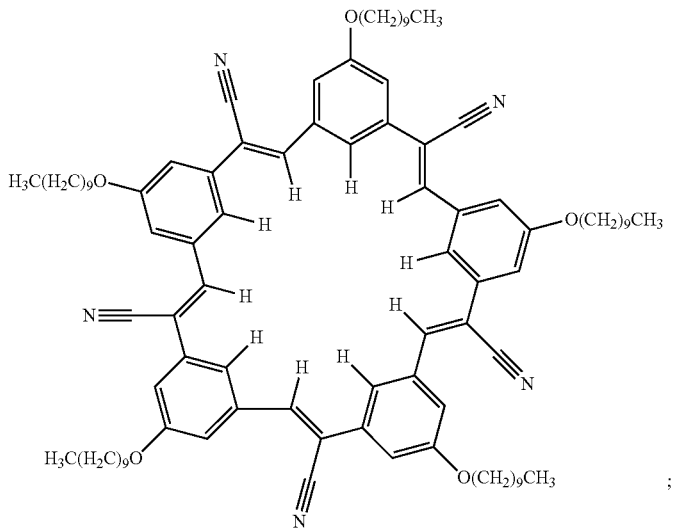

(I-1)

;

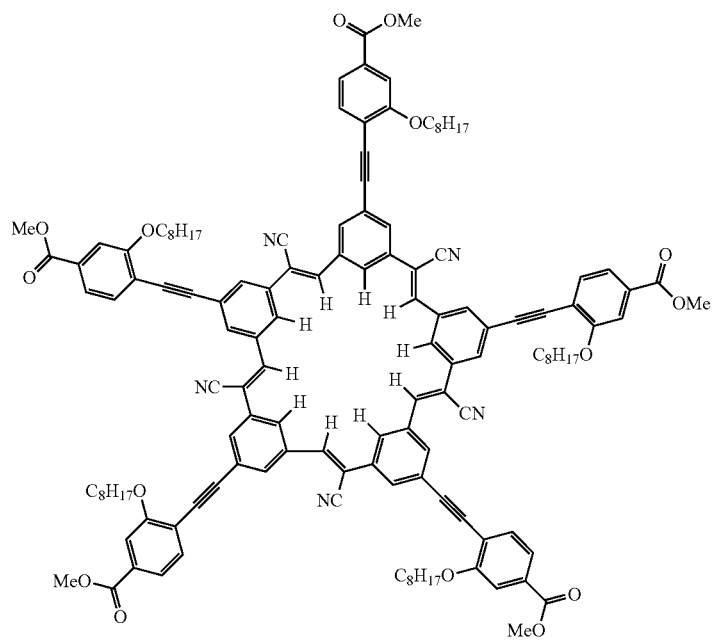
(I-2)
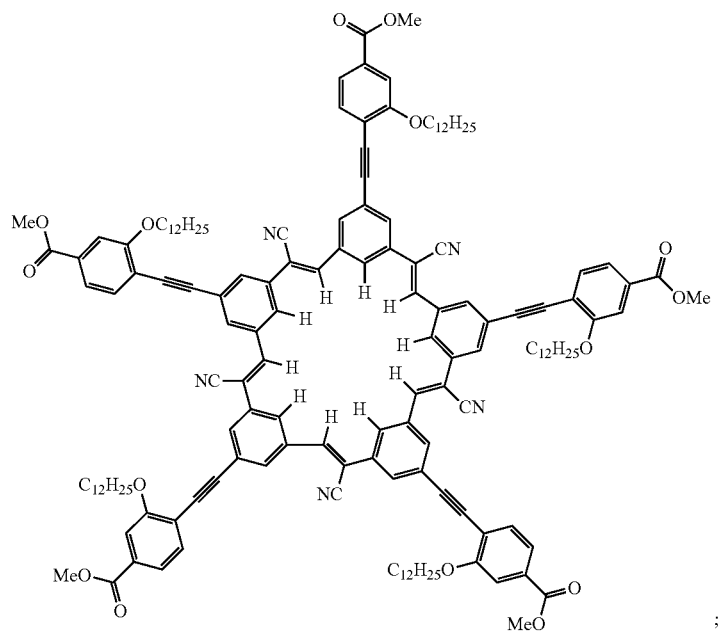
(I-3)

(I-4)
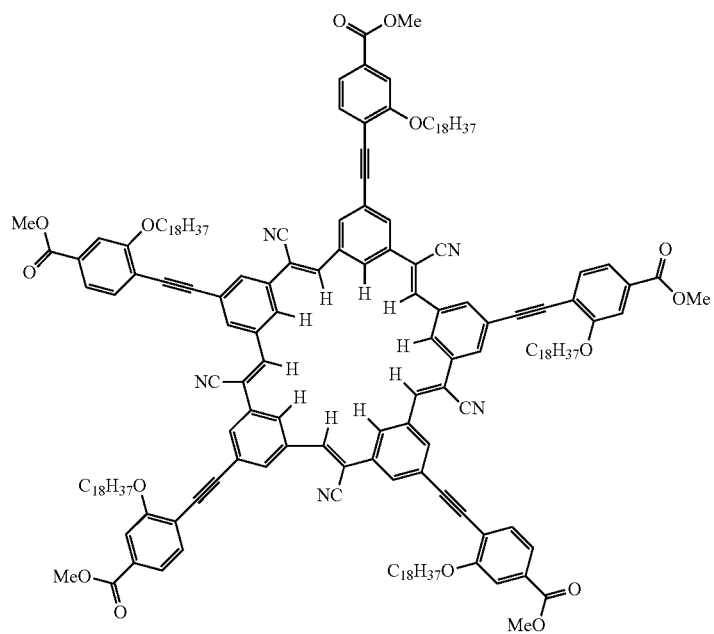
(I-5)
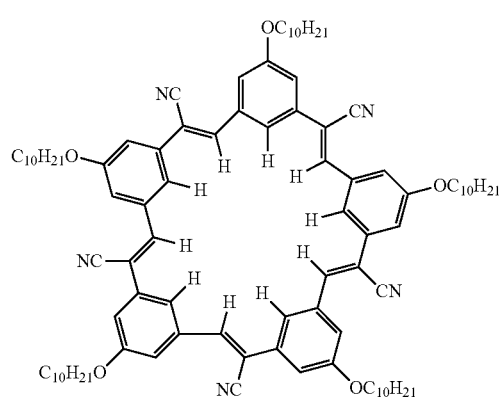
(I-6)
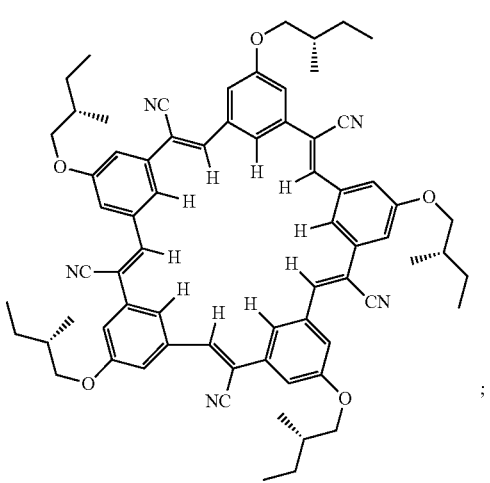

(I-7)
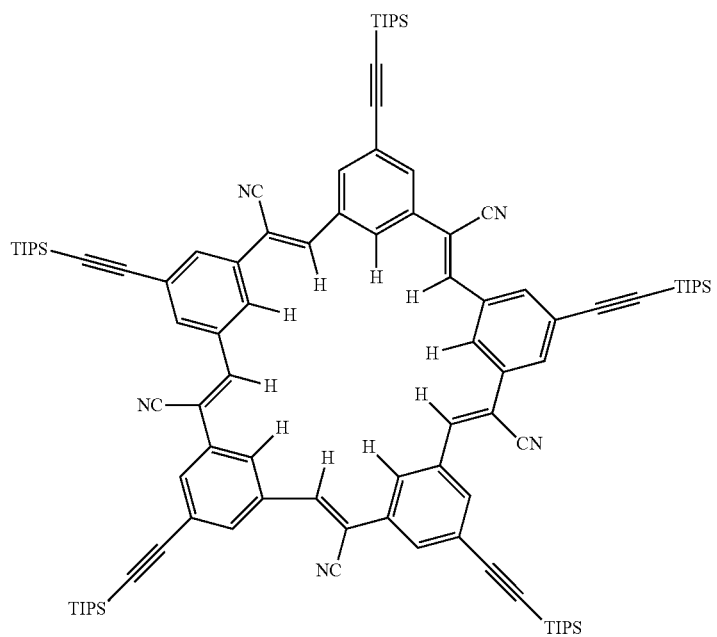
; and
(I-8)
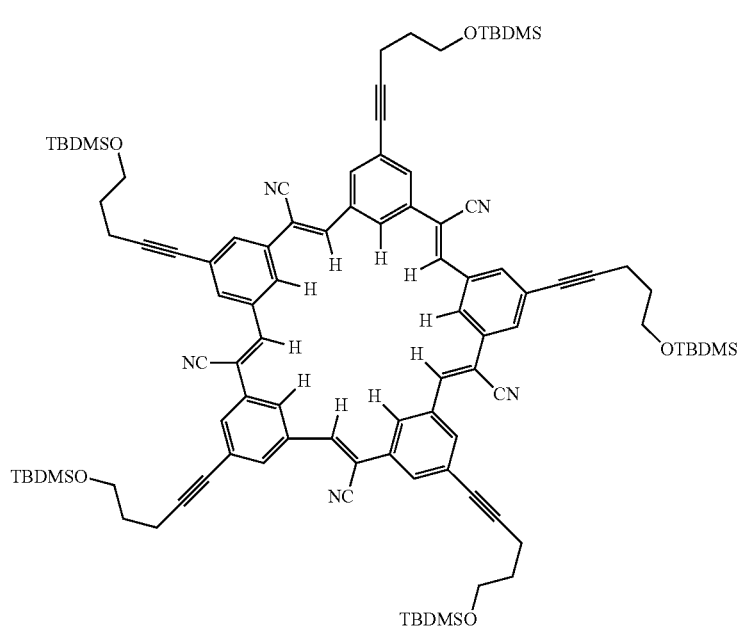

In other instances, moiety $R^1$ of Formula (I) can be a mono-iodo substituent, as depicted below for Formula (I-Iodo), wherein the remaining moieties $R^2$, $R^3$, $R^4$, and $R^5$ can include the substituents selected from the same group as for Formula (I):

A highly preferred embodiment of compounds having Formula (IR-Iodo) include Formula (CS-I), wherein the R groups are a t-butyl group, as illustrated below:

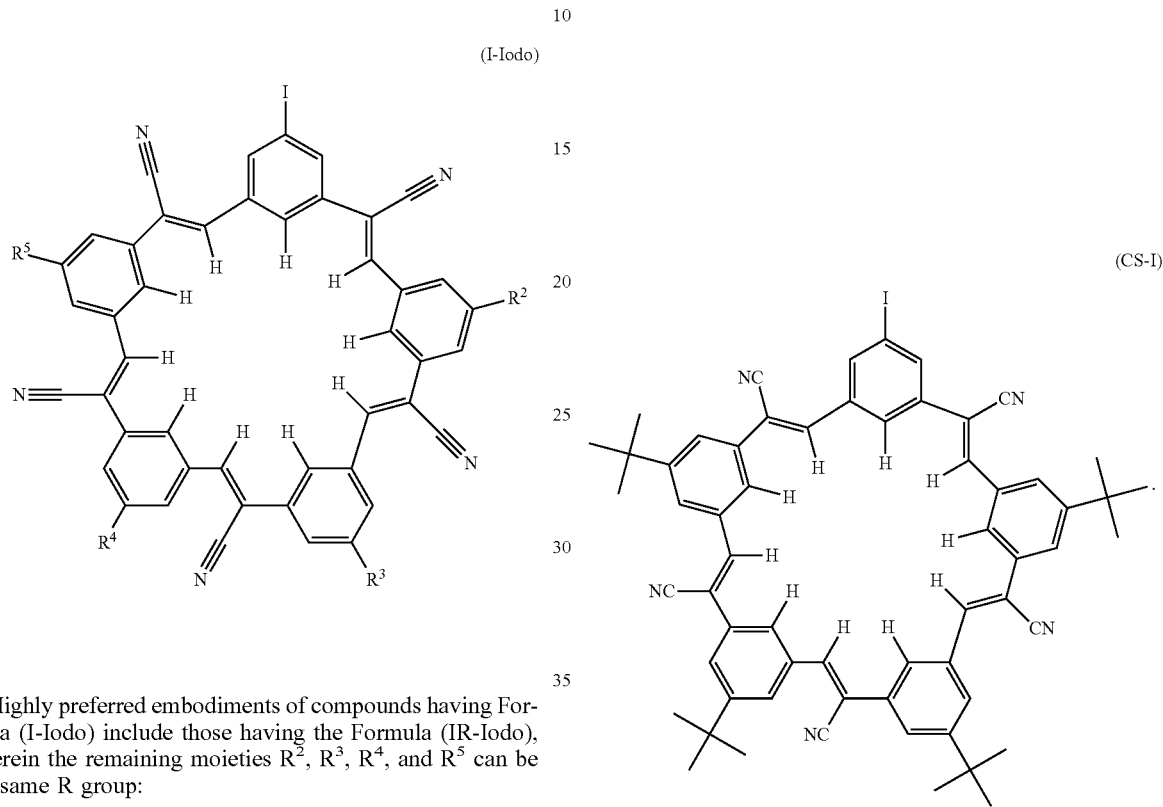

Highly preferred embodiments of compounds having Formula (I-Iodo) include those having the Formula (IR-Iodo), wherein the remaining moieties $R^2$, $R^3$, $R^4$, and $R^5$ can be the same R group:

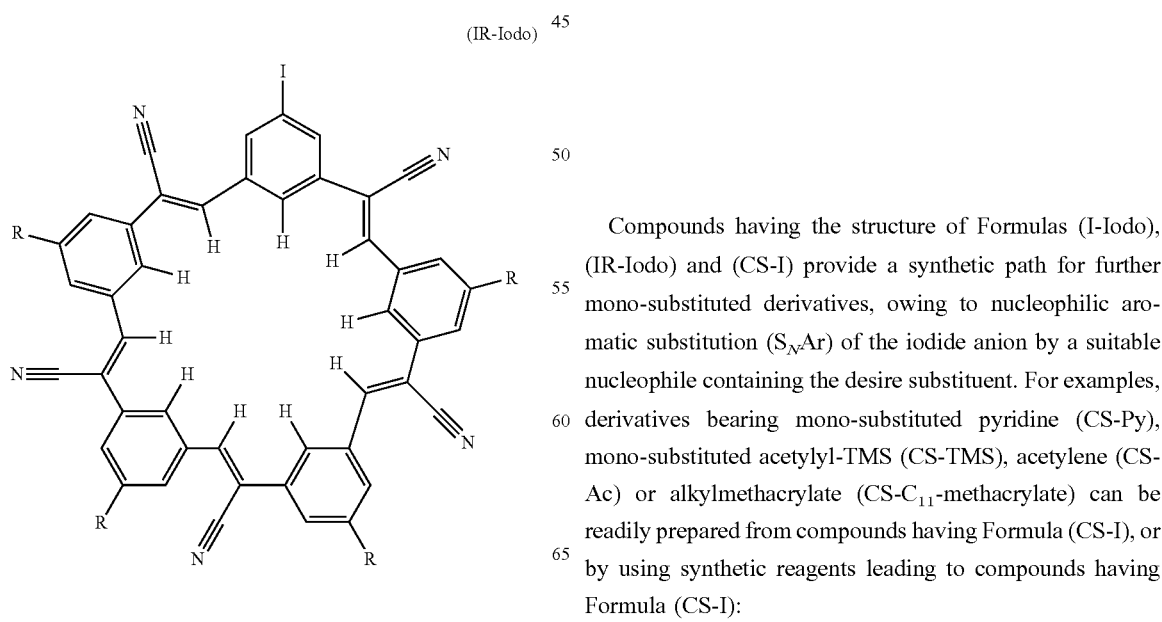

Compounds having the structure of Formulas (I-Iodo), (IR-Iodo) and (CS-I) provide a synthetic path for further mono-substituted derivatives, owing to nucleophilic aromatic substitution ($S_NAr$) of the iodide anion by a suitable nucleophile containing the desire substituent. For examples, derivatives bearing mono-substituted pyridine (CS-Py), mono-substituted acetylyl-TMS (CS-TMS), acetylene (CS-Ac) or alkylmethacrylate (CS-$C_{11}$-methacrylate) can be readily prepared from compounds having Formula (CS-I), or by using synthetic reagents leading to compounds having Formula (CS-I):

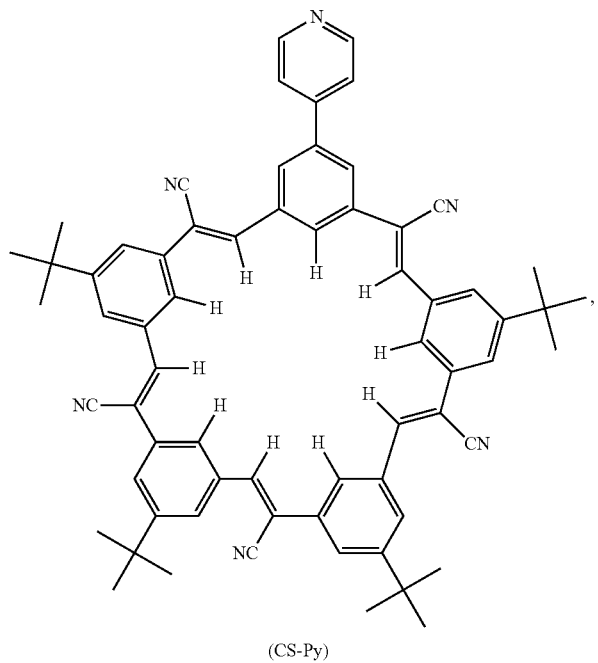
(CS-Py)
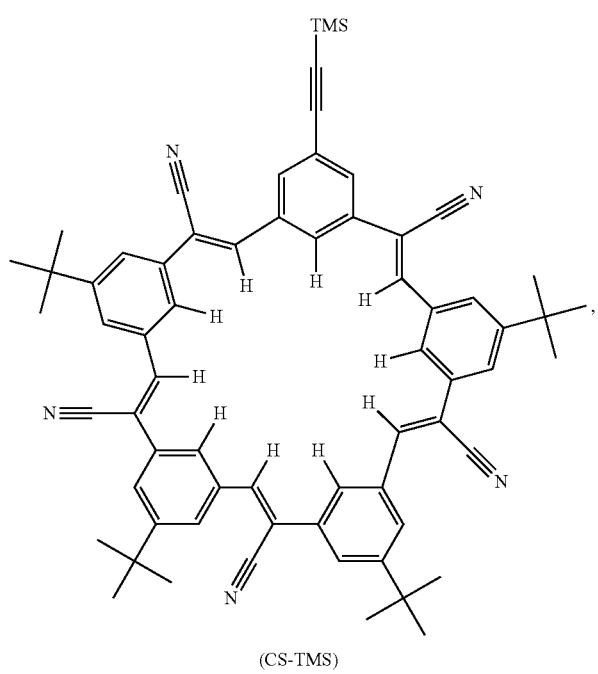
(CS-TMS)

-continued
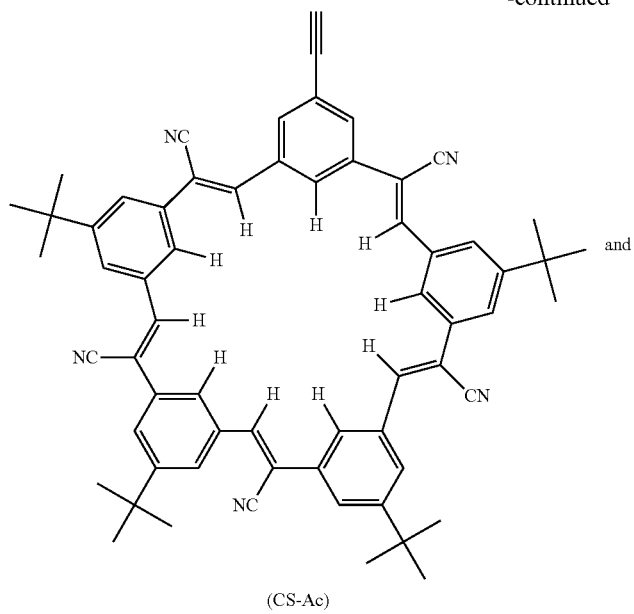
(CS-Ac)
and
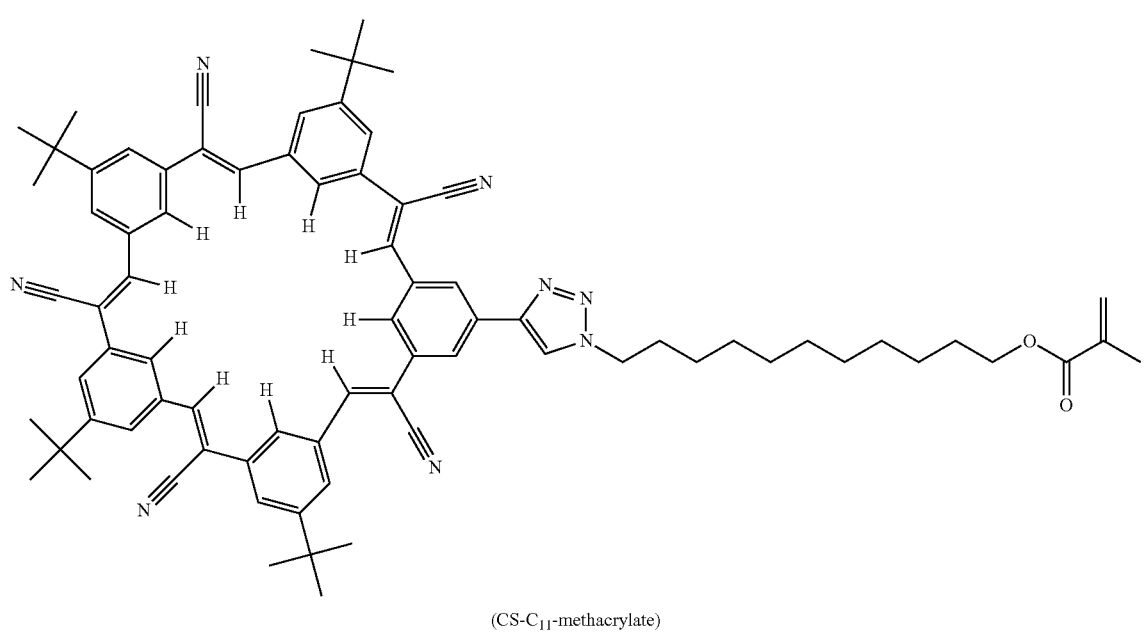
(CS-C$_{11}$-methacrylate)
The compounds having Formula (I-Iodo) also provide for novel, robust synthesis of bismacrocycles having Formula (IV) through reaction of two compounds having Formula (I-Iodo) with a suitable bifunctional crosslinking reagent that provides for an intermacrocyclic linker L, as depicted below:

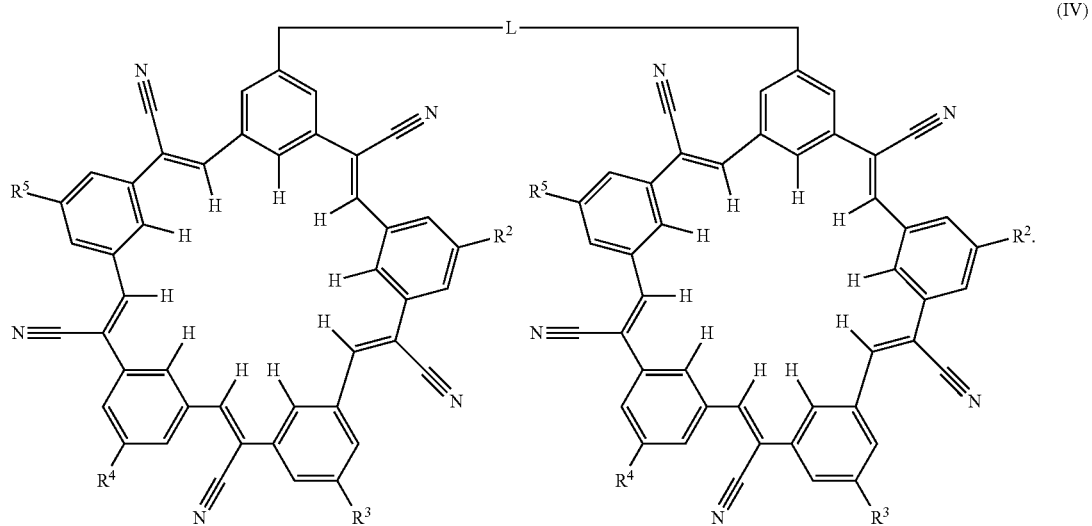

(IV)

Typically, the bifunctional crosslinking reagent leading to bismacrocycle compounds includes a linker L having alkyl chain lengths ranging from $C_{1-30}$, and more preferably from $C_{2-18}$. The linkers can include saturated or unsaturated alkyl moieties, as well as substituents within the alkyl moieties. One particularly useful substituent includes a third functional group (for example, amines, thiols, alcohols, activated carbonyls and carboxylates, polyhistidine moieties, among others) that permits crosslinking with another reactive group, such as those found on select activated resins or other substrate matrix supports, such as epoxides, hydrazydes, N-hydroxy-succinimide esters, metal chelate agents (such as polyhistidine (e.g., hexahistidine)), 3-(3-dimethylaminopropyl)carbodiimide hydrochloride (EDAC) carbodiimide coupling reagent, among others). Additionally, the reactive groups that displace the iodo-substituent contribute to the overall structure and length of linker L following crosslinking to form the bismacrocyclic structure of Formula (IV).

For example, the compound having Formula (CS-I) can provide for novel, robust synthesis of bismacrocycles through reaction of two compounds having Formula (CS-I) with a suitable bifunctional crosslinking reagent (for example, using a diazide dodecyl linker under click chemistry conditions). An example of one such bismacrocycle is illustrated by the compound having formula (IV-CS-12D):

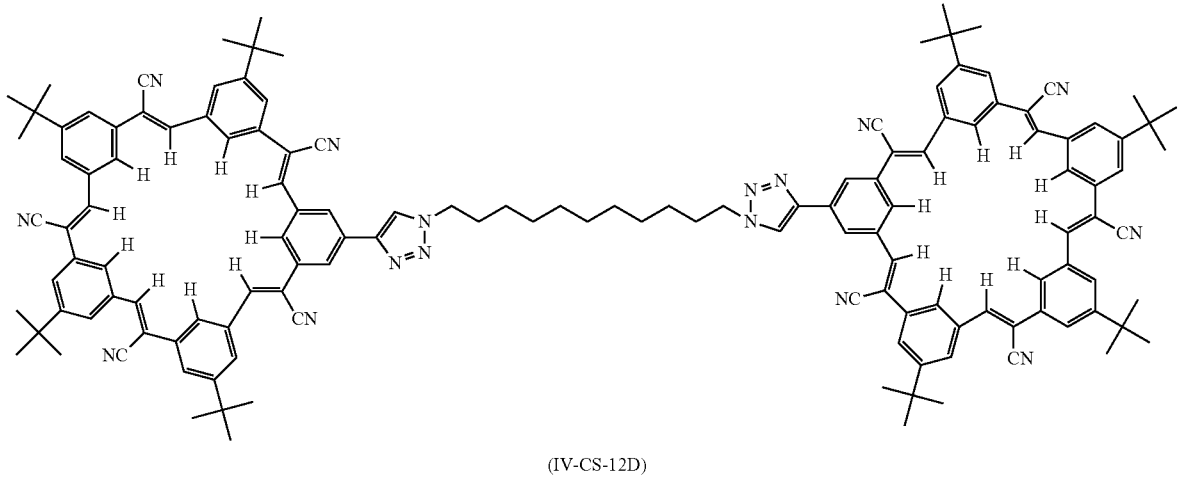 [SMILES: CC(C)(C)c1cc2cc(c1)/C(C#N)=C/c1cc(cc(C(C)(C)C)c1)/C(C#N)=C/c1cc(cc(C(C)(C)C)c1)/C(C#N)=C/c1cc(cc(C(C)(C)C)c1)/C(C#N)=C/c1cc(cc(-c3cn(CCCCCCCCCCCn4cc(-c5cc6cc(c5)/C(C#N)=C/c5cc(cc(C(C)(C)C)c5)/C(C#N)=C/c5cc(cc(C(C)(C)C)c5)/C(C#N)=C/c5cc(cc(C(C)(C)C)c5)/C(C#N)=C/c5cc(cc(C(C)(C)C)c5)/C(C#N)=C/6)nn4)nn3)c1)/C(C#N)=C/2]

(IV-CS-12D)

Compounds of formula (IV) provide structurally unique anion binding activity as clam-shell anion chelates. An example of one such binding geometry is depicted in FIG. 5 for the compound of formula (IV-CS-12D). Such unimolecular bivalent, anion coordination geometries make possible anion coordination and clearance using lower concentrations of bismacrocycle reagents as compared to unimacrocycle reagents, owing to the entropic advantages afforded by having two anion-coordinating macrocycle groups linked together. Typical unimolecular macrocycles can only bind anion targets efficiently under conditions where the concentration of the unimolecular macrocyles are above the dissociation constant for formation of the trimeric complex containing two unimolecular macrocycles in complex association with the target anion. By contrast, bismacrocycles are expected to display little concentration dependence as a function of bismacrocyccle concentration for binding an anion.

Synthesis of Poly-Cyanostilbene Macrocycles

The polycyanostilbene macrocycles can be easily prepared in a synthesis where a benzylic nitrile and benzaldehyde functional groups are reacted with each other, as illustrated in reaction Scheme A (in reactions Schemes A and B, R has the same meaning as described above). Both such groups are featured in a meta substituted difunctional non-symmeteric arene precursor of Formula (II):

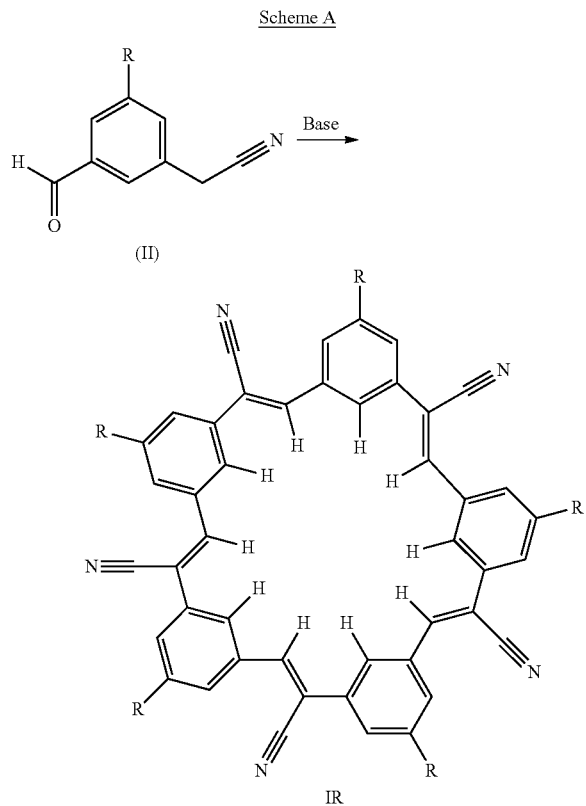

Without being bound to any particular theory, it is believed that the benzylic nitrile and benzaldehyde functional groups of (II) undergo base-catalyzed Knoevenagel self-condensation. Again without being bound to any particular theory, it is believed that the base may be acting as a template in the ring-closure step leading to the macrocyclic ring of (IR). The non-symmetric nature of arene (II) allows for chain extension to proceed in a linear manner through to the five-mer followed ultimately by cycle formation. In contrast, the reaction between two different but symmetric building blocks can only access cycles with even numbers.

The reaction is preferably carried out in the presence of a mild base. Representative examples of such bases include carbonate salts, such as $Li_2CO_3$, $Na_2CO_3$, $K_2CO_3$, $Rb_2CO_3$, $Cs_2CO_3$, $MgCO_3$, $CaCO_3$, $SrCO_3$, $BaCO_3$, and mildly basic amines, such as pyridine or piperidine.

Arene precursors of Formula (II) can be prepared, for instance, by oxidizing a hydroxymethyl-substituted 2-phenylacetonitrile molecule of Formula (III), as described in reaction Scheme B:

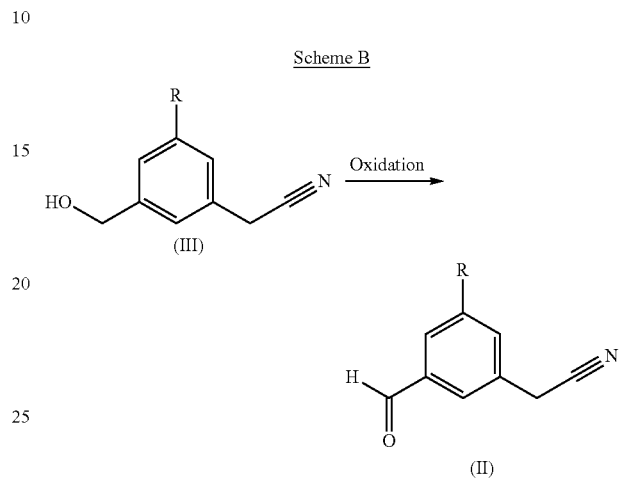

The oxidation of Scheme B is preferably carried out under selective conditions for the conversion of the alcohol group to an aldehyde, for instance with pyridinium chlorochromate (PCC), DMSO-based oxidations (Swern oxidation, Moffatt oxidation) or hypervalent iodine based oxidation (such as the Dess-Martin periodinane). Also contemplated are instances where group R is masked by a protecting group that is removed once the above oxidation step is completed.

Compounds having Formula (CS-I) can be prepared by reacting one part of the mono-iodo substituted building block reagent (3) with 15 parts of the tert-butyl building block reagent (4), according to Scheme C. Compounds having Formula (CS-Py) can be prepared by reacting one part of the mono-pyridyl substituted building block reagent (6) with 15 parts of the tert-butyl building block reagent (4), according to Scheme D. Each reaction is run under statistical conditions and the single-substituted product is separated by chromatography. Once the compound of formula (CS-I) is obtained, derivatives can be made directly with conventional substitution chemistries well known in the art.

Compound having Formula (IV-CS-12D) can be prepared from (CS-I), for example, according to Scheme E that employs (CS-TMS) and (CS-Ac) as intermediates. Compounds having Formula (IV) can be prepared in a similar manner described for (IV-CS-12D), for example, according to Scheme E that employs reagents having the desired substituents as intermediates.

These syntheses are described in detail in the Examples.

Scheme C

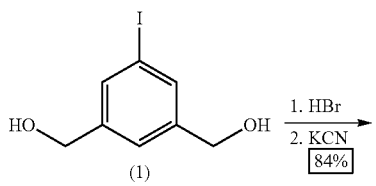

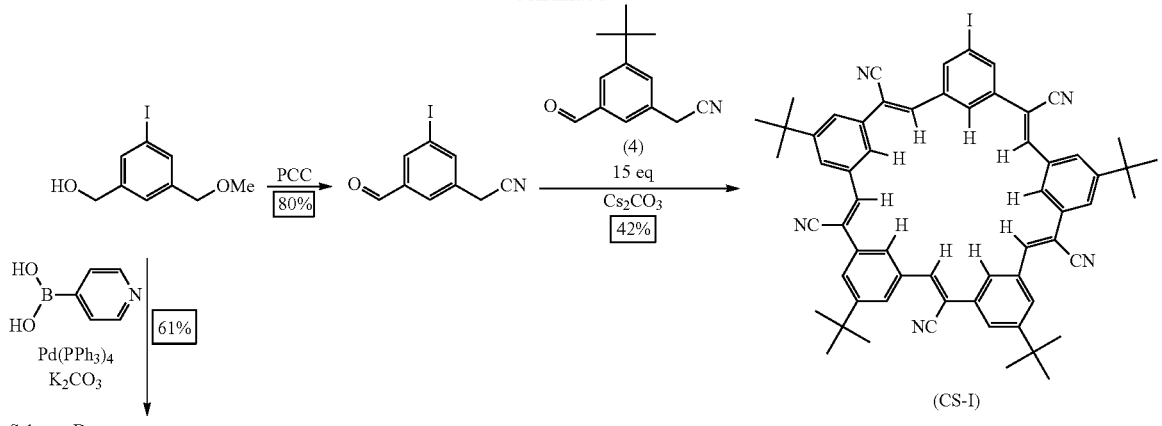
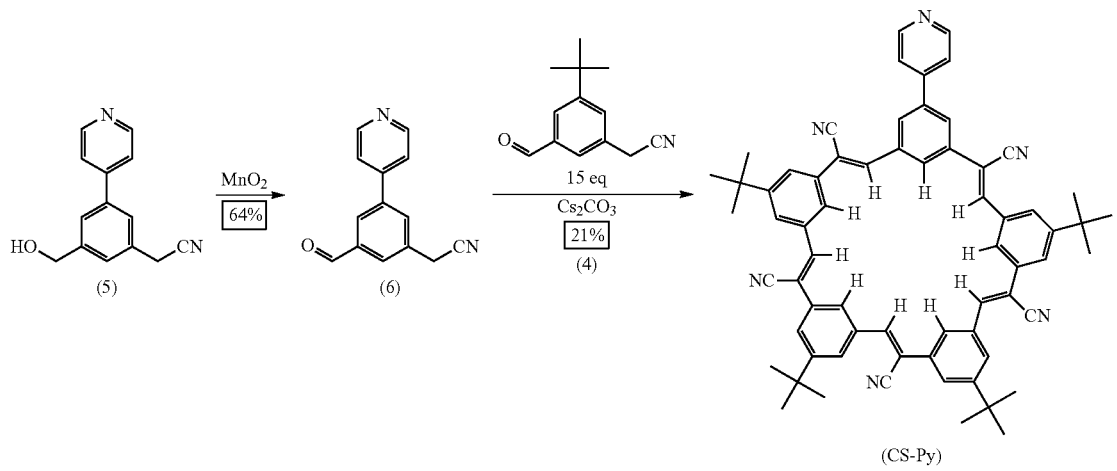
Scheme D

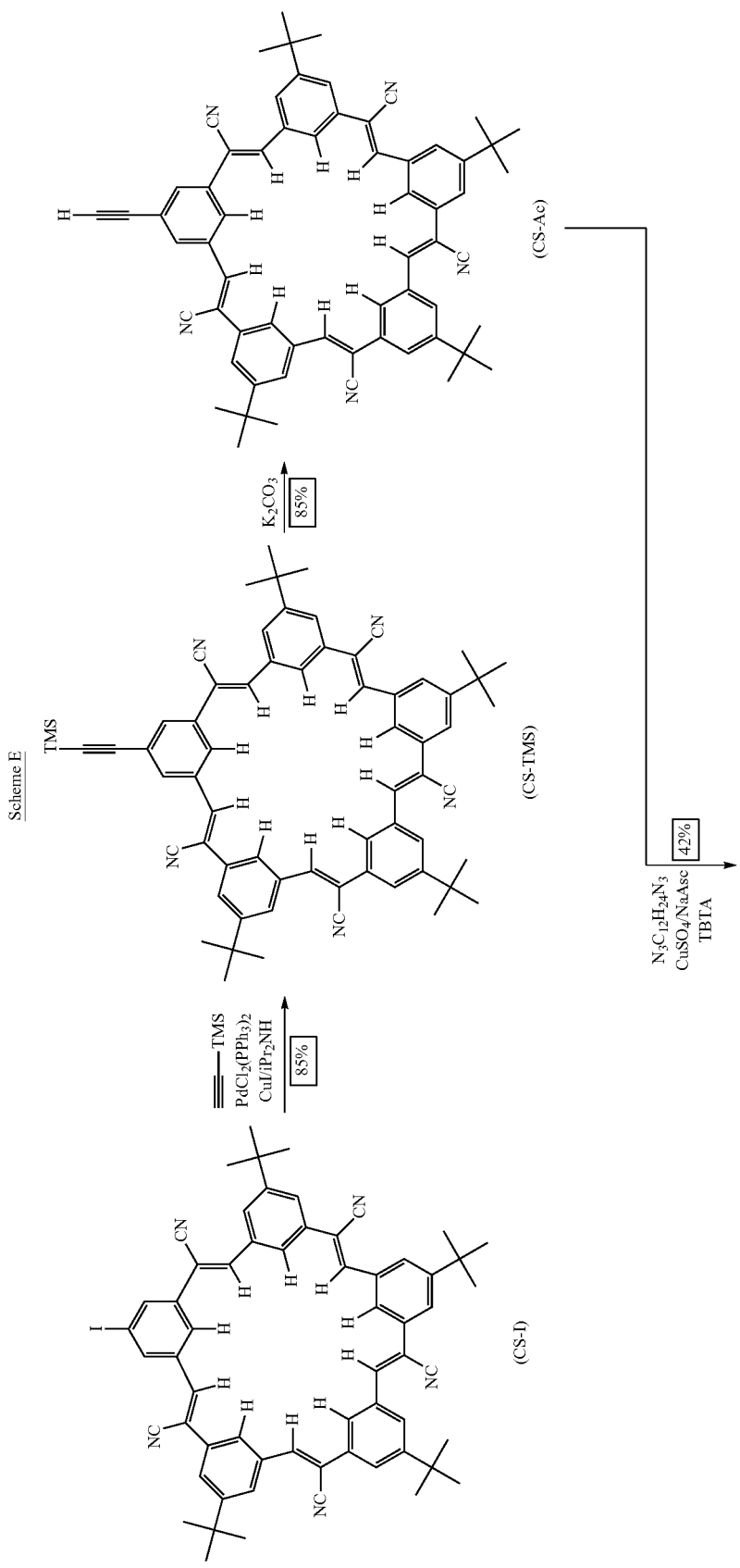
Scheme E

-continued
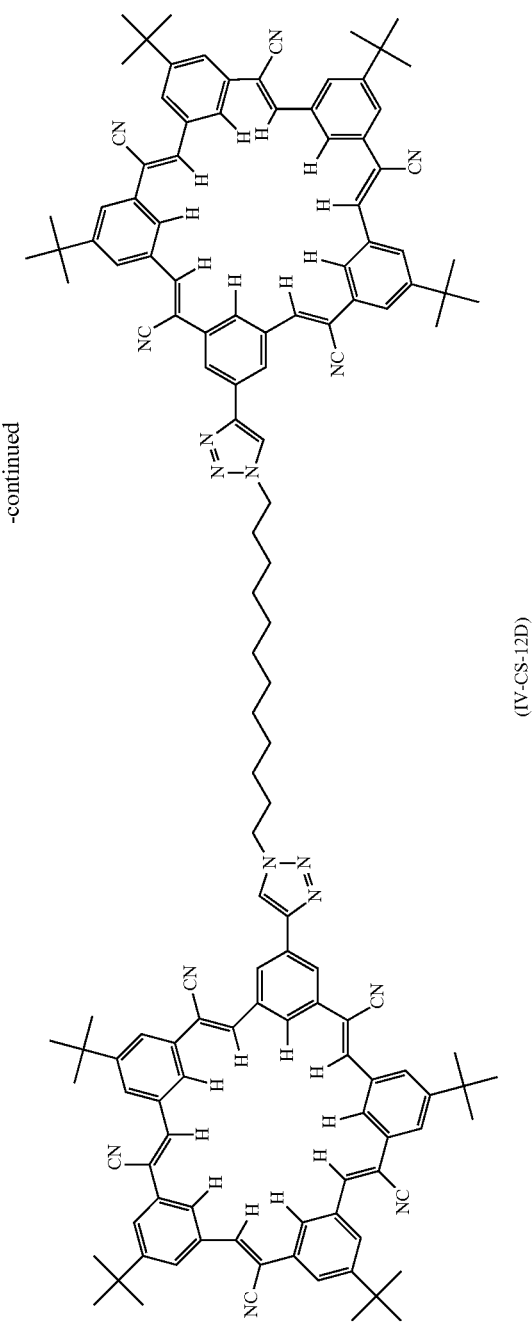
(IV-CS-12D)

Complexes with Anions

The electron-deficient π-conjugated character of cyanostilbenes, which found use as semiconductor materials in the form of para-linked polymers, together with current investigations of their aggregation-induced emission raises the potential for electronic and photochemical properties. In addition, the poly-cyanostilbene macrocycles exhibit novel recognition properties that are exemplified by their self-assembly as 2:1 sandwich complexes around large anions like $BF_4^-$, $ClO_4^-$ and $PF_6^-$. Such anions are usually considered to be "weakly coordinating" and typically require positive charges to capture them. For instance, strong affinities ($1.3 \times 10^6$ $M^{-1}$) are observed for $PF_6^-$ in acetonitrile inside Nitschke's octacationic self-assembled tetrahedron cages. When neutral receptors are used, such as with Rebek's neutral dimer capsules, $PF_6^-$ is bound with more moderate affinities of $4.2 \times 10^3$ $M^{-1}$ in chloroform. By contrast, the poly-cyanostilbene macrocycles have been found to bind the same $PF_6^-$ anion with much higher overall stabilities, with a $\beta_2$ of about $10^{12}$ in 40% methanol in dichloromethane, within their neutral cavities, thus raising the possibility of use in applications where such anions are featured, such as lithium-ion batteries.

Therefore, in another aspect, there are provided complexes comprising a cyanostar macrocycle and an anion X, as depicted in Formula ($I_C$):

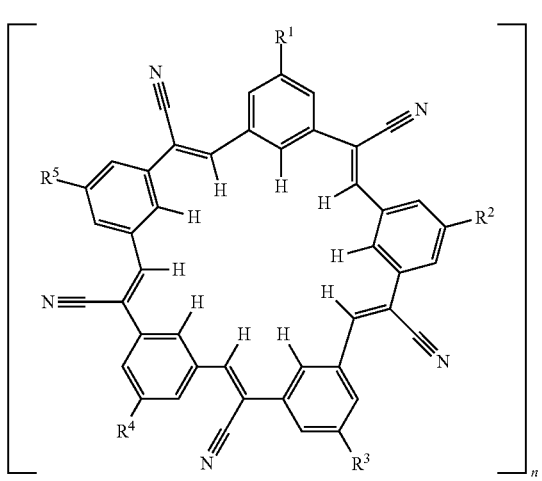

($I_c$)

As anticipated supra, stronger binding has been found to occur with anions characterized by a large ionic diameter and diffuse charge. Accordingly, in representative embodiments, anion X may be a tetrafluoroborate ($BF_4^-$), perchlorate ($ClO_4^-$), and hexafluorophosphate ($PF_6^-$). Other example anions include bis(trifluoromethanesulfonyl)imide ($N(SO_2CF_3)_2^-$), 1,1,2,2,2-pentafluoro-N-[(pentafluoroethyl)sulfonyl]ethanesulfonamide ($N(SO_2C_2F_5)_2^-$), mesylate ($CH_3SO_3^-$), triflate ($CF_3SO_3^-$), arsenate ($AsO_4^{3-}$), hexafluoroarsenate ($AsF_6^-$), tetrachloroaluminate ($AlCl_4^-$), phosphate ($PO_4^{3-}$), hydrogenophosphate ($HPO_4^{2-}$), dihydrogenophosphate ($H_2PO_4^-$), sulfate ($SO_4^{2-}$), hydrogen sulfate ($HSO_4^-$), tetracyanoborate ($B(CN)_4^-$), halides ($Cl^-$, $Br^-$, $I^-$), cyanide, perbromate ($BrO_4^-$), periodate ($IO_4^-$), fluoride ($F^-$), bifluoride ($HF_2^-$), pertechnetate ($TcO_4^-$), monosubstituted phosphate esters ($RPO_4^{2-}$), disubstituted phosphate esters ($R_2PO_4^-$), organosulfonates ($RSO_3^-$), thiocyanate, ($SCN^-$), azide ($N_3^-$), triiodide ($I_3^-$), carbonate ($CO_3^{2-}$), monohydrogen carbonate ($HCO_3^-$), iron tetrachlorate ($FeCl_4^-$), and platinum hexachlorate ($PtCl_6^{2-}$).

In instances where the anion X bears one negative electric charge, i.e. is mono-ionic, n may be 1 or 2, depending on factors such as the relative amounts of the macrocycle and anion when the complex is formed. In the complex of Formula (III), $R^1$, $R^2$, $R^3$, $R^4$, and $R^5$ have the same meaning as defined above, and may all be the same group, for instance a tert-butyl group as in molecule CS. In one exemplary synthetic method, the complexes may be prepared by adding a salt of anion X to a solution of a poly-cyanostilbene macrocycle of Formula (I), as illustrated in Scheme F:

Scheme F

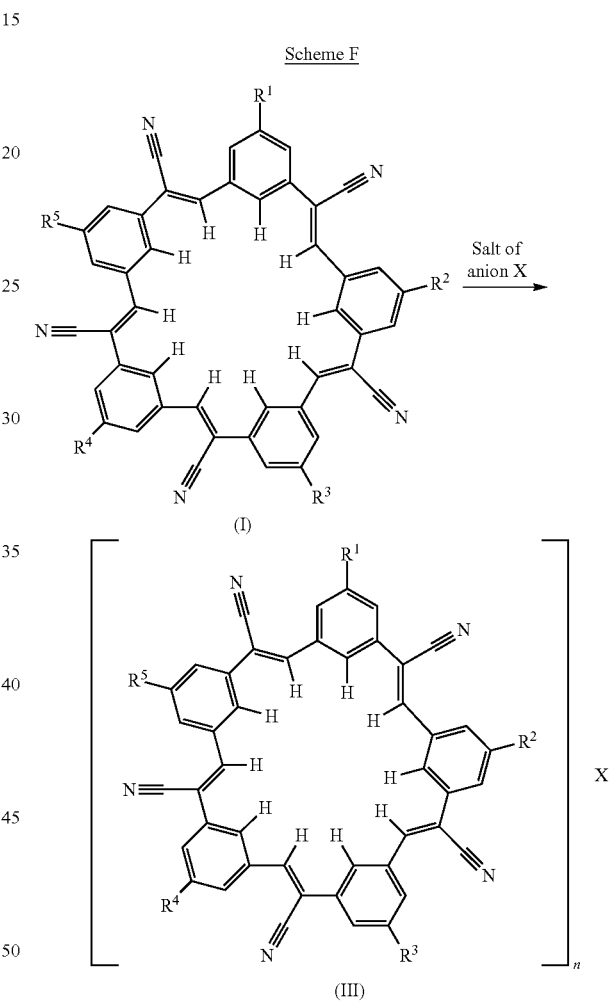

By way of example, a salt MX including anion X and positive counterion M may be added to a solution of (I). In instances where X is a monoanion, such as tetrafluoroborate ($BF_4^-$), perchlorate ($ClO_4^-$), or hexafluorophosphate ($PF_6^-$), the counterion may be chosen from among monocations, for example, those of alkali metals or ammonium, or dications such as those of alkaline earth metals. Once formed, the complex may be isolated alongside a desired counterion(s) by methods known in the art, for example, precipitation and/or anion exchange chromatography.

Figure 6:
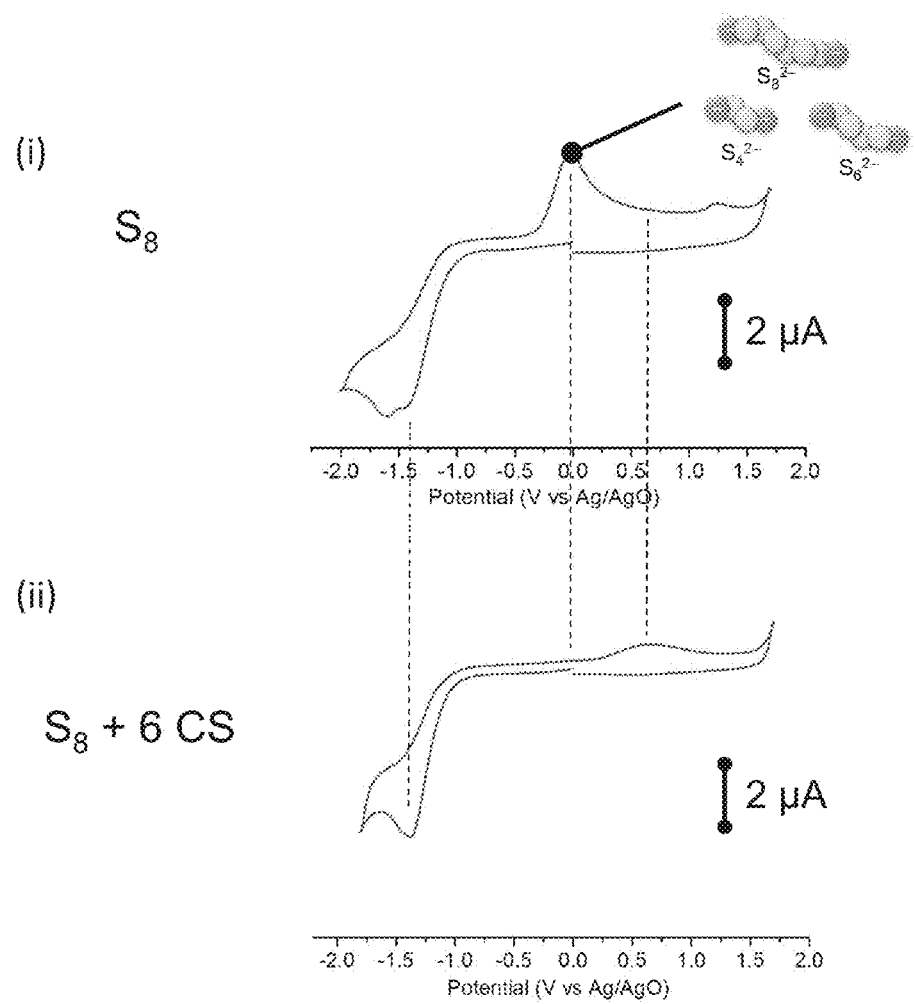
FIG. 6 depicts electrochemical reduction of elemental sulfur ($S_8$) to form polysulfides in solution, e.g., $S_4^{2-}$, $S_6^{2-}$ and $S_8^{2-}$ (panel (i)) and the electrochemical reduction profile of polysulfide anions complex with a cyanostar (panel (ii)). Conditions: 2 mM CS, 0.1M TBATFSI, $CH_2Cl_2$, 200 mVs$^{-1}$ scan rate, $GC_{we}$-$Pt_{ce}$ Ag electrodes.
Figure 7A:
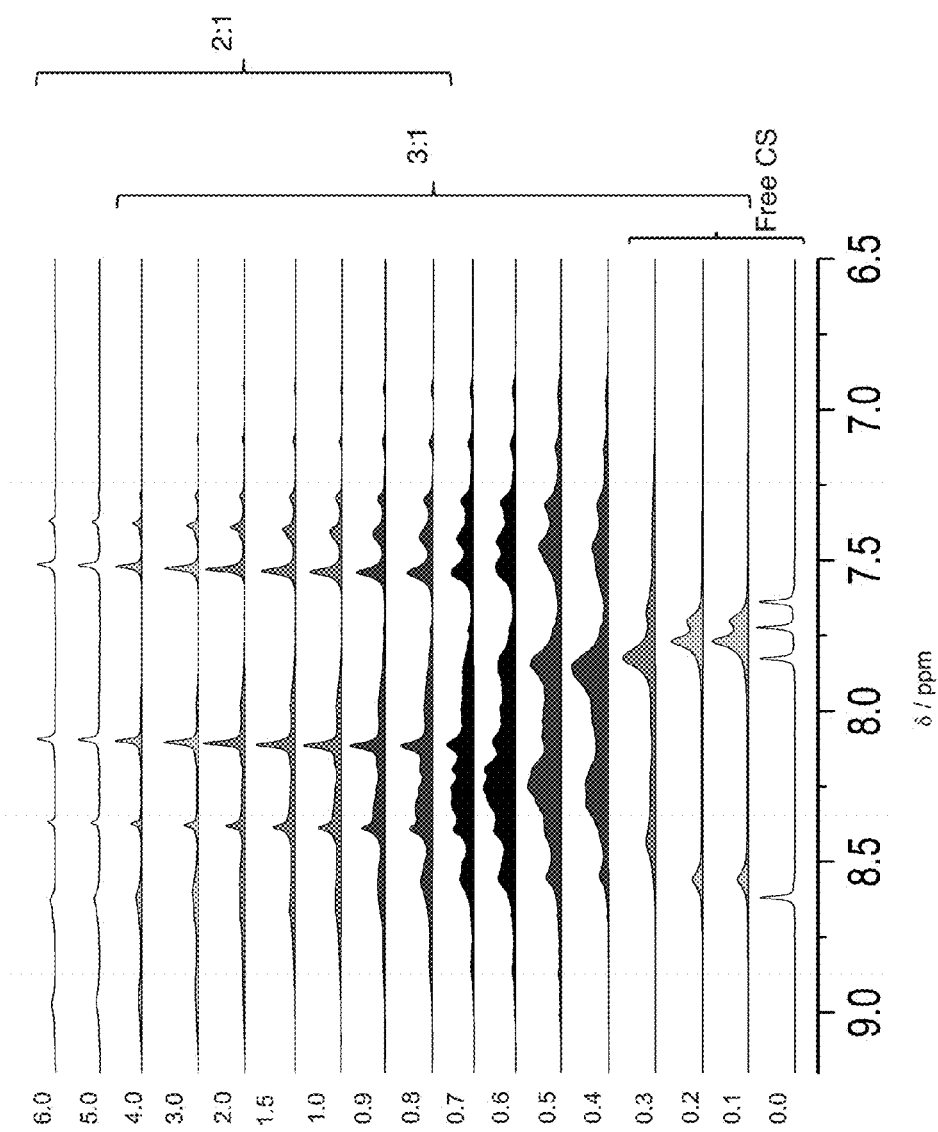
FIG. 7A depicts exemplary $^1$H NMR spectra of CS (10 mM), $CD_2Cl_2$ with added equivalents of tetrabutylammonium pyrophosphate (PPi). The cyanostar:anions ratios (at right) represent stoichiometries for the complexes.
Figure 7B:
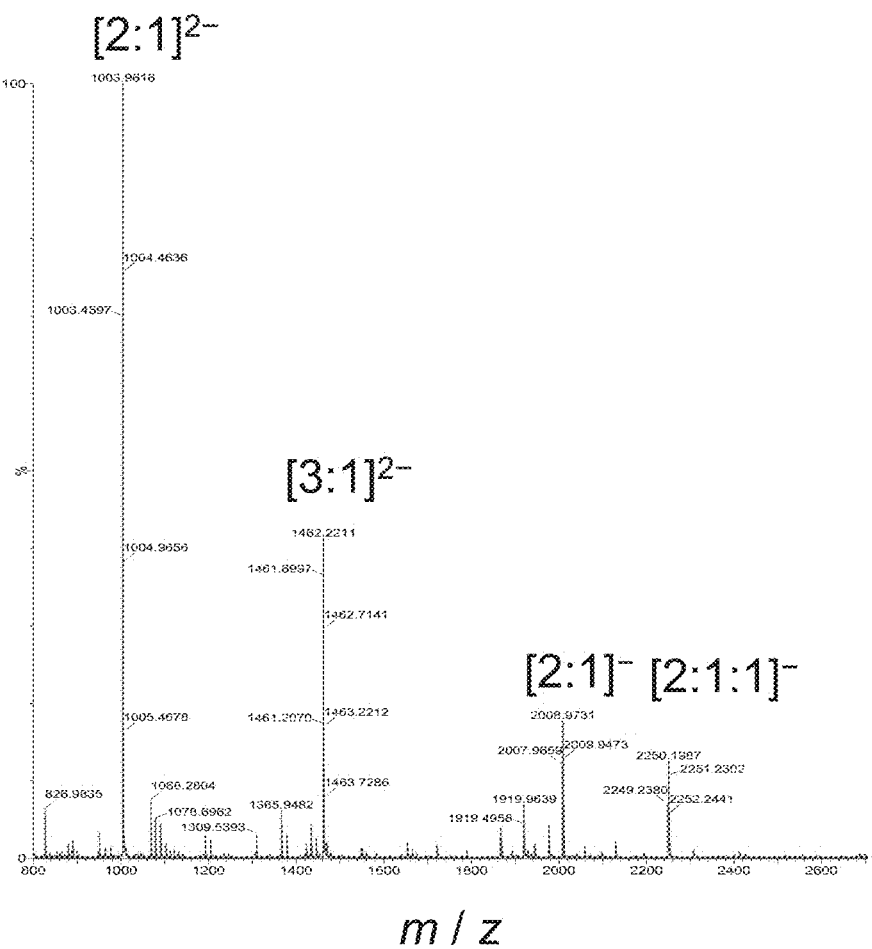
FIG. 7B depicts exemplary ESI-MS spectra of CS (1 mM) with 1 eq. PPi, $CH_2Cl_2$, Cone voltage 20 V, 50° C. The ratios assigned to each peak represent stoichiometries for the complexes as either cyanostar:anions ratios or cyanostar:anion:cation ratios.

Other anions contemplated in compositions and methods of the invention include polysulfides. Polysulfides are a class of anions of general formula $S_n^{x-}$ where n=1-8, and x=1 or 2. For example, $S_2^{2-}$, $S_3^{2-}$, $S_4^{2-}$, $S_6^{2-}$ and $S_8^{2-}$. As evidence for complexation, electrochemistry was conducted (FIG. 6). The reduction of elemental sulfur ($S_8$) occurs at around −1.5 V to form polysulfides in solution, e.g., $S_4^{2-}$, $S_6^{2-}$ and $S_8^{2-}$ (FIG. 6, panel (i)). These appear to be oxidized back to the $S_8$ at around 0 V. Upon addition of cyanostar, however, the polysulfide anions complex with the cyanostar and their reoxidation peak shifts to around +0.6 V (FIG. 6, panel (ii)). This shift in re-oxidation peak has been seen elsewhere for other electrogenerated anions, e.g., see *J. Am. Chem. Soc.* 2016, 138, 15057-15065 10961 Pyrophosphate (PPi), $P_2O_7^{4-}$, and its protonated congeners, e.g., $HP_2O_7^{3-}$, $H_2P_2O_7^{2-}$ and $H_3P_2O_7^{-}$, can form a complex with cyanostars. See FIG. 7A for $^1H$ NMR spectra consistent with showing the change in the cyanostar aromatic peaks indicative of binding pyrophosphate. The signature for a triple stack of cyanostars is seen as indicated with the graded grey signature for a stoichiometry of 3:1 CS:pyrophosphate that is present from 0.1-4 eq of added pyrophosphate. The signature of the 2:1 CS:pyrophosphate is also observed later on in the titration (>0.8 eq.). The ESI-MS (FIG. 7B) also shows evidence of complexation as 2:1 and 3:1 dianions indicative of binding the congener $H_2P_2O_7^{2-}$. The peak for the 2:1 is indicative of complexation with congener $H_3P_2O_7^{-}$.

Organic anions that are sufficiently small can form complexes with cyanostars. Examples of tetrazine anions that form such complexes are illustrated in FIG. 8 and as presented in Benson, C. R.; Fatila, E. M.; Lee, S.; Marzo, M. G.; Pink, M.; Mills, M. B.; Preuss, K E.; Flood, A H., "Extreme Stabilization and Redox Switching of Organic Anions and Radical Anions by Large-cavity, CH Hydrogen-Bonding Cyanostar Macrocycles," *J. Am. Chem. Soc.* 2016, 138, 15057-15065 ("Benson et al. (2016)"), which is incorporated by reference in this entirety.

Figure 8A:
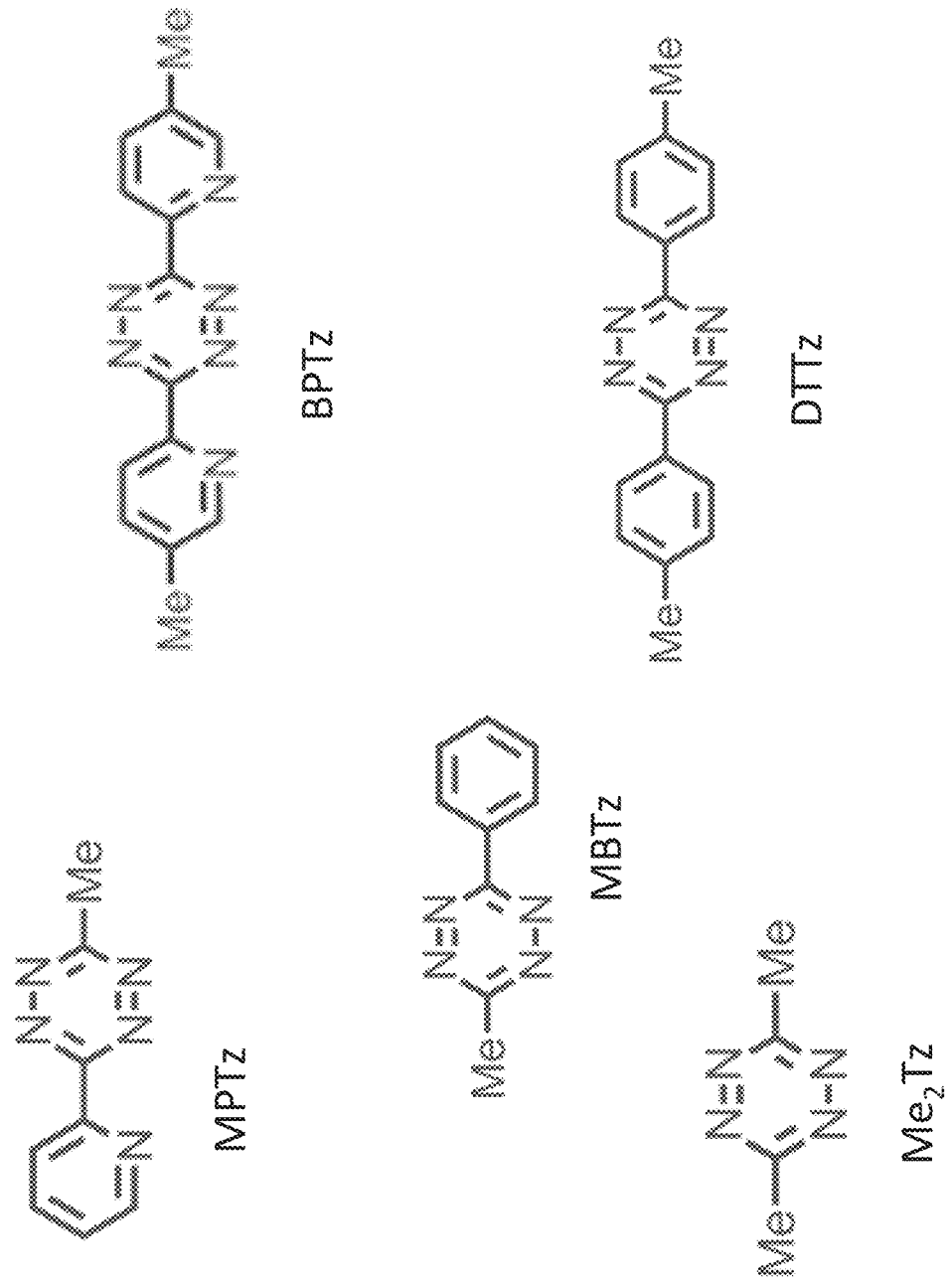
FIG. 8A depicts chemical structures of exemplary tetrazine anions.
Figure 8B:
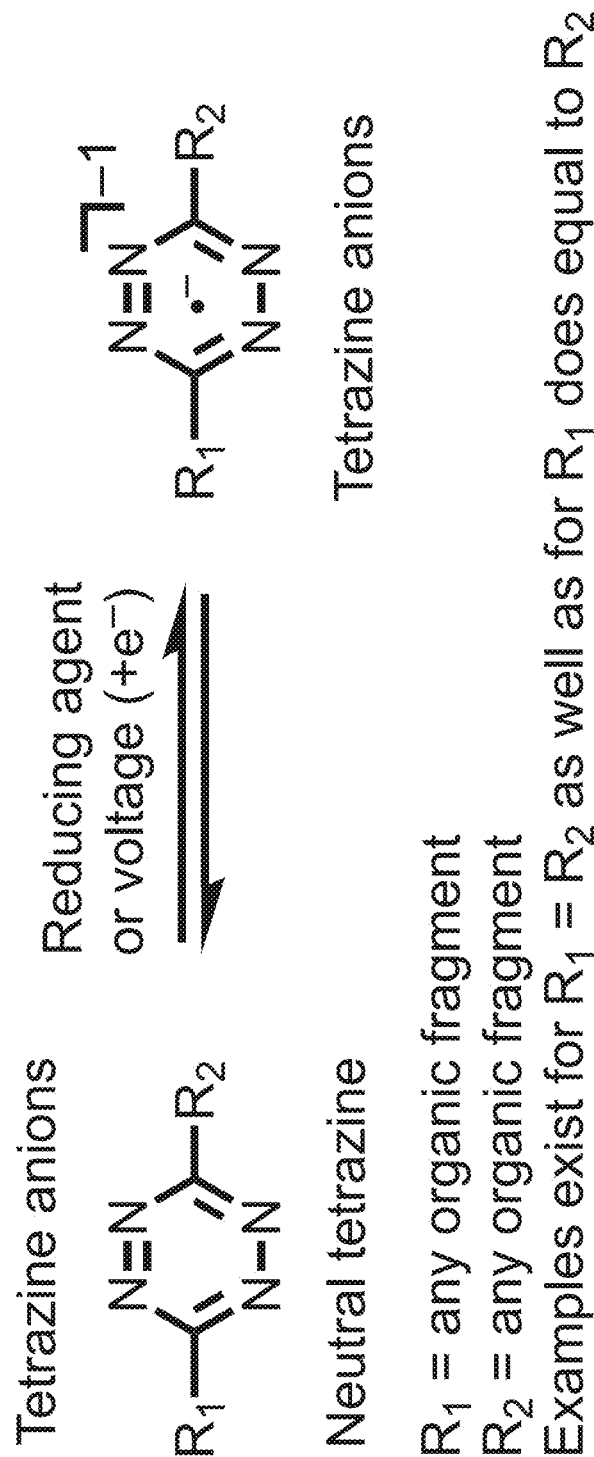
FIG. 8B depicts an exemplary electrochemical reaction of neutral tetrazine to form tetrazine anions, as affected by a reducing agent or voltage. $R_1$ and $R_2$ can be any organic fragment, either identical or different.
Figure 9A:
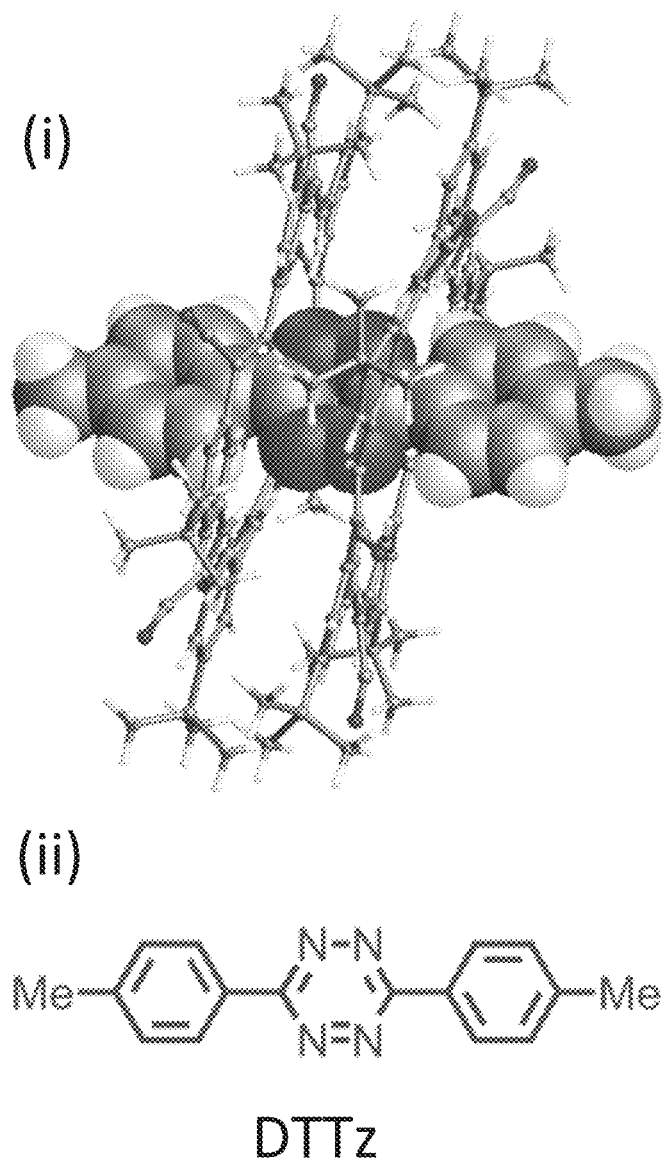
FIG. 9A depicts a crystallographic image of a complex formed between DTTz and CS (panel (i)) and the chemical structure of DTTz (panel (ii)).
Figure 9B:
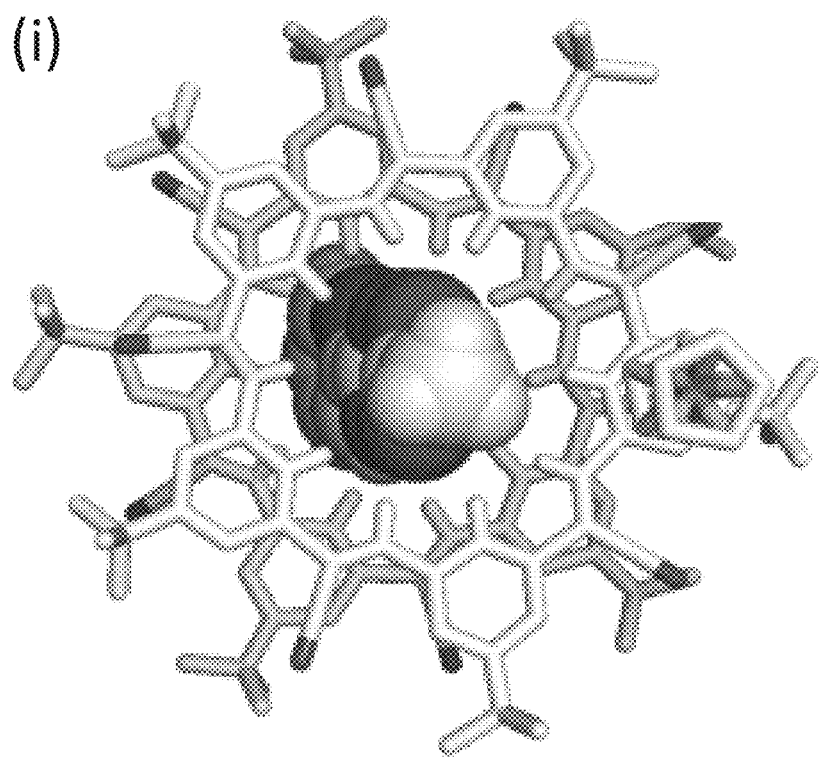
FIG. 9B depicts a crystallographic image of a complex formed between MPTz and CS (panel (i)) and the chemical structure of MPTz (panel (ii)).
Figure 9B:
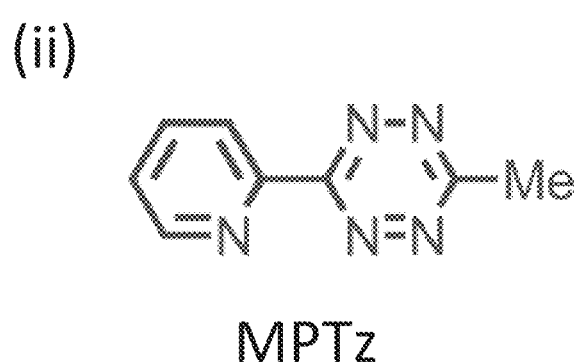

For a specific range of tetrazine anions, see FIG. 8A. A wide range of tetrazines is possible as based on substitutions on the 1 and 4 positions both symmetrically and non-symmetrically (FIG. 8B). For evidence of binding of CS with a tetrazine anion, specifically a crystal structure of CS with the tetrazine anion DTTz, see FIG. 9A (panels (i) and (ii)). See also FIG. 9B (panels (i) and (ii)) for a crystal structure of CS with the tetrazine anion MPTz.

Figure 10:
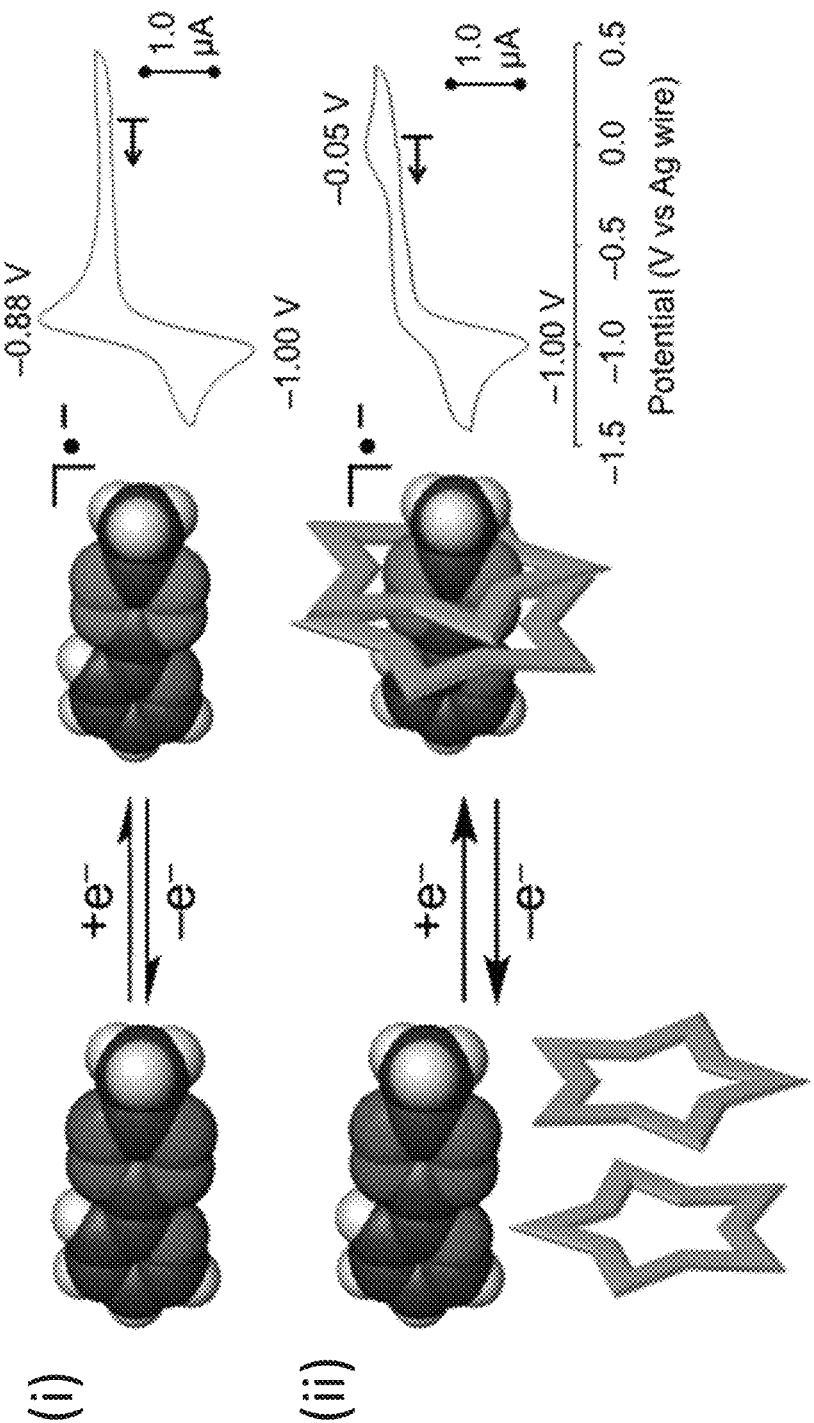
FIG. 10 depicts exemplary reactions and electrochemistry profiles of CVs of MPTz before the addition of 2 equiv of cyanostar (panel (i)) and after the addition of 2 equiv of cyanostar (panel (ii)). Conditions: 1.0 mM MPTz, 0.1 M TBABPh$_4$, $CH_2Cl_2$ $N_2$, 200 mV s$^{-1}$ scan rate, glassy carbon working electrode, Pt wire counter electrode, Ag wire quasireference, 298 K, referenced to $E_{pc}$ MPTz=−1.00 V.

Additional evidence for capturing organic anions comes from electrochemistry (FIG. 10). The electrochemistry provides a key signature for complexation of redox-driven anions. FIG. 10A shows a cyclic voltammogram of tetrazine MPTz with a peak at −1.00 V associated with reduction to form the tetrazine anion and then its re-oxidation back to the neutral form at −0.88 V. When cyanostar is added (as shown in FIG. 10B), the re-oxidation peak is seen to have shifted to −0.05 V, which is indicative of complexation of the tetrazine anion. Other substituted forms of the tetrazines Me$_2$Tz, MBTz, BPTz, and DTTz behave the same way as shown, respectively, as illustrated in Figures S11, S12. S13, and S14 in the Supporting Information of the Benson et al. (2016), which is incorporated herein in its entirety.

Figure 11A:
FIG. 11A depicts an exemplary electrochemical reaction of an exemplary neutral dithiadiazolide (DTDA) to form a dithiadiazolides anion, as affected by a reducing agent or voltage.
Figure 11B:
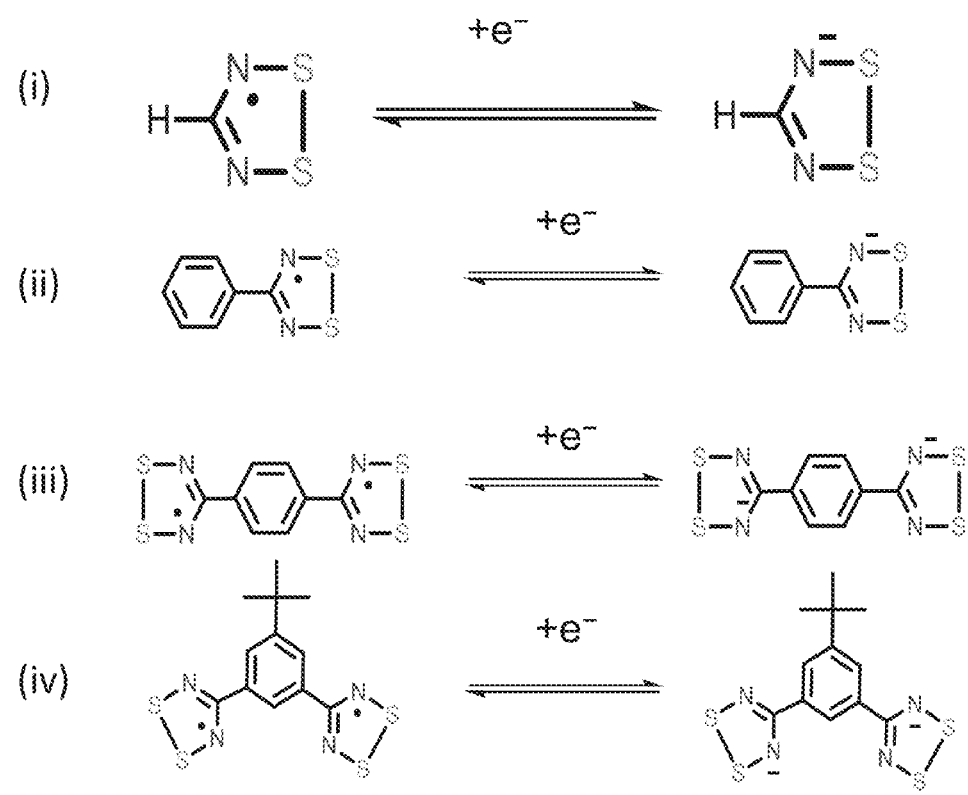
FIG. 11B depicts exemplary electrochemical reaction of an exemplary neutral dithiadiazolides to form dithiadiazolides anions.
Figure 12:
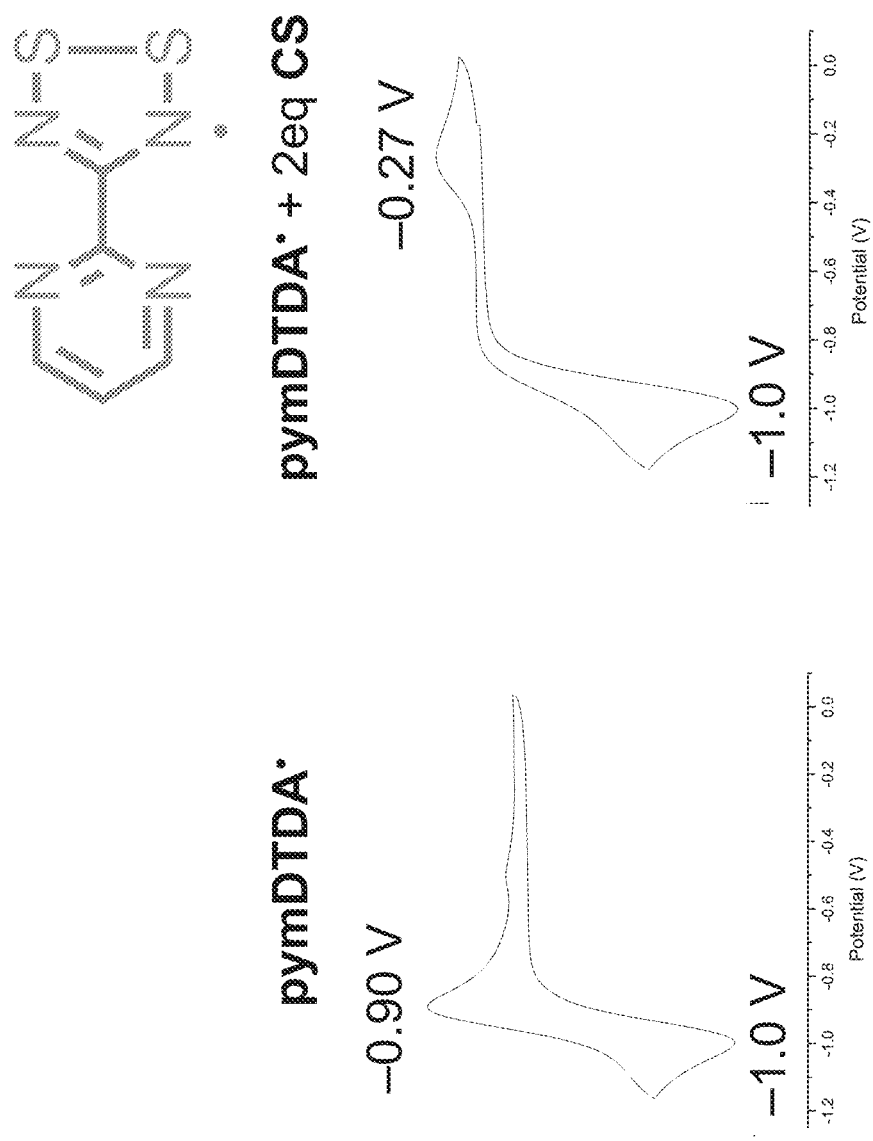
FIG. 12 depicts an exemplary cyclic voltammetry (CV) of a solution of pymDTDA. and CS. Conditions: 1.0 mM pymDTDA.+2 mM CS, 0.1 M TBABPh$_4$, $CH_2Cl_2$ degassed with $N_2$, 200 mV s$^{-1}$ scan rate, platinum wire working electrode, platinum wire counter electrode, platinum wire quasi-reference, 298 K.

The dithiadiazolide (DTDA) anions also form complexes with cyanostar (FIG. 11) as also published in Benson et al. (2016). Other examples have been tested and show the same electrochemistry response (FIG. 11B). Exactly the same electrochemistry analysis serves for evidence of complexation of the DTDA anion in FIG. 12.

Figure 13:
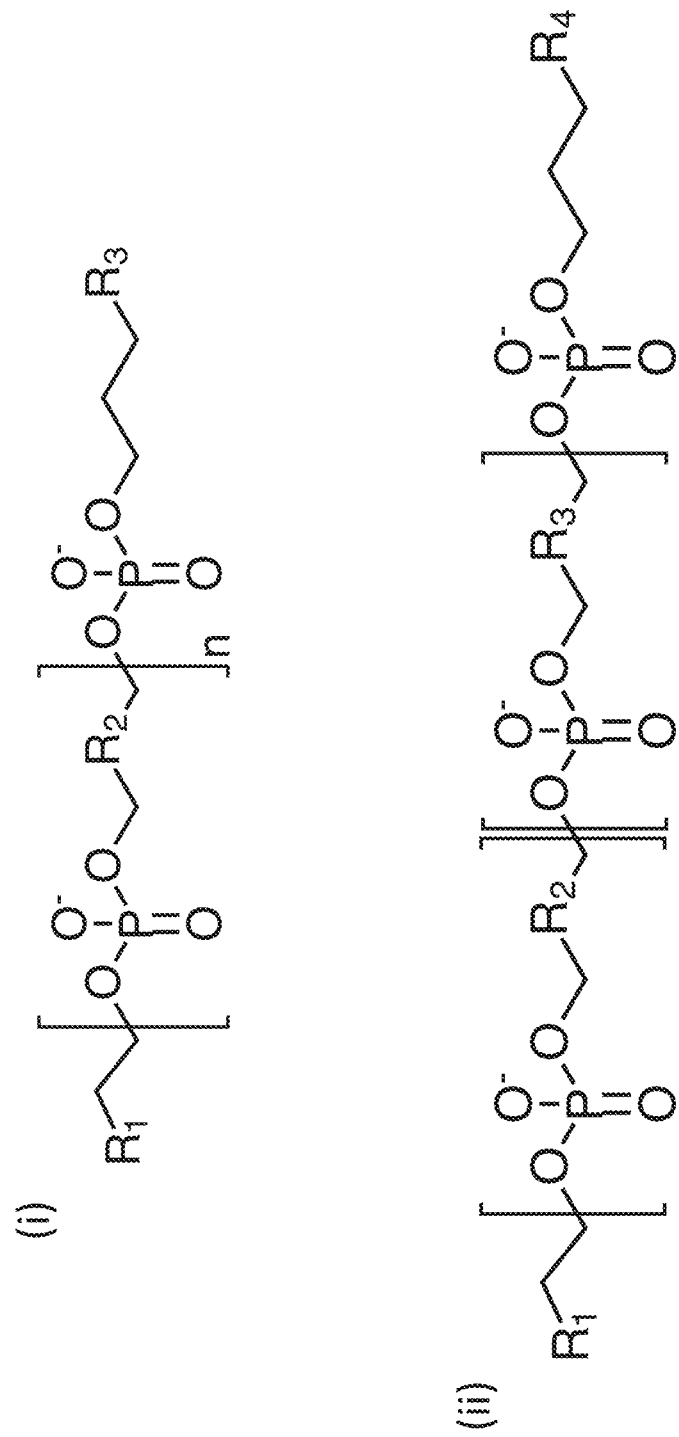
FIG. 13 depicts a symmetric polyphosphate polyanion, wherein R1, R2, and R3 can be any organic fragment (panel (i)) and a sequence specific polyphosphate polyanion, wherein R1, R2, R3 and R4 can be any organic fragment (panel (ii)). In both panels (i) and (ii), the exemplary polyphosphate polyanions can be threaded into the CS.
Figure 14:
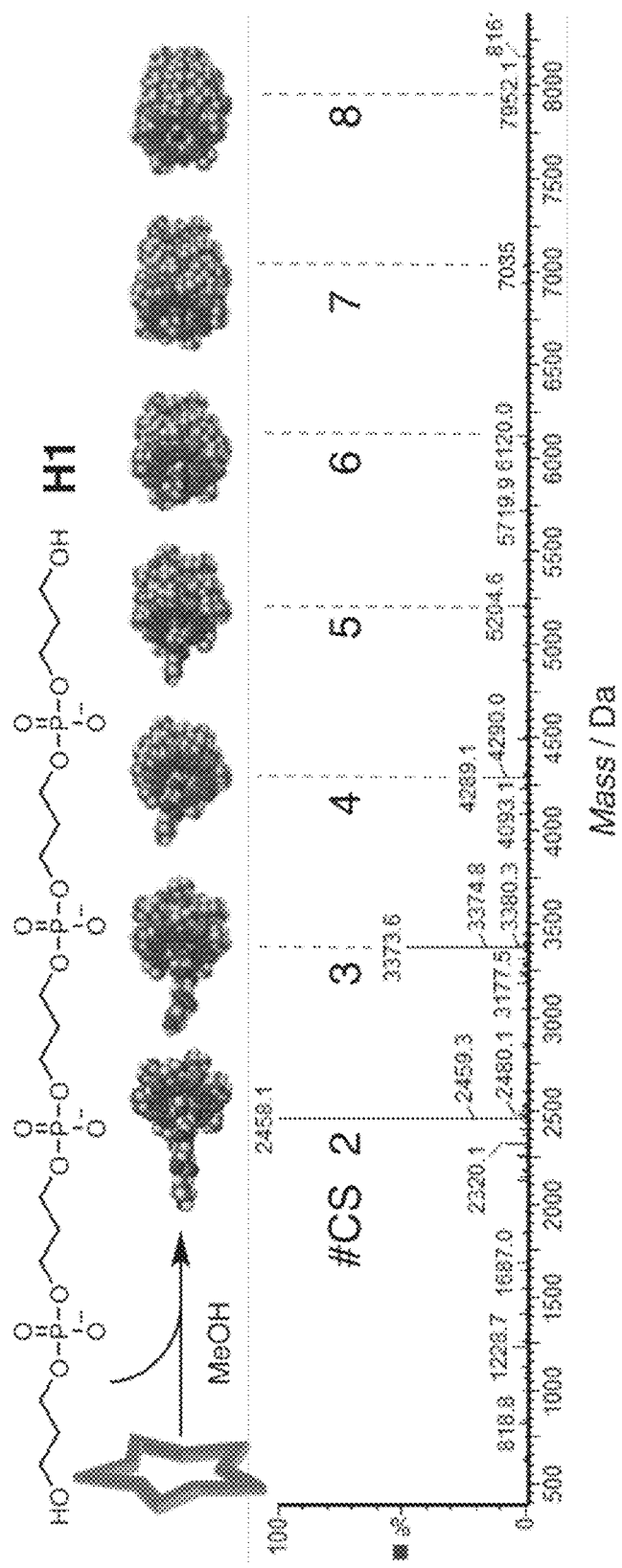
FIG. 14 depicts an exemplary charge-deconvoluted ESI-MS of poly[n]rotaxanes formed from polyphosphate compound H1 and CS.

Polyphosphates are a series of anions that can form complexes with cyanostar. We show (FIG. 13) an infinite range of polyphosphates. In principle, the sequence is infinite as defined by the linkers between each phosphate. An example of complexation with polyphosphate H1 using ESI-MS shows peaks consistent with complexes formed with variable stoichiometries (FIG. 14).

Figure 15:
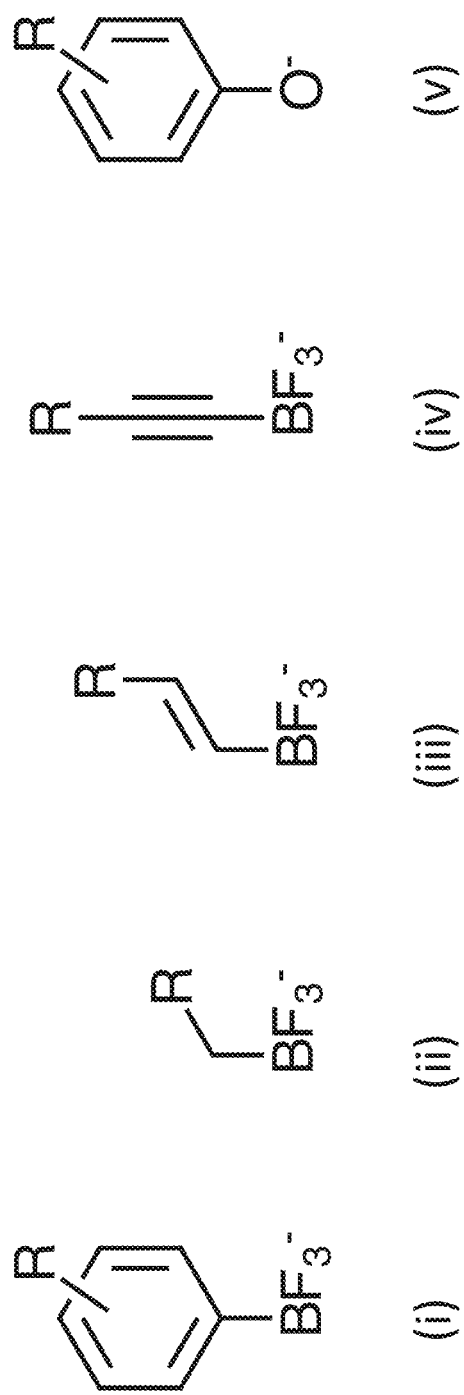
FIG. 15 depicts exemplary R—BF$_3^-$ anions (compounds (i)-(iv)) and Ar—O$^-$ anions (compound (v)) as amenable anions for complex formation with CS.

Other anions contemplated in compositions and methods of the present invention include organotrifluoroborate anions of formula, R—$BF_3^{-}$, where R can be aryl, alkyne, alkene, or alkyl) (FIG. 15, compounds (i)-(iv)) and phenoxide anions, Ar—$O^{-}$, where Ar can be any substituted aryl (FIG. 15, compound (v)).

EXAMPLES

Example 1

Studies Based Upon Computer-guided Design

Figure 1B:
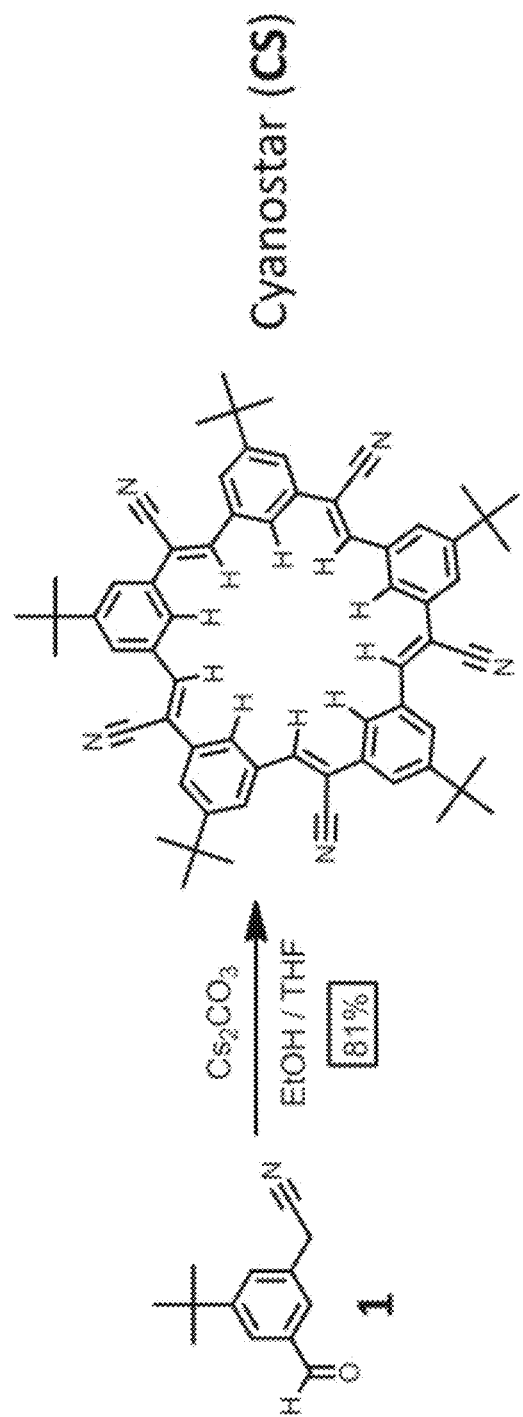
FIG. 1B illustrates an example one-pot synthesis of cyanostar.
Figure 1C:
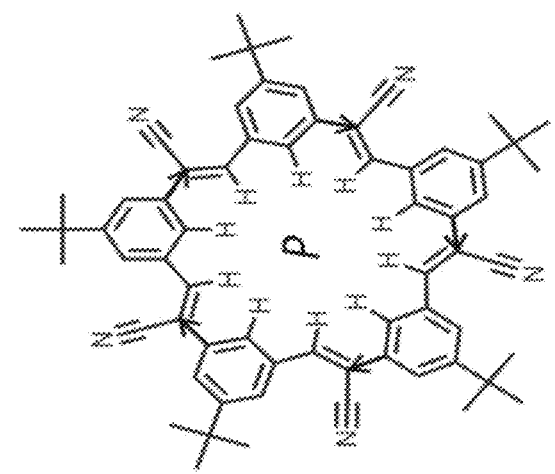
FIG. 1C illustrates a crystal structure of cyanostar. The major set of CS (M) and the minor set (P) exist in the same space. Disordered methyl groups are omitted for clarity.
Figure 1C:
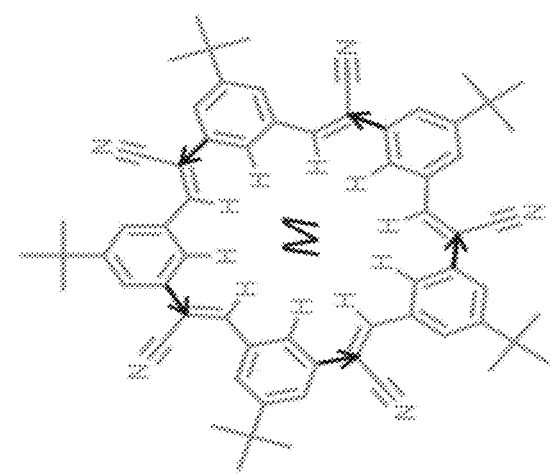
Figure 1C:
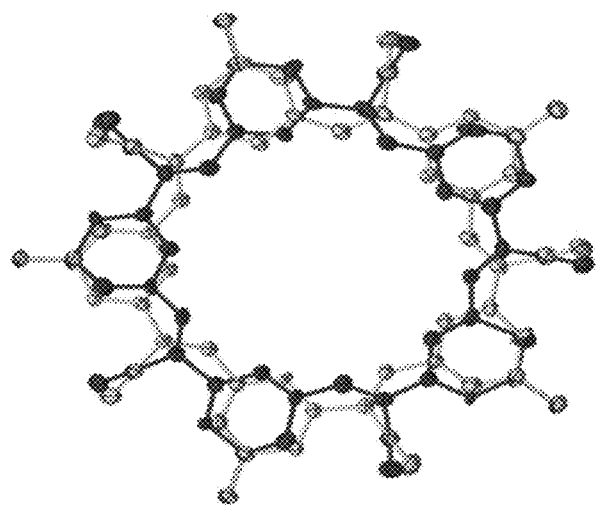
Figure 1D:
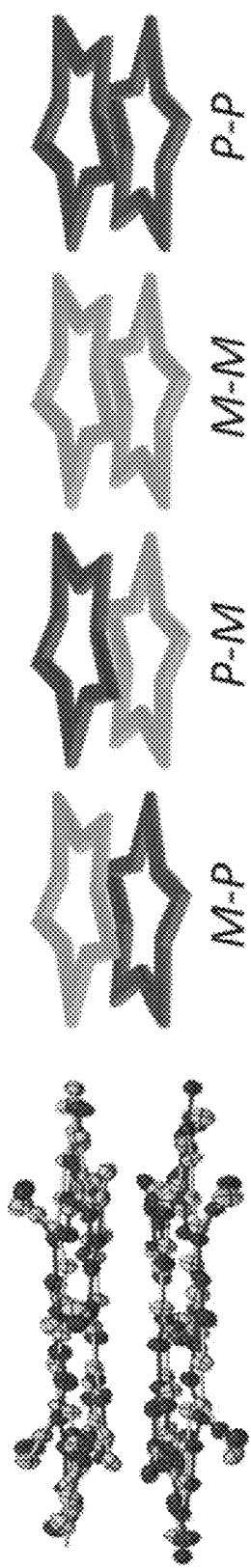
FIG. 1D illustrates a sandwich of two CSs resulting in mixture of stereoisomers.

The ability of cyanostilbene-based CH donors to stabilize anions was first verified using an acyclic receptor (see Supplementary Information). Subsequently, molecular modeling was used to evaluate if various macrocycles and their pre-macrocyclic oligomers were sufficiently pre-organized for binding and cyclization, respectively. During examination of a hexameric design, largely inspired by the isosterism between cyanostilbenes and the aryl-amides examined by Hamilton's group, it instead became apparent that the preferred turning angles were more likely to facilitate a pentameric $C_5$-symmetric structure (FIG. 1B).

Example 2

One-Pot, Multigram-scale, Macrocycle Synthesis

The synthesis (FIG. 1B) of the $C_5$-symmetric cyclo[5]-3-tert-butyl-phenylacrylonitrile macrocycle, CS, relies upon the preparation of a meta substituted difunctional phenylene (1) bearing benzylic nitrile and benzaldehyde functional groups required for the Knoevenagel self-condensation. The building block was prepared in four steps (see Supplementary Information) from a simple starting material. Gratifyingly, treatment of 1 with cesium carbonate ($Cs_2CO_3$) as the catalytic base (5 mol %) in ethanol/tetrahydrofuran (EtOH/THF) followed by a straightforward purification produced CS in 81% yield.

Achieving high yields is not usually straightforward for one-pot macrocyclizations. Zeng attributed their one-pot yields (~50%) of an aryl-amide pentamer to the build-up of intramolecular H-bonds that aid in an ordering of the growing oligomer prior to macrocyclization. While MacLachlan's campestarene takes advantage intramolecular hydrogen bonds, their near quantitative yields up to 99% can be attributed to the dynamic covalent chemistry associated with its five imine bonds that lead the system to the thermodynamic product. In the case of CS macrocycles, it appears that the base may be acting as a template or the deprotonated benzylic anion may assist intramolecular self-organization. Consistent with the importance of pre-organization in the macrocyclization, the reaction can be readily scaled up from the original 100 mg. When 12 g of 1 were self-condensed at high concentrations (40 mM 1:1 EtOH/THF), 8.9 g of CS were produced after straightforward purification with retention of the 81% yield; an outcome that is unlikely if the final ring closing step was only occurring under statistical control.

Example 3

Synthesis of Macrocycle Having Formula (I-1)

The macrocycle having Formula (I-1) was made according to the following reaction scheme:

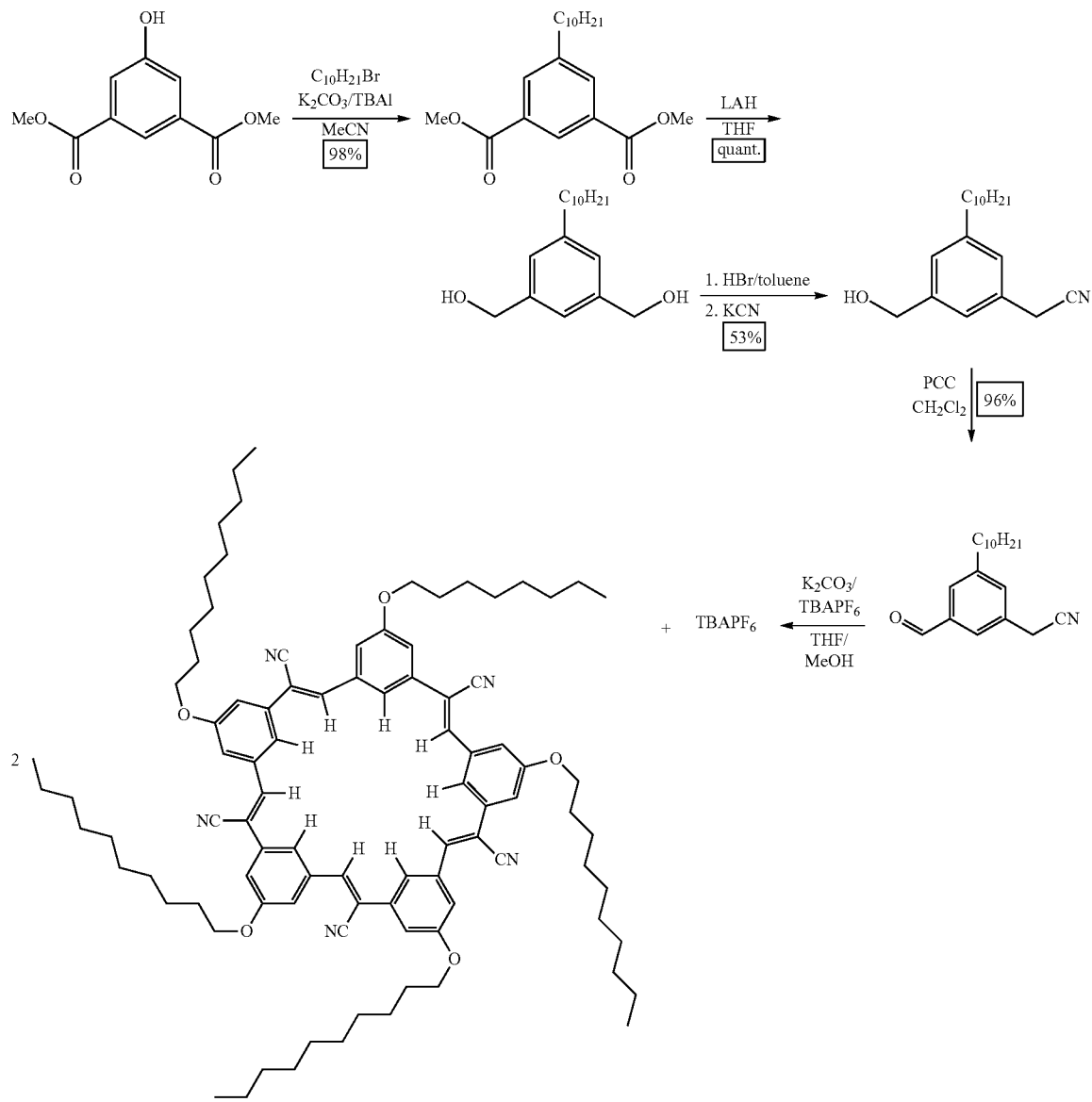

Synthesis of Dimethyl 5-(decyloxy)isophthalate

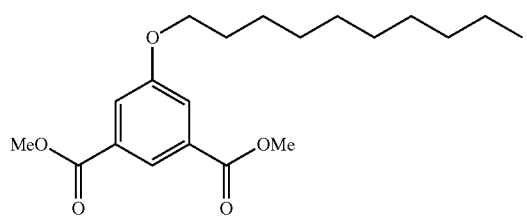 [SMILES: CCCCCCCCCCOc1cc(C(=O)OC)cc(C(=O)OC)c1]

A mixture of dimethyl 5-hydroxyisophthalate (8 g, 38.1 mmol), 1-bromodecane (8.84 g, 40 mmol), K$_2$CO$_3$ (10.5 g, 76.1 mmol) and KI (200 mg, 1.2 mmol) in MeCN (200 mL) was refluxed for 6 h. MeCN was removed in vacuo, extracted with EtOAc, washed with brine, dried with MgSO$_4$ and concentrated in vacuo to give a white solid product (13.1 g, 37.3 mmol, 98% yield). $^1$H NMR (400 MHz, CDCl$_3$) δ=8.26 (s, 1H), 7.74 (d, J=1.1 Hz, 2H), 4.03 (t, J=6.3 Hz, 2H), 3.94 (s, 6H), 1.80 (m, 2H), 1.48 (m, 2H) 1.28 (m, 12H), 0.88 (t, J=6.3 Hz, 3H).

Synthesis of (5-(Decyloxy)-1,3-phenylene)dimethanol

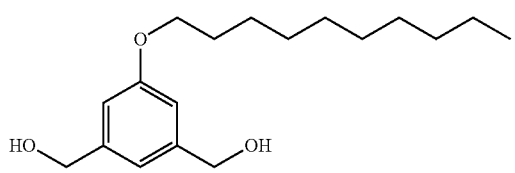 [SMILES: CCCCCCCCCCOc1cc(CO)cc(CO)c1]

To a suspension of LAH (3 g, 77.9 mmol) in THF (100 mL) was dropwise added dimethyl 5-(decyloxy)isophthalate (13 g, 37.1 mmol) in THF (100 mL) and stirred for 2 h. 3 M HCl solution was dropwise added to acidify the solution and stirred for 1 h. The resulting mixture was extracted with EtOAc, washed with brine, dried with MgSO$_4$ and concentrated in vacuo to give a grey solid product (10.95 g, 37.1 mmol, quantitative yield). $^1$H NMR (500 MHz, CDCl$_3$) δ=6.93 (s, 1H), 6.85 (s, 2H), 4.67 (s, 4H), 3.97 (t, J=6.4 Hz, 2H), 1.78 (m, 2H), 1.68 (br, 2H), 1.45 (m, 2H), 1.28 (m, 12H), 0.88 (t, J=6.8 Hz, 3H).

Synthesis of 2-(3-(Decyloxy)-5-(hydroxymethyl)phenyl)acetonitrile

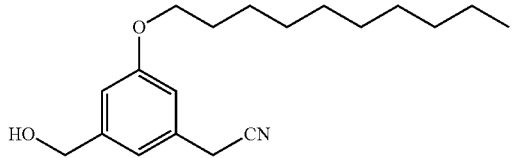 [SMILES: CCCCCCCCCCOc1cc(CO)cc(CC#N)c1]

To a solution of (5-(decyloxy)-1,3-phenylene)dimethanol (5 g, 16.98 mmol) in toluene (100 mL) was added 47-49% aqueous solution of HBr (4.3 mL, 38 mmol) and stirred at 70° C. for 4 h. The reaction mixture was cooled under ice bath and neutralized with Na$_2$CO$_3$ solution. The organic phase was collected and the aqueous layer was further extracted with EtOAc. Organic layers were combined and dried with MgSO$_4$, filtered then concentrated under vacuum. The resulting compound was dissolved in THF (50 mL) and water (50 mL). KCN (2.2 g, 33.96 mmol) was added and stirred at 60° C. overnight. After cooling to room temperature, THF was removed in vacuo. The mixture was extracted with EtOAc and the organic phase was dried with MgSO$_4$, filtered and the solvents were removed in vacuo. Column chromatography on silica gel with hexane:EtOAc=2:1 resulted a white solid product (2.74 g, 9.03 mmol, 53% yield). $^1$H NMR (400 MHz, CDCl$_3$) d=6.88 (s, 1H), 6.87 (s, 1H), 6.78 (s, 1H), 4.67 (d, J=5.9 Hz, 2H), 3.96 (t, J=6.6 Hz, 2H), 3.71 (s, 2H), 1.78 (m, 3H), 1.45 (m, 2H), 1.28 (m, 12H), 0.88 (t, J=7.0 Hz, 3H).

Synthesis of 2-(3-(Decyloxy)-5-formylphenyl)acetonitrile

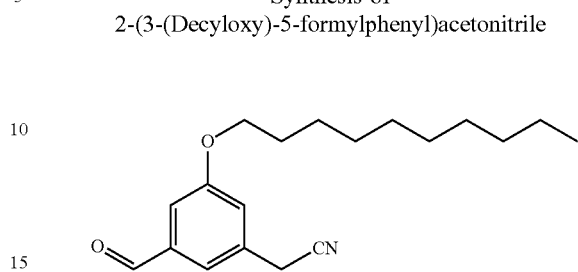

PCC (1.07 g, 4.94 mmol) and silica gel (5 g) were mixed well using a mortar and pestle and suspended in CH$_2$Cl$_2$ (40 mL). A solution of 2-(3-(decyloxy)-5-(hydroxymethyl)phenyl)acetonitrile(1 g, 3.30 mmol) in CH$_2$Cl$_2$ (15 mL) was dropwise added while stirring. The reaction mixture was stirred at room temperature for 3 h and filtered through a short silica gel column and washed with CH$_2$Cl$_2$:EtOAc=9:1 to give a white solid product (950 mg, 3.15 mmol, 96% yield). $^1$H NMR (400 MHz, CDCl$_3$) δ=9.97 (s, 1H), 7.40 (s, 1H), 7.34 (s, 1H), 7.15 (s, 1H), 4.03 (t, J=6.6 Hz, 2H), 3.80 (s, 2H), 1.81 (m, 2H), 1.47 (m, 2H), 1.28 (m, 12H), 0.88 (t, J=7.0 Hz, 3H). $^{13}$C NMR (100 MHz, CDCl$_3$) δ=191.2, 160.2, 138.3, 132.3, 121.8, 120.8, 117.1, 113.0, 68.5, 31.8, 29.4, 29.20, 29.17, 28.9, 25.8, 23.3, 22.5, 14.0

Example 4

2((I-1)).TBAPF$_6$ Complex Formation

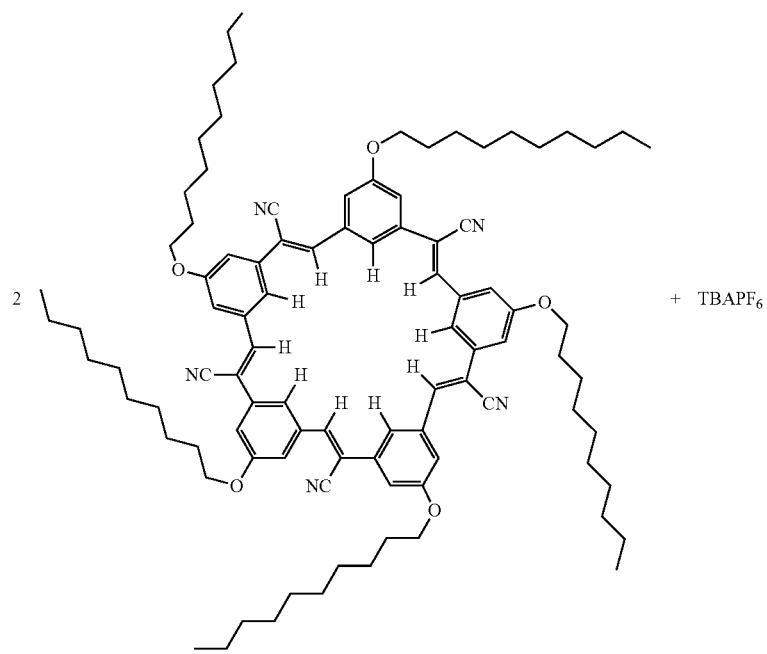 [SMILES: CCCCCCCCCCOc1cc2cc(c1)/C(C#N)=C/c1cc(OCCCCCCCCCC)cc(c1)/C(C#N)=C/c1cc(OCCCCCCCCCC)cc(c1)/C(C#N)=C/c1cc(OCCCCCCCCCC)cc(c1)/C(C#N)=C/c1cc(OCCCCCCCCCC)cc(c1)/C(C#N)=C/2]

To a solution of 2-(3-(decyloxy)-5-formylphenyl)acetonitrile (100 mg, 0.332 mmol) and TBAPF$_6$ (257 mg, 0.664 mmol) in THF (50 mL) and MeOH (50 mL) added a saturated solution of $K_2CO_3$ in MeOH (0.5 mL) and refluxed overnight. The solvents were removed in vacuo. Column chromatography on silica gel with hexanes:$CH_2Cl_2$:EtOAc=45:45:10 resulted a yellow solid product (53 mg, 0.017 mmol, 50% yield). $^1$H NMR (500 MHz, $CDCl_3$) δ=7.82 (s, 10H), 7.52 (s, 10H), 7.25 (s, 10H), 7.03 (s, 10H), 4.09 (s, 20H), 2.98 (m, 8H), 1.87 (m, 20H), 1.58 (m, 20H), 1.51 (m, 8H), 1.44-1.32 (m, 128H), 0.95 (t, J=7.3 Hz, 8H), 0.92 (t, J=7.3 Hz, 30H).

Example 5

Synthesis of Macrocycle Having Formula (I-2)

The macrocycle having Formula (I-2) was made according to the following reaction scheme:

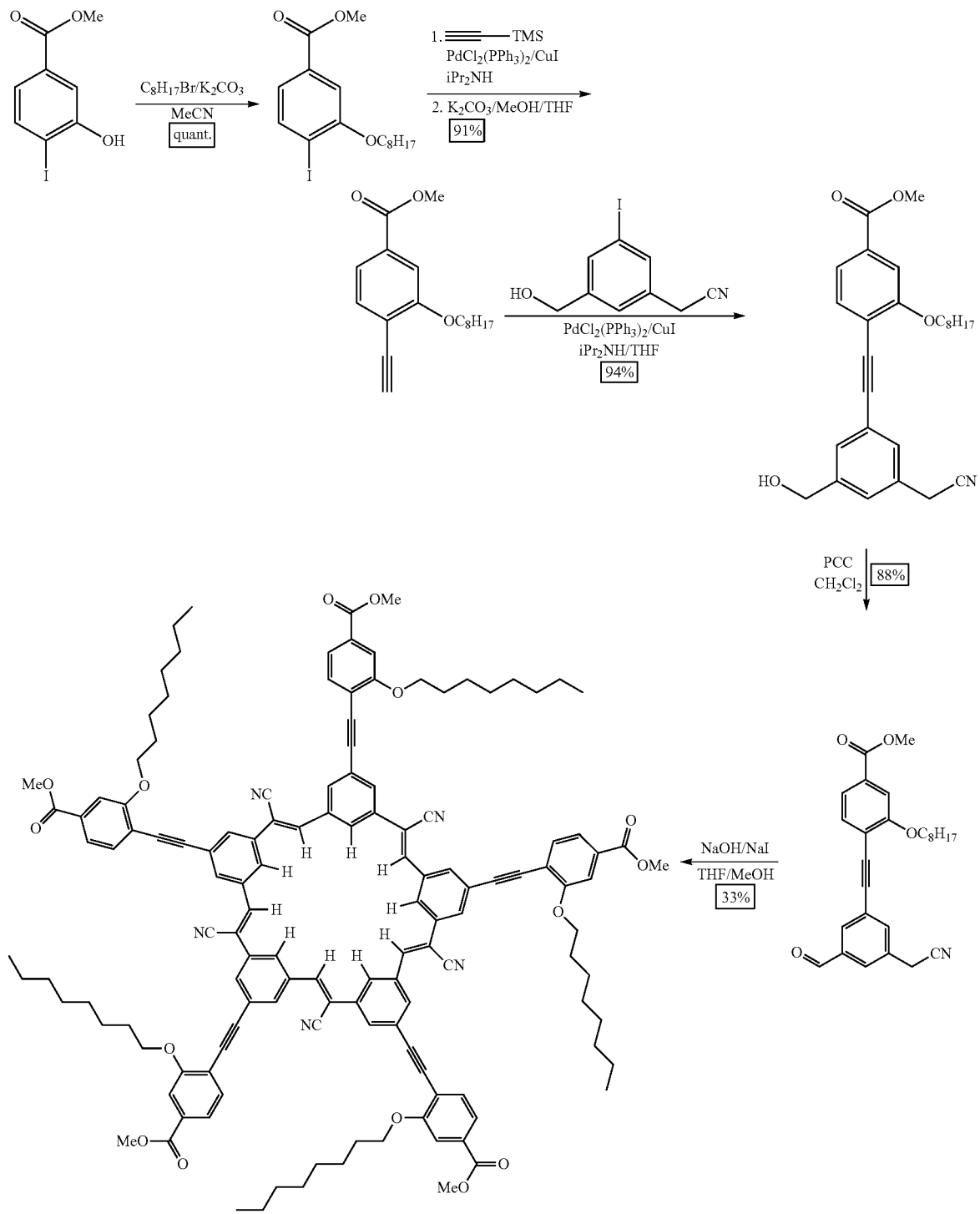

Synthesis of Methyl 4-iodo-3-(octyloxy)benzoate

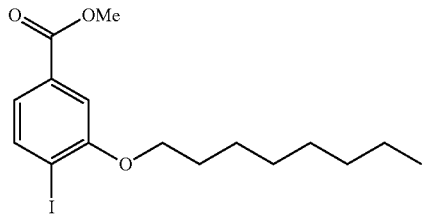 [SMILES: CCCCCCCCOc1cc(C(=O)OC)ccc1I]

A mixture of methyl 3-hydroxy-4-iodobenzoate (2 g, 7.19 mmol), 1-bromooctane (1.53 g, 7.9 mmol), K$_2$CO$_3$ (2 g, 14.4 mmol) and KI (120 mg, 0.72 mmol) in MeCN (100 mL) was refluxed for 5 h. MeCN was removed in vacuo, extracted with EtOAc, washed with brine, dried with MgSO$_4$ and concentrated in vacuo. Column chromatography on silica gel with hexane:EtOAc=9:1 resulted a white solid product (2.81 g, 7.2 mmol, quantitative yield). $^1$H NMR (400 MHz, CDCl$_3$) δ=7.84 (d, J=8.2 Hz, 1H), 7.41 (s, 1H, 7.35 (d, J=7.8 Hz, 1H), 4.07 (t, J=6.3 Hz, 2H), 3.91 (s, 3H), 1.85 (m, 2H), 1.53 (m, 2H), 1.30 (m, 8H), 0.89 (t, J=6.6 Hz, 3H). $^{13}$C NMR (100 MHz, CDCl$_3$) δ=165.9, 157.3, 138.9, 131.0, 122.6, 111.6, 93.0, 69.0, 51.9, 31.5, 28.97, 28.94, 28.7, 25.8, 22.4, 13.8.

Synthesis of Methyl 4-ethynyl-3-(octyloxy)benzoate

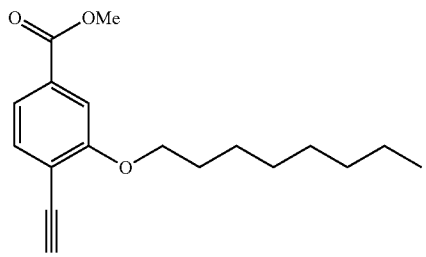 [SMILES: C#Cc1ccc(C(=O)OC)cc1OCCCCCCCC]

A solution of methyl 4-iodo-3-(octyloxy)benzoate (1.33 g, 3.41 mmol) and diisopropylamine (2 mL, 13.6 mmol) in THF (50 mL) was degassed with argon for 20 min. PdCl$_2$(PPh$_3$)$_2$ (47 mg, 0.068 mmol), CuI (32 mg, 0.17 mmol) and TMS-acetylene were added and stirred under argon atmosphere for 5 h. The reaction mixture was filtered and the solvent was removed in vacuo. Column chromatography on silica gel with hexane:EtOAc=9:1 resulted methyl 3-(octadecyloxy)-4-((trimethylsilyl)ethynyl)benzoate as a brown oil (1.24 g, 3.4 mmol, quantitative yield). This intermediate methyl 3-(octadecyloxy)-4-((trimethylsilyl)ethynyl)benzoate(600 mg, 1.66 mmol) was dissolved in MeOH (20 mL) and a saturated solution of K$_2$CO$_3$ in MeOH (2 mL) was added and stirred for 2 h. The solvent was removed in vacuo and the resulting crude mixture was suspended in CH$_2$Cl$_2$ and filtered through a pad of Celite to give a brown oil product (435 mg, 1.51 mmol, 91% yield). $^1$H NMR (400 MHz, CDCl$_3$) δ=7.57 (dd, J=7.8, 1.2 Hz, 1H), 7.53 (d, J=1.2 Hz, 1H), 7.49 (d, J=7.8 Hz, 1H), 4.09 (t, J=6.6 Hz, 2H), 3.92 (s, 3H), 3.39 (s, 1H), 1.85 (m, 2H), 1.50 (m, 2H), 1.29 (m, 8H), 0.89 (t, J=7.0 Hz, 3H). $^{13}$C NMR (100 MHz, CDCl$_3$) δ=166.4, 160.0, 133.7, 131.3, 121.2, 116.3, 112.3, 83.6, 79.3, 68.9, 52.2, 31.7, 29.2, 29.1, 28.9, 25.8, 22.6, 14.0

Synthesis of Methyl 4-((3-(cyanomethyl)-5-(hydroxymethyl)phenyl)ethynyl)-3-(octyloxy)benzoate

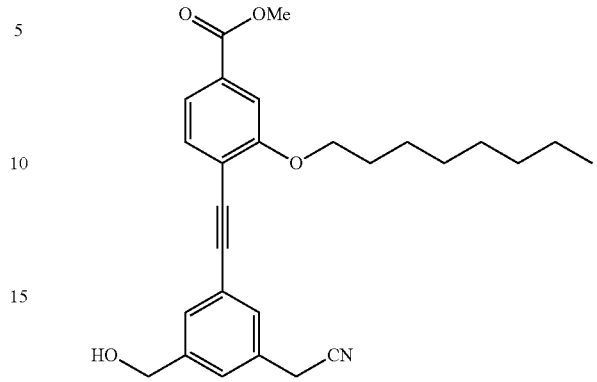

A solution of methyl 4-ethynyl-3-(octyloxy)benzoate (1 g, 3.47 mmol), 2-(3-(hydroxymethyl)-5-iodophenyl)acetonitrile and diisopropylamine (0.7 mL, 4.8 mmol) in THF (50 mL) was degassed with argon for 20 min. PdCl$_2$(PPh$_3$)$_2$ (17 mg, 0.024 mmol) and CuI (12 mg, 0.06 mmol) was added and stirred at 70° C. for 5 h. After cooling to room temperature, the reaction mixture was filtered and the solvent was removed in vacuo. Column chromatography on silica gel with CH$_2$Cl$_2$:EtOAc=9:1 resulted in a white solid product (1.28 g, 2.95 mmol, 94% yield). $^1$H NMR (400 MHz, CDCl$_3$) δ=7.61 (d, J=7.8 Hz, 1H), 7.55 (s, 1H), 7.52 (d, J=8.0 Hz, 1H), 7.50 (s, 1H), 7.43 (s, 1H), 7.35 (s, 1H), 4.73 (d. J=5.9 Hz, 2H), 4.12 (t, J=6.6 Hz, 2H), 3.93 (s, 3H), 3.76 (s, 2H), 1.89 (m, 2H), 1.80 (t, J=5.9 Hz, 1H), 1.65 (m, 2H), 1.43-1.27 (m, 8H), 0.86 (t, J=6.6 Hz, 3H). $^{13}$C NMR (100 MHz, CDCl$_3$) δ=166.4, 159.3, 142.4, 132.8, 130.8, 130.3, 129.7, 129.2, 126.03, 124.1, 121.3, 117.4, 117.0, 112.2, 94.9, 86.1, 68.7, 63.8, 52.1, 31.6, 29.1, 28.9, 25.8, 23.1, 22.4, 13.9.

Synthesis of Methyl 4-((3-(cyanomethyl)-5-formylphenyl)ethynyl)-3-(octyloxy)benzoate

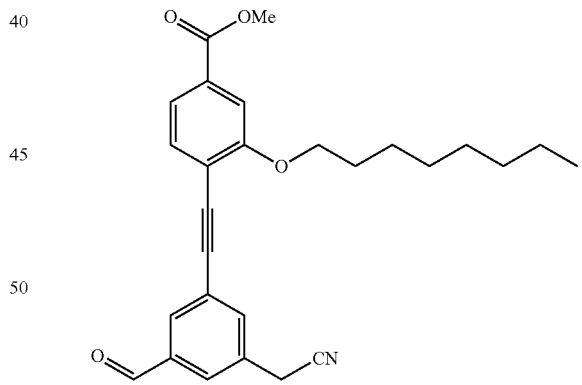

PCC (920 mg, 4.26 mmol) and silica gel (5 g) were mixed well using a mortar and pestle and suspended in CH$_2$Cl$_2$ (50 mL). A solution of methyl 4-((3-(cyanomethyl)-5-(hydroxymethyl)phenyl)ethynyl)-3-(octyloxy)benzoate (1.23 g, 2.84 mmol) in CH$_2$Cl$_2$ (30 mL) was dropwise added while stirring. The reaction mixture was stirred at room temperature overnight and filtered through a short silica gel column and washed with CH$_2$Cl$_2$ to give a white solid product (1.08 g, 2.50 mmol, 88% yield). $^1$H NMR (300 MHz, CDCl$_3$) δ=10.03 (s, 1H), 7.99 (s, 1H), 7.82 (s, 1H), 7.77 (s, 1H), 7.63 (dd, J=8.0, 1.4 Hz, 1H), 7.57 (d, J=1.1 Hz, 1H), 7.54 (d, J=7.7 Hz, 1H), 4.13 (t, J=6.6 Hz, 2H), 3.94 (s, 3H), 3.85 (s, 2H), 1.90 (m, 2H), 1.58 (m, 2H), 1.40-1.27 (m, 8H), 0.85 (t, J=6.6 Hz, 3H).

Synthesis of (Methyl 4-ethynyl-3-(octyloxy)benzoate)₅-cyanostar [Formula (I-2)]

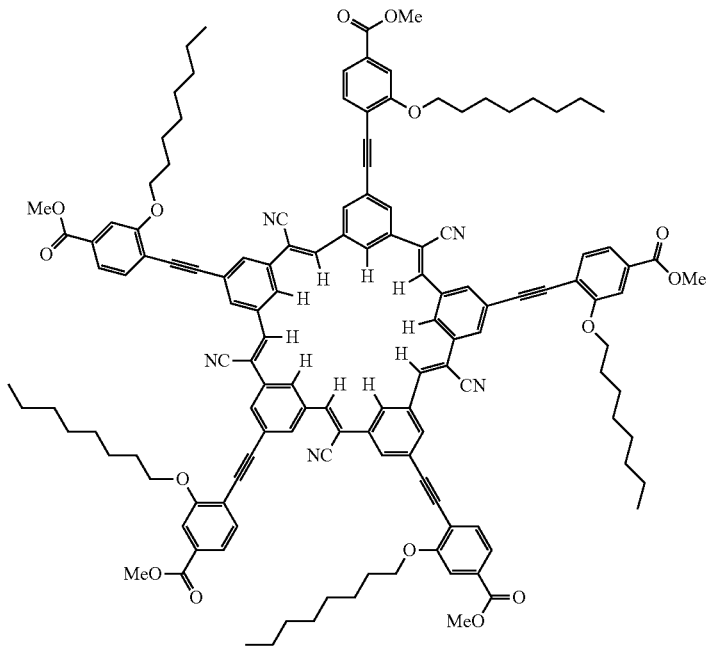 [SMILES: CCCCCCCCOc1cc(C(=O)OC)ccc1C#Cc1cc2cc(c1)/C(C#N)=C/c1cc(C#Cc3ccc(C(=O)OC)cc3OCCCCCCCC)cc(c1)/C(C#N)=C/c1cc(C#Cc3ccc(C(=O)OC)cc3OCCCCCCCC)cc(c1)/C(C#N)=C/c1cc(C#Cc3ccc(C(=O)OC)cc3OCCCCCCCC)cc(c1)/C(C#N)=C/c1cc(C#Cc3ccc(C(=O)OC)cc3OCCCCCCCC)cc(c1)/C(C#N)=C/2]

To a solution of methyl 4-((3-(cyanomethyl)-5-formylphenyl)ethynyl)-3-(octyloxy)benzoate(100 mg, 0.232 mmol), NaOH (2 mg, 0.046 mmol) and NaI (35 mg, 0.23 mmol) in MeOH (12 mL) and THF (12 mL) was stirred overnight at room temperature. Solvents were removed in vacuo. Column chromatography on silica gel with CH$_2$Cl$_2$: EtOAc=9:1 resulted in a yellow solid product (32 mg, 0.015 mmol, 33% yield). $^1$H NMR (400 MHz, CD$_2$Cl$_2$) δ=8.38 (s, 5H), 7.75 (s, 5H), 7.65 (s, 5H), 7.49-7.40 (m, 15H), 4.04 (t, J=6.3 Hz, 10H), 3.84 (s, 15H), 1.92 (m, 10H), 1.54 (m, 10H), 1.42 (m, 10H), 1.32-1.24 (m, 40H), 0.80 (t, J=6.6 Hz, 15H).

Example 6

Synthesis of Macrocycle Having Formula (I-6)

The macrocycle having Formula (I-6) was made according to the following reaction scheme:

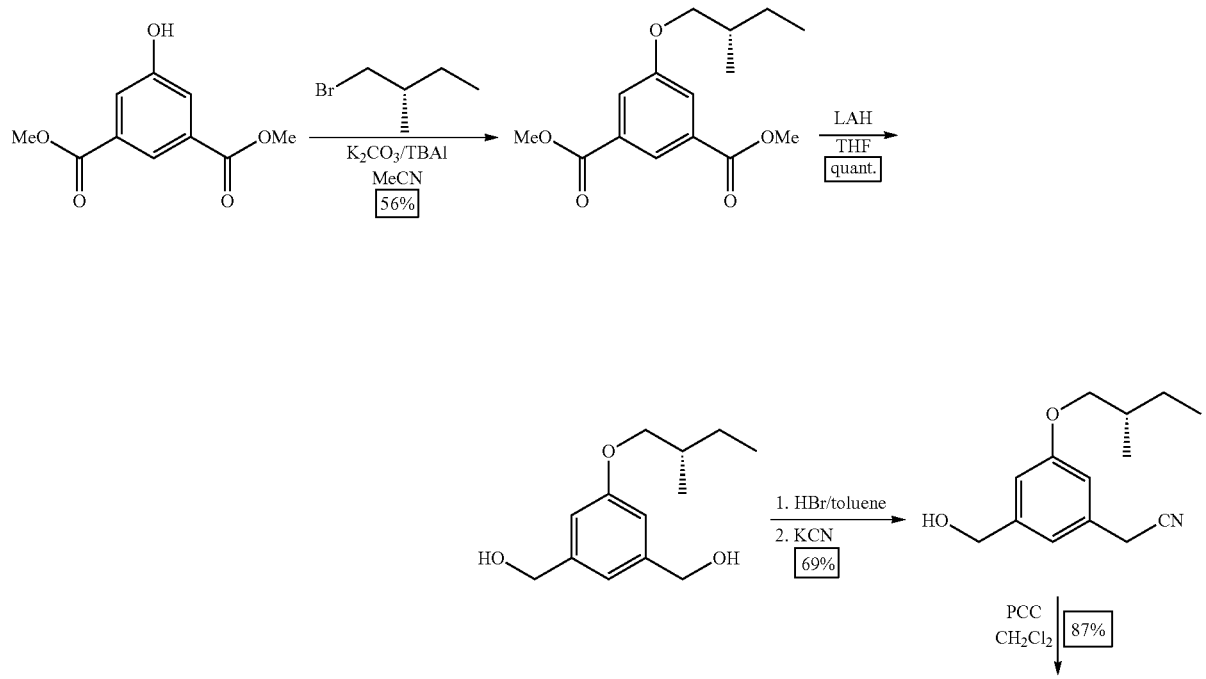

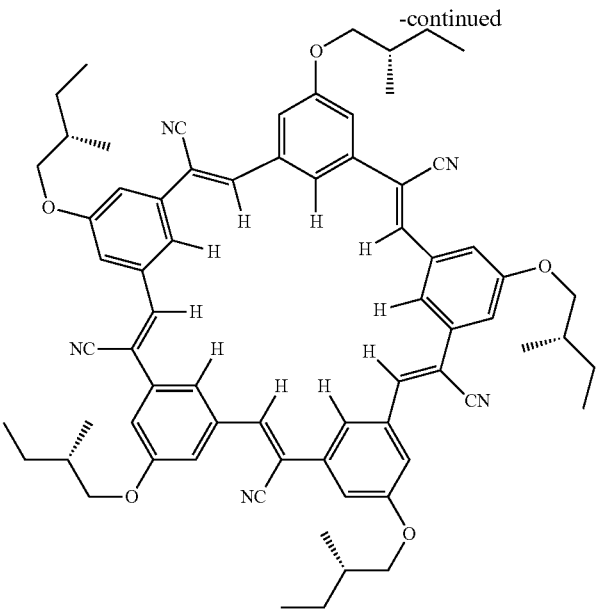
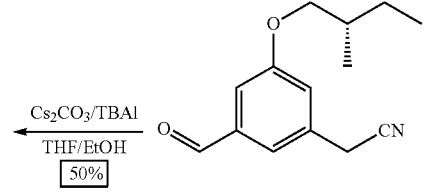

Synthesis of Dimethyl (S)-5-(2-methylbutoxy)isophthalate

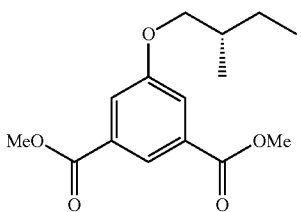 [SMILES: CC[C@H](C)COc1cc(C(=O)OC)cc(C(=O)OC)c1]

A mixture of dimethyl 5-hydroxyisophthalate (2.78 g, 13.24 mmol), (S)-(+)-1-bromo-2-methylbutane (2 g, 13.24 mmol), $K_2CO_3$ (5.5 g, 40 mmol) and TBAI (147 mg, 0.397 mmol) in MeCN (40 mL) stirred at 80° C. in a sealed tube for 36 h. MeCN was removed in vacuo, extracted with EtOAc, washed with brine, dried with $MgSO_4$ and concentrated in vacuo. Column chromatography on silica gel with hexane:EtOAc=9:1 resulted a colorless oil product (2.06 g, 7.35 mmol, 56% yield) $^1$H NMR (400 MHz, $CDCl_3$) δ=8.26 (t, J=1.2 Hz, 1H), 7.74 (d, J=1.2 Hz, 1H), 3.94 (s, 6H), 3.92-3.80 (m, 2H), 1.90 (m, 1H), 1.58 (m, 1H), 1.29 (m, 1H), 1.03 (d, J=6.6 Hz, 3H), 0.96 (t, J=7.4 Hz, 3H). $^{13}$C NMR (100 MHz, $CDCl_3$) δ=166.0, 159.2, 131.5, 122.5, 119.6, 73.23, 52.2, 34.5, 25.9, 16.3, 11.15.

Synthesis of (S)-(5-(2-Methylbutoxy)-1,3-phenylene)dimethanol

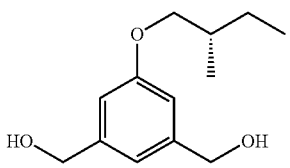 [SMILES: CC[C@H](C)COc1cc(CO)cc(CO)c1]

To a suspension of LAH (1.7 g, 44.8 mmol) in THF (50 mL) was dropwise added dimethyl dimethyl (S)-5-(2-methylbutoxy)isophthalate (2 g, 7.13 mmol) in THF (30 mL) and stirred for 4 h. 3 M HCl solution was dropwise added to acidify the solution and stirred for 1 h. The resulting mixture was extracted with EtOAc, washed with brine, dried with $MgSO_4$ and concentrated in vacuo to give a colorless oil product (1.6 g, 7.13 mmol, quantitative yield). $^1$H NMR (500 MHz, $CDCl_3$) δ=6.92 (s, 1H), 6.85 (s, 1H), 4.67 (s, 4H), 3.85-3.73 (m, 2H), 1.85 (m, 1H), 1.57 (m, 1H), 1.29 (m, 1H), 1.02 (d, J=6.6 Hz, 3H), 0.95 (t, J=7.8 Hz, 3H). $^{13}$C NMR (100 MHz, $CDCl_3$) δ=159.6, 142.6, 117.3, 112.1, 72.9, 64.8, 34.7, 26.1, 16.5, 11.3.

Synthesis of (S)-2-(3-(Hydroxymethyl)-5-(2-methylbutoxy)phenyl)acetonitrile

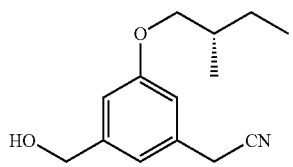 [SMILES: CC[C@H](C)COc1cc(CO)cc(CC#N)c1]

To a solution of (S)-(5-(2-methylbutoxy)-1,3-phenylene)dimethanol (1.6 g, 7.13 mmol) in toluene (120 mL) was added 47-49% aqueous solution of HBr (1.6 mL, 14.3 mmol) and stirred at 80° C. for 3 h. The reaction mixture was cooled under ice bath and neutralized with $Na_2CO_3$ solution. The organic phase was collected and the aqueous layer was further extracted with EtOAc. Organic layers were combined and dried with $MgSO_4$, filtered then concentrated under vacuum. The resulting compound was dissolved in THF (30 mL), MeOH (30 mL) and water (20 mL). KCN (930 mg, 14.3 mmol) was added and stirred at 80° C. for 4 h. After cooling to room temperature, THF was removed in vacuo. The mixture was extracted with EtOAc and the organic phase was dried with $MgSO_4$, filtered and the solvents were removed in vacuo. Column chromatography on silica gel with CH$_2$Cl$_2$:EtOAc=95:5 to 9:1 resulted a white solid product (1.15 g, 4.93 mmol, 69% yield). $^1$H NMR (500 MHz, CDCl$_3$) δ=6.90 (s, 2H), 6.81 (s, 1H), 4.70 (d, J=5.9 Hz, 2H), 3.86-3.76 (m, 2H), 3.73 (s, 2H), 1.89 (m, 1H), 1.59 (m, 1H), 1.29 (m, 1H), 1.04 (d, J=6.8 Hz, 3H), 0.97 (t, J=7.3 Hz, 3H). $^{13}$C NMR (125 MHz, CDCl$_3$) δ=159.8, 143.5, 131.1, 118.0, 117.8, 113.1, 112.0, 72.8, 64.2, 34.5, 25.9, 23.3, 16.3, 11.1.

Synthesis of (S)-2-(3-Formyl-5-(2-methylbutoxy) phenyl)acetonitrile

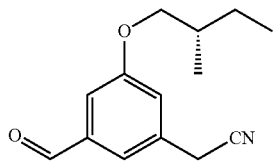 [SMILES: CC[C@H](C)COc1cc(C=O)cc(CC#N)c1]

PCC (700 mg, 3.21 mmol) and silica gel (4 g) were mixed well using a mortar and pestle and suspended in CH$_2$Cl$_2$ (30 mL). A solution of (S)-2-(3-(hydroxymethyl)-5-(2-methylbutoxy)phenyl)acetonitrile(500 mg, 2.14 mmol) in CH$_2$Cl$_2$ (10 mL) was dropwise added while stirring. The reaction mixture was stirred at room temperature for 3 h and filtered through a short silica gel column and washed with CH$_2$Cl$_2$: EtOAc=95:5 to give a colorless oil product (430 mg, 1.86 mmol, 87% yield). $^1$H NMR (400 MHz, CDCl$_3$) δ=9.97 (s, 1H), 7.40 (s, 1H), 7.35 (s, 1H), 7.16 (s, 1H), 3.91-3.81 (m, 2H), 3.80 (s, 2H), 1.90 (m, 1H), 1.58 (m, 1H), 1.31 (s, 1H), 1.04 (d, J=6.6 Hz, 3H), 0.96 (t, J=7.8 Hz, 3H). $^{13}$C NMR (100 MHz, CDCl$_3$) δ=191.1, 160.2, 138.1, 132.3, 121.6, 120.7, 117.1, 112.9, 73.1, 34.4, 25.8, 23.1, 16.2, 11.0.

Synthesis of ((S)-2-methylbutoxy)$_5$-cyanostar [Formula (I-6)]

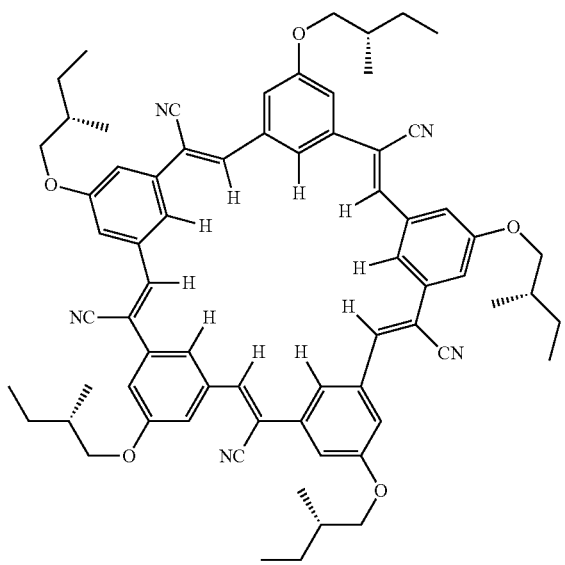 [SMILES: CC[C@H](C)COc1cc2cc(c1)/C(C#N)=C/c1cc(OC[C@@H](C)CC)cc(c1)/C(C#N)=C/c1cc(OC[C@@H](C)CC)cc(c1)/C(C#N)=C/c1cc(OC[C@@H](C)CC)cc(c1)/C(C#N)=C/c1cc(OC[C@@H](C)CC)cc(c1)/C(C#N)=C/2]

Cs$_2$CO$_3$ (16 mg) was suspended in EtOH (13 mL) and stirred for 30 minutes to promote dissolution. Once dissolved, TBAI (188 mg, 0.51 mmol) and THF (10 mL) were added followed by (S)-2-(3-formyl-5-(2-methylbutoxy)phenyl)acetonitrile (117 mg, 0.51 mmol) as solutions in THF (3 mL). The solution was kept in the dark and stirred for 24 hours at room temperature. The resulting light yellow suspension was concentrated to dryness and separated over SiO$_2$ (CHCl$_3$:hexanes=9:1) to yield a light yellow solid product (51 mg, 0.048 mmol, 47% yield). $^1$H NMR (400 MHz, CDCl$_3$) δ=7.94 (s, 5H), 7.55 (s, 5H), 7.29 (s, 5H), 7.27 (s, 5H), 3.99-3.88 (m, 10H), 1.96 (m, 5H), 1.66 (m, 5H), 1.36 (m, 5H), 1.10 (d, J=6.6 Hz, 15H), 1.01 (t, J=7.8 Hz, 15H).

Example 7

Synthesis of Macrocycle Having Formula (I-7)

Synthesis of 2-(3-(hydroxymethyl)-5-((triisopropylsilyl)ethynyl)phenyl)acetonitrile (TIPS-hydroxyl-CN)

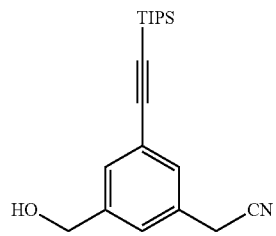

2-(3-(Hydroxymethyl)-5-iodophenyl)acetonitrile (500 mg, 1.83 mmol) was dissolved in THF (20 mL) and degassed with argon. PdCl$_2$(PPh$_3$)$_2$(38 mg), CuI (17 mg), diisopropylamine (1.3 mL), and (triisopropylsilyl)acetylene (820 μL) were then added in succession and the flask was purged with argon. The solution was stirred at room temperature for 12 hours. The resulting solution was filtered over Celite, washed with THF, and chromatographed over SiO$_2$ (10-15% acetone/hexanes) to yield TIPS-hydroxyl-CN (565 mg, 94%) as a tan solid. $^1$H NMR (500 MHz, CDCl$_3$) S=7.40 (s, 1H), 7.31 (s, 1H), 7.24 (s, 1H), 4.63 (d, 0.1=5.4 Hz, 2H), 3.69 (s, 2H), 2.90 (br s, 1H), 1.13 (m, 21H). $^{13}$C NMR (125 MHz, CDCl$_3$) δ=142.29, 130.27, 130.26, 129.83, 126.06, 124.47, 117.59, 105.89, 91.93, 63.91, 23.22, 18.63, 11.24. HR-ESI-MS: C$_{20}$H$_{30}$ONSi [M+H$^+$]; Calculated: 328.2091, Found: 328.2086.

Synthesis of 2-(3-formyl-5-((triisopropylsilyl)ethynyl)phenyl)acetonitrile (TIPS-aldehyde-CN)

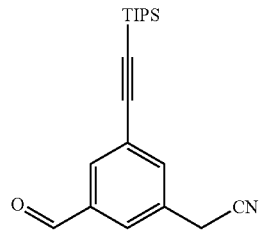

A mixture of PCC (650 mg) and SiO$_2$ (650 mg) was added to CH$_2$Cl$_2$ (25 mL) in a round-bottom flask. TIPS-hydroxyl-CN (500 mg, 1.53 mmol) was added dropwise to the PCC suspension and stirred for two hours. The dark brown suspension was then poured directly onto a SiO$_2$ column and chromatographed (CH$_2$Cl$_2$) to yield TIPS-aldehyde-CN (473 mg, 95%) as a colorless oil. $^1$H NMR (500 MHz, CDCl$_3$) δ=10.02 (s, 1H), 7.95 (s, 1H), 7.81 (s, 1H), 7.71 (s, 1H), 3.84 (s, 2H), 1.16 (m, 21H). $^1$H NMR (500 MHz, CDCl$_3$)=190.69, 137.08, 136.63, 133.17, 127.97, 125.84, 104.28, 94.44, 23.28, 18.64, 11.24. HR-ESI-MS: C$_{20}$H$_{28}$ONSi [M+H$^+$]; Calculated: 326.1935, Found: 326.1931.

Synthesis of Macrocycle Having Formula (I-7)

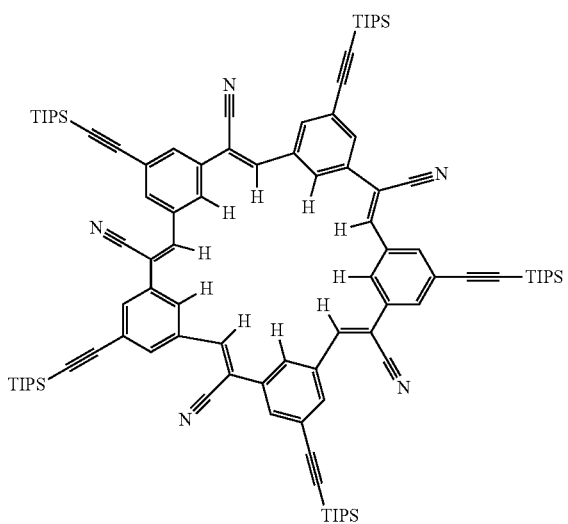

TIPS-aldehyde-CN (100 mg, 0.31 mmol) was dissolved in THF (2 mL) and added to a solution of Cs$_2$CO$_3$ (20 mg) dissolved in ethanol (30 mL) and THF (30 mL). The reaction was kept in the dark and stirred at room temperature for 12 hours. The resulting yellow suspension was concentrated, washed with H$_2$O, brine, and dried over MgSO$_4$. After removal of the solvent, the crude material was chromatographed over SiO$_2$ (5-30% acetone/hexanes) to yield TIPS-CS (42 mg, 45%) as an off-white solid. $^1$H NMR (500 MHz, CDCl$_3$) δ=8.55 (s, 5H), 7.90 (s, 5H), 7.81 (s, 5H), 7.69 (s, 5H), 1.20 (m, 105H). $^{13}$C NMR (125 MHz, CDCl$_3$) δ=141.07, 134.71, 133.96, 132.08, 130.98, 128.21, 126.41, 116.51, 111.65, 104.70, 94.72, 29.70, 18.68, 11.28. TOF-ESI-MS: C$_{200}$H$_{250}$N$_{10}$O$_4$Si$_{10}$Cl [2M+ClO$_4^-$]; Calculated: 3172.71 Found: 3172.61.

Example 8

Synthesis of Macrocycle Having Formula (I-8)

Synthesis of OTBDMS-Hydroxyl-CN

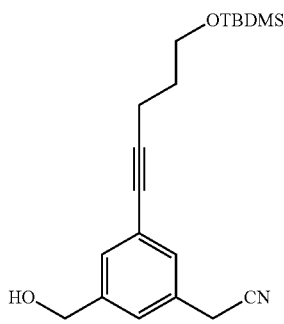 [SMILES: CC(C)(C)[Si](C)(C)OCCCC#Cc1cc(CO)cc(CC#N)c1]

2-(3-(Hydroxymethyl)-5-iodophenyl)acetonitrile (500 mg, 1.83 mmol) was dissolved in THF (15 mL) and degassed with argon. PdCl$_2$(PPh$_3$)$_2$(38 mg), CuI (17 mg), diisopropylamine (1.3 mL), and 4-pentyn-1-ol tert-butyldimethylsilyl ether. (550 mg) was then added in succession and the flask was purged with argon. The solution was stirred at room temperature for 90 minutes. The resulting solution was filtered over Celite, washed with THF, and chromatographed over SiO$_2$ (20-300% ethyl acetate/hexanes) to yield OTBDMS-hydroxyl-CN (615 mg, 95%) as a tan solid. $^1$H NMR (500 MHz, CDCl$_3$) δ=7.30 (s, 1H), 7.23 (s, 1H), 7.20 (s, 1H), 4.62 (s, 2H), 3.72 (t, J=5.8 Hz, 2H), 3.67 (s, 2H), 2.47 (t, J=7.0 Hz, 2H), 2.23 (br s, 1H), 1.78 (quintet, J=6.7 Hz, 2H), 0.89 (s, 9H), 0.05 (s, 6H). $^{13}$C NMR (125 MHz, CDCl$_3$) δ=142.12, 130.19, 129.94, 129.41, 125.33, 125.17, 117.51, 91.23, 79.73, 64.21, 61.56, 31.63, 25.92, 23.30, 18.32, 15.76, −5.32.

Synthesis of OTBDMS-aldehyde-CN

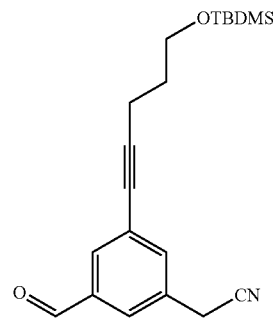 [SMILES: CC(C)(C)[Si](C)(C)OCCCC#Cc1cc(C=O)cc(CC#N)c1]

A mixture of PCC (470 mg) and SiO$_2$ (500 mg) was added to CH$_2$Cl$_2$ (25 mL) in a round-bottom flask. OTBDMS-hydroxyl-CN (500 mg, 1.43 mmol) was added dropwise to the PCC suspension and stirred for two hours. The dark brown suspension was then poured directly onto a SiO$_2$ column and chromatographed (25% ethyl acetate/hexanes) to yield OTBDMS-aldehyde-CN (400 mg, 81%) as a colorless oil. $^1$H NMR (500 MHz, CDCl$_3$) δ=9.95 (s, 1H), 7.80 (s, 1H), 7.70 (s, 1H), 7.59 (s, 1H), 3.78 (s, 2H), 3.73 (t, J=5.8 Hz, 2H), 2.50 (t, J=7.0 Hz, 2H), 1.79 (quintet, J=6.4 Hz, 2H), 0.88 (s, 9H), 0.05 (s, 9H). $^{13}$C NMR (125 MHz, CDCl$_3$) δ=190.76, 137.03, 136.24, 132.70, 131.25, 127.13, 126.39, 116.80, 93.24, 78.61, 61.43, 31.48, 25.90, 23.22, 18.31, 15.78, −5.34.

Synthesis of Macrocycle Having Formula (I-8)

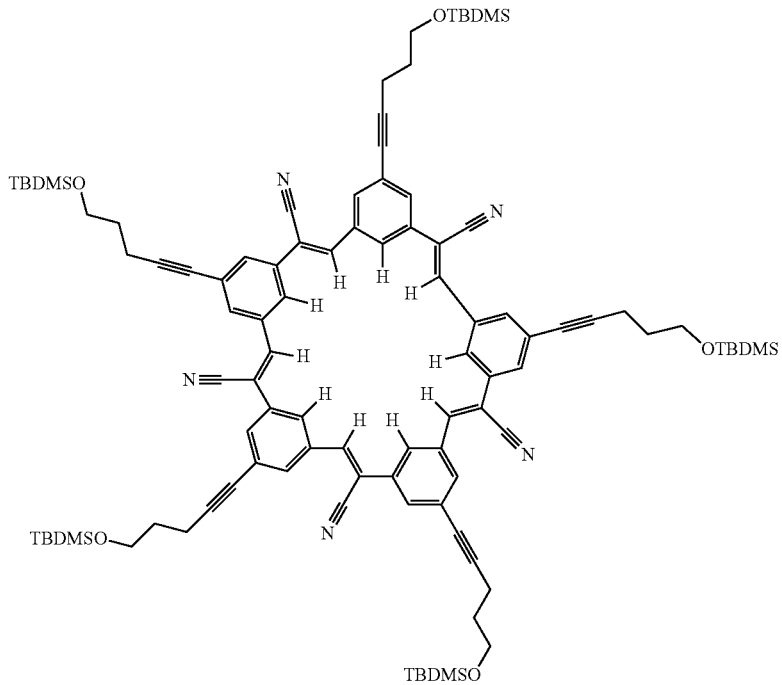 [SMILES: CC(C)(C)[Si](C)(C)OCCCC#Cc1cc2cc(c1)/C(C#N)=C/c1cc(C#CCCCO[Si](C)(C)C(C)(C)C)cc(c1)/C(C#N)=C/c1cc(C#CCCCO[Si](C)(C)C(C)(C)C)cc(c1)/C(C#N)=C/c1cc(C#CCCCO[Si](C)(C)C(C)(C)C)cc(c1)/C(C#N)=C/c1cc(C#CCCCO[Si](C)(C)C(C)(C)C)cc(c1)/C(C#N)=C/2]

OTBDMS-aldehyde-CN (75 mg, 0.22 mmol) was dissolved in THF (20 mL) and ethanol (20 mL). $Cs_2CO_3$ (14 mg) was then added as a solution in THF/EtOH (1:1, 10 mL). The resulting solution was kept in the dark and stirred at room temperature for 12 hours. After removal of the solvent, the crude product was chromatographed over $SiO_2$ ($CHCl_3$) to yield OTBDMS-CS as a white solid (42 mg, 60% o yield). $^1$H NMR (300 MHz, $CDCl_3$) δ=8.43 (s, 5H), 7.79 (s, 5H), 7.61 (s, 5H), 7.55 (s, 5H), 3.80 (t, J=5.8 Hz, 2H), 2.55 (t, J=6.8 Hz, 2H), 1.87 (t, J=6.3 Hz, 2H), 0.95 (s, 45H), 0.13 (s, 45H). $^{13}$C NMR (125 MHz, $CDCl_3$) δ=141.20, 134.86, 134.37, 132.66, 130.15, 127.89, 127.31, 117.08, 111.16, 94.00, 79.43, 78.11, 62.22, 32.27, 26.34, 18.82, 16.58, −4.96. HR-ESI-MS: $C_{100}H_{125}O_5N_5Si_5Cl$ [M+Cl$^-$]; Calculated: 1650.8216, Found: 1650.8226.

Example 9

Synthesis of Iodo-Cyanostar (CS-I)

Synthesis of 2-(3-(hydroxymethyl)-5-iodophenyl)acetonitrile (2)

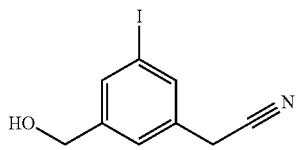 [SMILES: N#CCc1cc(I)cc(CO)c1]

(5-Iodo-1,3-phenylene)dimethanol (1) (5 g, 18.9 mmol) was dissolved in toluene (200 mL) and heated to 90° C. on an oil bath. The solution was cooled to 70° C. and 47-49% aqueous solution of HBr (2.8 mL, 24.6 mol) was added and stirred for 3 h. The reaction mixture was cooled under ice bath and neutralized with $Na_2CO_3$ solution. The organic phase was collected and the aqueous layer was further extracted with EtOAc. Organic layers were combined and dried with $MgSO_4$, filtered then concentrated under vacuum. The resulting crude oil product was dissolved in THF (50 mL), MeOH (20 mL) and water (50 mL). KCN (1.6 g, 24.6 mmol) was added and stirred at 80° C. for 8 h. After cooling to room temperature, THF and MeOH were removed in vacuo. The mixture was extracted with EtOAc and the organic phase was dried with $MgSO_4$, filtered and the solvents were removed in vacuo. Column chromatography on silica gel with hexane:EtOAc=1:1 to 1:2 resulted a white solid product (2) (4.3 g, 15.7 mmol, 84% yield). $^1$H NMR (400 MHz, $CDCl_3$) δ=7.67 (s, 1H), 7.57 (s, 1H), 7.29 (s, 1H), 4.65 (d, J=4.7 Hz, 2H), 3.70 (s, 2H), 2.29 (t, J=4.8 Hz, 1H). $^{13}$C NMR (100 MHz, $CDCl_3$) δ=144.0, 135.4, 135.1, 131.8, 125.3, 117.27, 94.6, 63.2, 22.8.

Synthesis of 2-(3-Formyl-5-iodophenyl)acetonitrile (3)

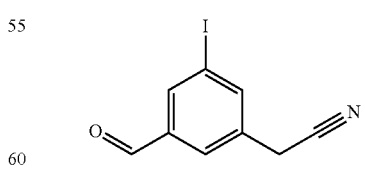

PCC (3.1 g, 14.3 mmol) and silica gel (4 g) were mixed well using a mortar and pestle and suspended in $CH_2Cl_2$ (70 mL). A solution of 2-(3-(hydroxymethyl)-5-iodophenyl)acetonitrile (2) (3 g, 11.0 mmol) in $CH_2Cl_2$ (60 mL) was dropwise added while stirring. The reaction mixture was stirred at room temperature for 3 h and filtered through a short silica gel column and washed with CH$_2$Cl$_2$ to give a white solid product (3) (2.4 g, 8.9 mmol, 80% yield). $^1$H NMR (400 MHz, CDCl$_3$) δ=9.94 (s, 1H), 8.18 (s, 1H), 7.96 (s, 1H), 7.82 (s, 1H), 3.81 (s, 2H). $^{13}$C NMR (100 MHz, CDCl$_3$) δ=189.7, 142.2, 138.4, 138.3, 128.0, 116.5, 95.1, 22.9.

Synthesis of Iodo-cyanostar (CS-I)

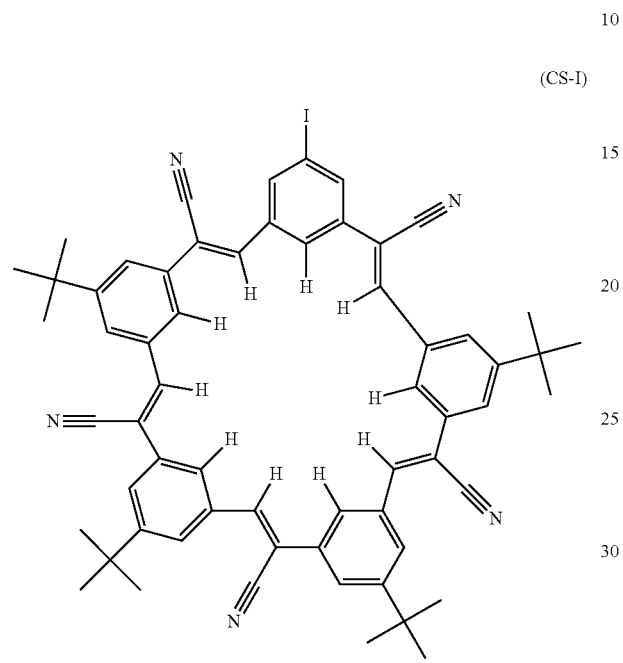

(CS-I)

Cs$_2$CO$_3$ (1.19 g) was suspended in EtOH (2 L), poured into a 4 L amber bottle, and stirred for 30 minutes to promote dissolution. Once dissolved, THF was added (2 L) followed by 2-(3-(tert-butyl)-5-formylphenyl)acetonitrile (4) (6.90 g, 34.3 mmol) and 2-(3-formyl-5-iodophenyl)acetonitrile(3) (620 mg, 2.3 mmol) as solutions in THF (60 mL). The solution was kept in the dark and stirred for 24 hours at room temperature. The resulting light yellow suspension was concentrated to dryness and separated over SiO$_2$ (2:1 CH$_2$Cl$_2$/hexanes) to yield crude CS-I. The product was further purified via slow diffusion of Et$_2$O into a concentrated CHCl$_3$ solution to yield CS-I (950 mg, 0.96 mmol, 42% yield) as an off-white solid. $^1$H NMR (500 MHz, CDCl$_3$) δ=8.57 (s, 1H), 8.52 (m, 2H), 8.50 (s, 1H), 8.46 (s, 1H), 7.98 (s, 1H), 7.82-7.80 (m, 4H), 7.75 (s, 1H), 7.69 (s, 1H), 7.67 (s, 1H), 7.65 (s, 1H), 7.62 (m, 2H), 7.61 (s, 1H), 7.58 (m, 2H), 7.52 (s, 1H), 1.53 (m, 18H), 1.503 (s, 9H), 1.499 (s, 9H). $^{13}$C NMR (125 MHz, CDCl$_3$) δ=154.28, 154.18, 154.16, 143.09, 141.58, 141.49, 141.36, 138.91, 137.34, 136.22, 135.79, 135.49, 134.28, 134.24, 133.77, 133.66, 133.58, 133.22, 127.73, 126.93, 126.65, 126.35, 126.21, 126.17, 125.94, 125.70, 124.80, 124.63, 124.48, 124.45, 117.44, 117.35, 116.87, 112.72, 110.94, 110.74, 110.63, 108.73, 96.07, 35.62, 31.31, 31.28.

Example 10

Synthesis of TMS-cyanostar (CS-TMS)

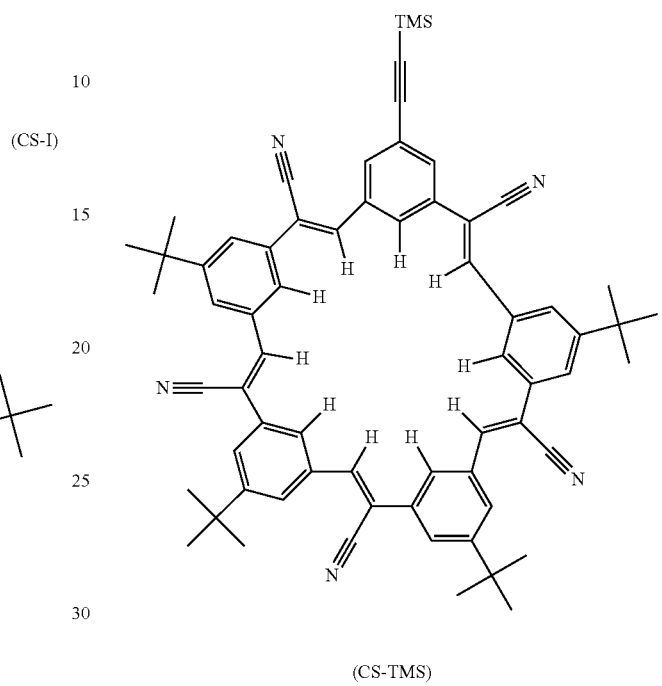

(CS-TMS)

Compound having Formula (CS-I) (234 mg, 0.237 mmol) was dissolved in THF (5 mL) and degassed with argon for 15 minutes. To the degassed solution was then added PdCl$_2$(PPh$_3$)$_2$ (8 mg), CuI (4.5 mg), TMS-acetylene (66 μL), and diisopropylamine (170 μL). The flask was sealed and the solution was stirred under argon at room temperature for 12 hours. NH$_4$Cl (aq) was then added and the resulting suspension was extracted with dichloromethane, washed with brine, and dried over MgSO$_4$. After removal of the solvents in vacuo, the product was purified over SiO$_2$ (30-60% dichloromethane in hexanes) to yield CS-TMS (192 mg, 85% yield) as a white solid. $^1$H NMR (500 MHz, CDCl$_3$) δ=8.48 (m, 2H), 8.45 (s, 1H), 8.42 (s, 1H), 8.18 (s, 1H), 7.81 (m, 3H), 7.75 (m, 2H), 7.71 (s, 1H), 7.68 (m, 2H), 7.66 (m, 2H), 7.61 (s, 1H), 7.58 (m, 2H), 7.55 (s, 1H), 7.53 (s, 1H), 1.54 (m, 18H), 1.51 (m, 18H), 0.39 (s, 9H). $^{13}$C NMR (500 MHz, CDCl$_3$) δ=154.14, 154.12, 154.07, 154.04, 142.82, 141.52, 141.42, 141.30, 139.91, 134.64, 134.21, 134.08, 133.96, 133.70, 133.62, 133.57, 133.37, 131.90, 130.12, 128.13, 126.56, 126.49, 126.46, 126.11, 126.04, 125.91, 125.81, 125.62, 124.72, 124.60, 124.46, 124.45, 117.42, 117.30, 117.11, 112.33, 110.69, 110.62, 110.56, 109.45, 102.81, 97.93, 35.60, 35.59, 31.32, −0.10.

Example 11

Synthesis of Alkynyl-cyanostar (CS-Ac)

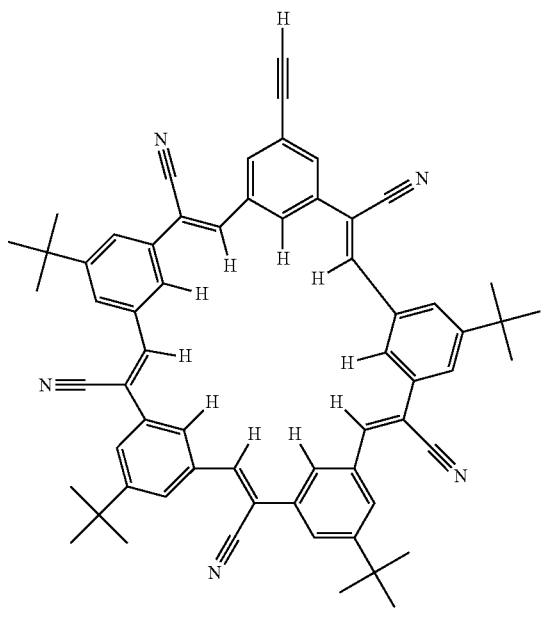

(CS-Ac)

TMS-CS (630 mg, 0.66 mmol) was dissolved in THF (25 mL), sat. $K_2CO_3$/MeOH (3 mL) and stirred for 20 minutes. After removal of the solvents, the crude material was separated over $SiO_2$ (dichloromethane). The product was further purified via slow diffusion of $Et_2O$ into a concentrated $CHCl_3$ solution to yield CS-Ac (500 mg, 85%/a yield) as an off-white solid. $^1$H NMR (500 MHz, $CDCl_3$) δ=8.47 (s, 1H), 8.44 (m, 2H), 8.37 (s, 1H), 8.22 (s, 1H), 7.80-7.78 (m, 3H), 7.73 (s, 1H), 7.68 (m, 2H), 7.66 (m, 2H), 7.60 (m, 3H), 7.56 (s, 1H), 7.53 (s, 1H), 7.52 (s, 1H), 7.50 (s, 1H), 3.28 (s, 1H), 1.52 (m, 18H), 1.48 (s, 9H), 1.46 (s, 9H). $^{13}$C NMR (100 MHz, $CD_2Cl_2$) δ=153.6, 153.5, 142.5, 141.2, 141.08, 141.01, 139.4, 134.4, 133.9, 133.8, 133.48, 133.42, 133.36, 133.2, 133.0, 131.1, 129.7, 128.5, 126.1, 125.99, 125.93, 125.82, 125.6, 125.5, 124.3, 124.2, 124.1, 117.1, 116.8, 111.9, 110.4, 110.12, 110.10, 108.8, 81.6, 79.7, 35.21, 35.17, 30.83, 30.80.

Example 12

Synthesis of Methacrylate-cyanostar (CS-C$_{11}$-Methacrylate)

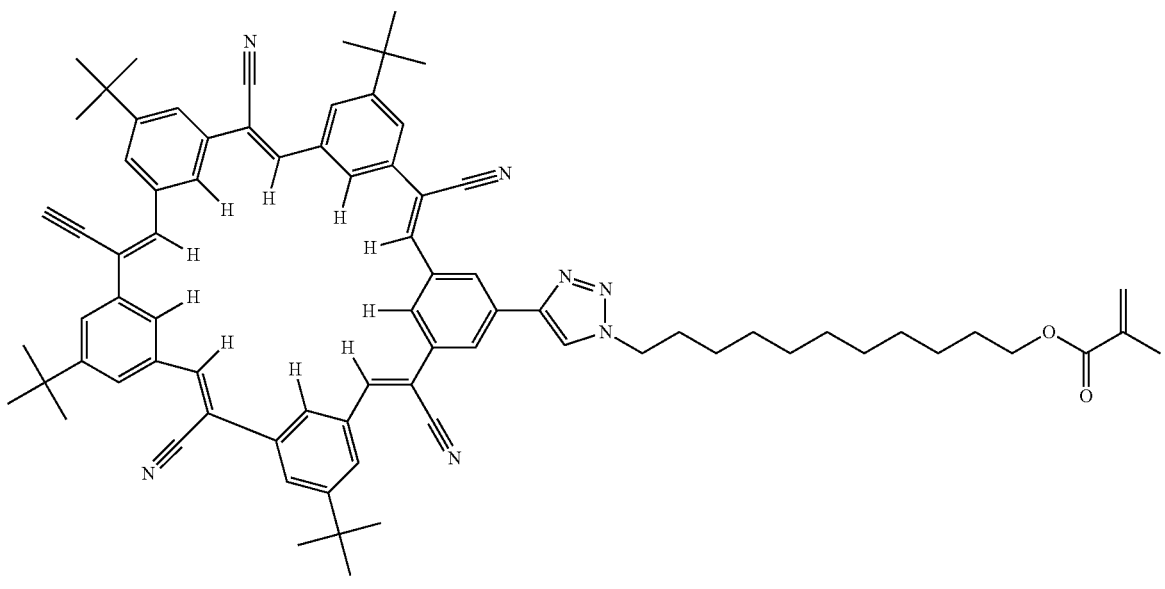

(CS-C$_{11}$-methacrylate)

CS-Ac (30 mg, 0.03 mmol) and 11-azidoundecyl methacrylate (14 mg, 0.03 mmol) was dissolved in THF (2 mL), t-BuOH (500 μL), H$_2$O (250 μL), and degassed with argon. TBTA (5 mg), CuSO$_4$·5H$_2$O (1.7 mg in 170 μL H$_2$O), and sodium ascorbate (2 mg in 200 μL H$_2$O) was then added and the solution was stirred at room temperature for 24 hours. The resulting suspension was diluted with dichloromethane, washed with brine, and dried over MgSO$_4$. After removal of the solvent, the crude product was chromatographed over SiO$_2$ (0-1.5% acetone/dichloromethane) to yield CS-C$_{11}$-methacrylate (25 mg, 63%) as an off-white solid. $^1$H NMR (500 MHz, CD$_2$Cl$_2$) δ=8.68 (s, 1H), 8.55-8.52 (s, 3H), 8.47 (s, 1H), 7.97 (s, 1H), 7.81-7.79 (s, 4H), 7.73-7.64 (m, 10H), 6.09 (s, 1H), 5.54 (s, 1H), 4.39 (t, J=7.0 Hz, 2H), 4.13 (t, J=6.6 Hz, 2H), 1.99 (m, 2H), 1.94 (s, 3H), 1.67 (m, 2H), 1.52 (m, 18H), 1.49 (m, 18H), 1.38-1.30 (m, 14H). $^{13}$C NMR (125 MHz, CD$_2$Cl$_2$) δ=167.53, 154.03, 146.00, 142.58, 141.64, 141.56, 140.74, 136.53, 135.34, 134.37, 134.28, 134.23, 133.80, 133.74, 133.70, 133.66, 133.47, 133.22, 128.11, 126.74, 126.65, 126.55, 126.26, 126.21, 126.10, 125.99, 125.90, 125.10, 124.47, 124.42, 124.35, 123.85, 120.68, 117.46, 117.42, 117.40, 117.28, 111.52, 110.81, 110.66, 110.53, 109.84, 64.79, 50.64, 35.58, 35.55, 31.26, 30.32, 29.68, 29.45, 29.42.

Example 13

Synthesis of Bis-CS-C$_{12}$ (IV-CS-12D)

(t, J=7.0 Hz, 4H), 2.03 (m, 4H), 1.51-1.40 (m, 88H). $^{13}$C NMR (125 MHz, CDCl$_3$) δ=153.75, 145.80, 142.40, 141.49, 141.38, 140.39, 135.05, 134.42, 134.19, 134.09, 133.75, 133.69, 133.51, 133.07, 127.98, 126.32, 125.91, 125.46, 124.36, 124.22, 123.65, 120.96, 117.41, 117.35, 117.23, 111.40, 110.42, 110.23, 109.47, 50.53, 35.45, 35.41, 31.04, 30.03, 29.68, 28.75, 28.70, 28.51, 26.17.

Example 14

Synthesis of Pyridyl-cyanostar (CS-Py)

Synthesis of 2-(3-(Hydroxymethyl)-5-(pyridin-4-yl)phenyl)acetonitrile (5)

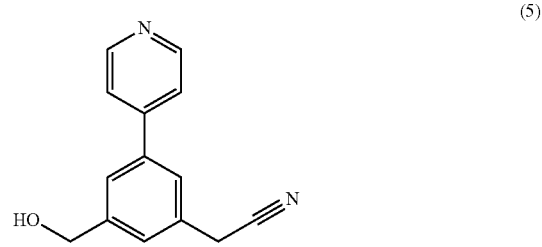 [SMILES: N#CCc1cc(CO)cc(-c2ccncc2)c1]

(5)

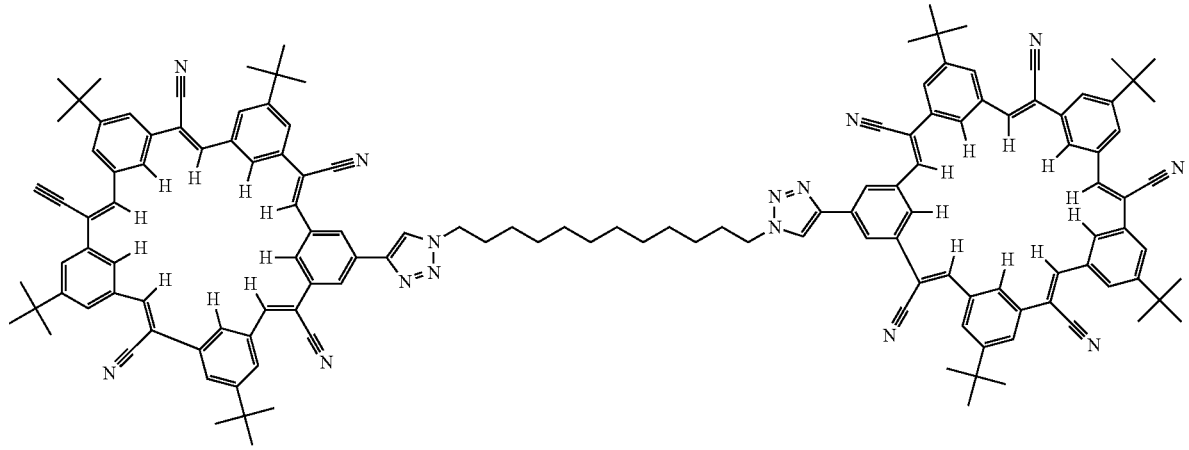

(IV-CS-12D)

CS-Ac (100 mg, 0.11 mmol) and 1,12-bisazidododecane (13.5 mg, 0.11 mmol) were dissolved in THF (5 mL), t-BuOH (1 mL), H$_2$O (500 μL), and degassed with argon. To the solution was then added tris[(1-benzyl-1H-1,2,3-triazol-4-yl)methyl]amine (12 mg), CuSO$_4$·5H$_2$O (5.6 mg dissolved in 200 μl H$_2$O), and sodium ascorbate (7 mg dissolved in 200 μl H$_2$O). The solution was warmed to 60° C. and stirred under argon for 18 hours. The solution was then cooled, washed with H$_2$O, extracted with CHCl$_3$, and dried over MgSO$_4$. After removal of the solvent, the crude product was chromatographed over SiO$_2$ (CHCl$_3$). The product obtained was further purified via slow diffusion of Et$_2$O into a concentrated CHCl$_3$ solution to yield IV-CS-12D (48 mg, 42% yield) as a light yellow solid. $^1$H NMR (500 MHz, CD$_2$Cl$_3$) δ=8.64 (s, 2H), 8.45-8.42 (m, 6H), 8.17 (s, 2H), 8.07 (s, 2H), 7.78-7.71 (m, 14H), 7.68-7.59 (m, 14H), 4.44

A mixture of 2-(3-(hydroxymethyl)-5-iodophenyl)acetonitrile (2) (800 mg, 2.93 mmol), 4-pyridinylboronic acid (470 mg, 3.11 mmol), Pd(PPh$_3$)$_4$(39 mg, 0.055 mmol) and K$_2$CO$_3$ (2 g, 14.7 mmol) in toluene 20 mL, water 10 mL and ethanol 10 mL was degassed by freeze-pump-thaw cycles (×3). The reaction was stirred under argon atmosphere for 10 h at 80° C. The reaction was cooled to room temperature and extracted with CH$_2$Cl$_2$. Column chromatography on silica gel with CH$_2$Cl$_2$:MeOH=90:10 resulted in a white solid product (400 mg, 1.78 mmol, 61% yield). $^1$H NMR (400 MHz, CDCl$_3$) δ=8.67 (d, J=8.7 Hz, 2H), 7.61 (s, 1H), 7.51 (m, 3H), 7.43 (s, 1H), 4.82 (s, 2H), 3.85 (s, 2H). $^{13}$C NMR (75 MHz, CDCl$_3$) δ=149.7, 147.6, 143.7, 138.8, 131.0, 126.8, 125.2, 124.8, 117.6, 63.7, 23.4.

Synthesis of 2-(3-Formyl-5-(pyridin-4-yl)phenyl) acetonitrile (6)

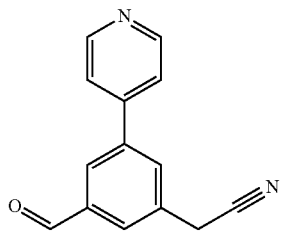

(6)

To a solution of 2-(3-(hydroxymethyl)-5-(pyridin-4-yl) phenyl)acetonitrile (5) (300 mg, 1.34 mmol) in $CH_2Cl_2$ (30 mL) was added $MnO_2$ (2 g, 23 mmol) and stirred for 1 h. Additional $MnO_2$ (1 g, 12 mmol) was added and stirred at room temperature overnight. The reaction mixture was filtered through a pad of Celite and washed with MeOH: DCM=1:1 mixture to give a white solid product (190 mg, 0.855 mmol, 64% yield) $^1$H NMR (400 MHz, $CDCl_3$) δ=10.12 (s, 1H), 8.73 (d, J=8.7 Hz, 2H), 8.12 (s, 1H), 7.95 (s, 1H), 7.90 (s, 1H), 7.56 (d, J=7.6 Hz, 2H), 4.00 (s, 2H). $^{13}$C NMR (100 MHz, $CDCl_3$) δ=190.7, 150.4, 145.7, 140.1, 137.6, 132.2, 131.8, 129.1, 127.6, 121.3, 116.9, 23.3.

Synthesis of Pyridyl-cyanostar (CS-Py)

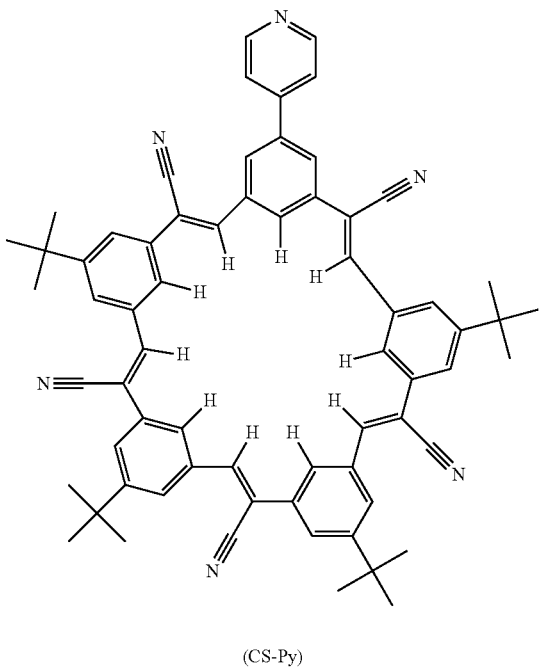 [SMILES: CC(C)(C)c1cc2cc(c1)/C(C#N)=C/c1cc(cc(C(C)(C)C)c1)/C(C#N)=C/c1cc(cc(C(C)(C)C)c1)/C(C#N)=C/c1cc(cc(C(C)(C)C)c1)/C(C#N)=C/c1cc(cc(-c3ccncc3)c1)/C(C#N)=C/2]

(CS-Py)

$Cs_2CO_3$ (65 mg, 0.2 mmol) was suspended in EtOH (250 mL) and stirred for 30 minutes. Once dissolved, THF was added (200 mL) followed by 2-(3-(tert-butyl)-5-formylphenyl)acetonitrile(4) (820 mg, 4.1 mmol) and 2-(3-formyl-5-(pyridin-4-yl)phenyl) acetonitrile (6) (50 mg, 0.23 mmol) as solutions in THF (50 mL). The solution was kept in the dark and stirred for 24 hours at room temperature. The resulting light yellow suspension was concentrated to dryness and purified over $SiO_2$ ($CH_2Cl_2$:methanol=9:1) to yield CS-Py (45 mg, 0.048 mmol, 21% yield) as a white solid. $^1$H NMR (400 MHz, $CD_2Cl_2$) δ=8.85 (s, 1H), 8.76 (d. J=8.8 Hz, 2H), 8.70-8.67 (m, 4H), 8.09 (s, 1H), 7.84 (s, 1H), 7.90-7.87 (m, 5H), 7.84 (s, 1H), 7.78 (m, 3H), 7.72-7.69 (m, 6H), 1.49 (s, 36H). $^{13}$C NMR (100 MHz, $CD_2Cl_2$) δ=153.75, 153.68, 153.66, 150.5, 145.9, 142.5, 141.56, 141.52, 141.32, 140.3, 140.1, 135.4, 134.7, 134.29, 134.25, 134.19, 133.77, 133.68, 133.61, 133.56, 133.30, 128.5, 127.0, 126.7, 126.39, 126.35, 126.09, 125.87, 125.83, 125.71, 125.0, 124.4, 124.09, 124.03, 121.3, 117.21, 117.18, 117.08, 116.97, 112.0, 110.7, 110.51, 110.49, 109.5, 35.2, 30.77, 30.75.

Example 15

Solid-state Structure of the Cyanostar Macrocycle (CS)

Crystals grown by slow evaporation from a 1:1 solution of $CH_2Cl_2$ and diglyme were analyzed by X-ray diffraction to provide a solid-state structure of CS (FIG. 1C) that confirms the $C_5$ symmetry. In the solid state, cyanostars prefer to exist as π-stacked dimers, which pack as lamellar throughout the crystal. By contrast, Zeng's pentamers exhibits lamellar packing of individual macrocycles in the solid state. The dimers have diglyme solvent molecules disordered in their centers, which were eliminated using Platon SQUEEZE during the refinement. Unlike the semi-planar structures of Zeng and MacLachlan, cyanostars are shaped like shallow bowls akin to chiral sumanenes and corannulenes where the CS dimers meet at the seams created by their inner rims rather than being nested together. The two macrocycles are rotationally offset from each other, which is attributed to a combination of electrostatic complementarity between the electron deficient πsurfaces of the two cycles and steric effects involving tert-butyl groups.

In the solid state, the chirality defined by the curved geometry becomes apparent. Following the suggestion by Szumna, the stereochemistry is defined by looking into the bottom of the bowl down the $C_5$ axis. The direction for each cyanostar can be defined using priority rules. Starting from the t-butyl substituted carbon on the phenylene ring, the quaternary nitrile-substituted carbon has greater priority than the methine carbon. Thus, a vector points from the phenylene to the quaternary nitrile-substituted carbon. Cyanostars observed in the solid state that are directed clockwise and counterclockwise are enantiomers designated P and M, respectively. In solution, however, the M and P enantiomers of CS are expected to racemize through bowl-bowl transitions in solution akin to chiral bucky bowls. The existence of dimers also predicates the generation of stereochemical isomers at the paired level (see, for example, FIG. 1D).

We observed that the packing requirements of the crystal allowed the CS to occupy sites with either Al or P arrangements. This packing gave rise to whole molecule disorder (WMD) that was solved by populating the crystal with 63% M and 37% P stereoisomers. The disorder leads to an averaged electron density for two macrocycles within the dimer that are related by an inversion center (space group P–1). For this reason, all four stereoisomers may be present with the limiting cases having the following ratios, ~63:37 M-P:P-M and ~26:37:37 M-P:P-P-M-M with the M-P dimer present in all cases. The P-P and M-M dimers are enantiomers of each other. The diastereomeric P-M and M-P dimers are also present. These dimers are also enantiomers of each other but only in the solid state because of their translational and rotational degrees of freedom are frozen. If present in solution, this pair of dimers would exist as the meso compound.

Example 16

Size-selective Recognition of Large Weakly Coordinating Anions

CS displays size-selective binding of large anions in a mixed solution of 40% methanol (MeOH) in dichloromethane ($CH_2Cl_2$), selected to dissociate ion pairs. The macrocycle has a pseudo-spherical shape and a diameter of ~4.5 Å with the dimer's cavity slightly larger at ~5.2 Å. Titrations were conducted to quantify the binding affinity of variously sized anions (see Supplementary Information) having ionic diameters ranging from $Cl^-$ ($d_{ion}$~3.4 Å) to $FeCl_4^-$ ($d_{ion}$~6.3 Å).

Titrations were conducted at micromolar concentrations and monitored using UV-Vis spectroscopy to generate accurate association constants. Results from $^1H$ NMR spectroscopy (vide infra) and electrospray ionization mass spectrometry (ESI-MS) indicated the importance of 2:1 sandwich complexes during the initial stages of the titration, as characterized by an overall stability constant, $\beta_2$. The 1:1 complexes emerge subsequently after adding excess anion ($X^{-}$).

  (1)

  (2)

  (3)

Figure 2A:
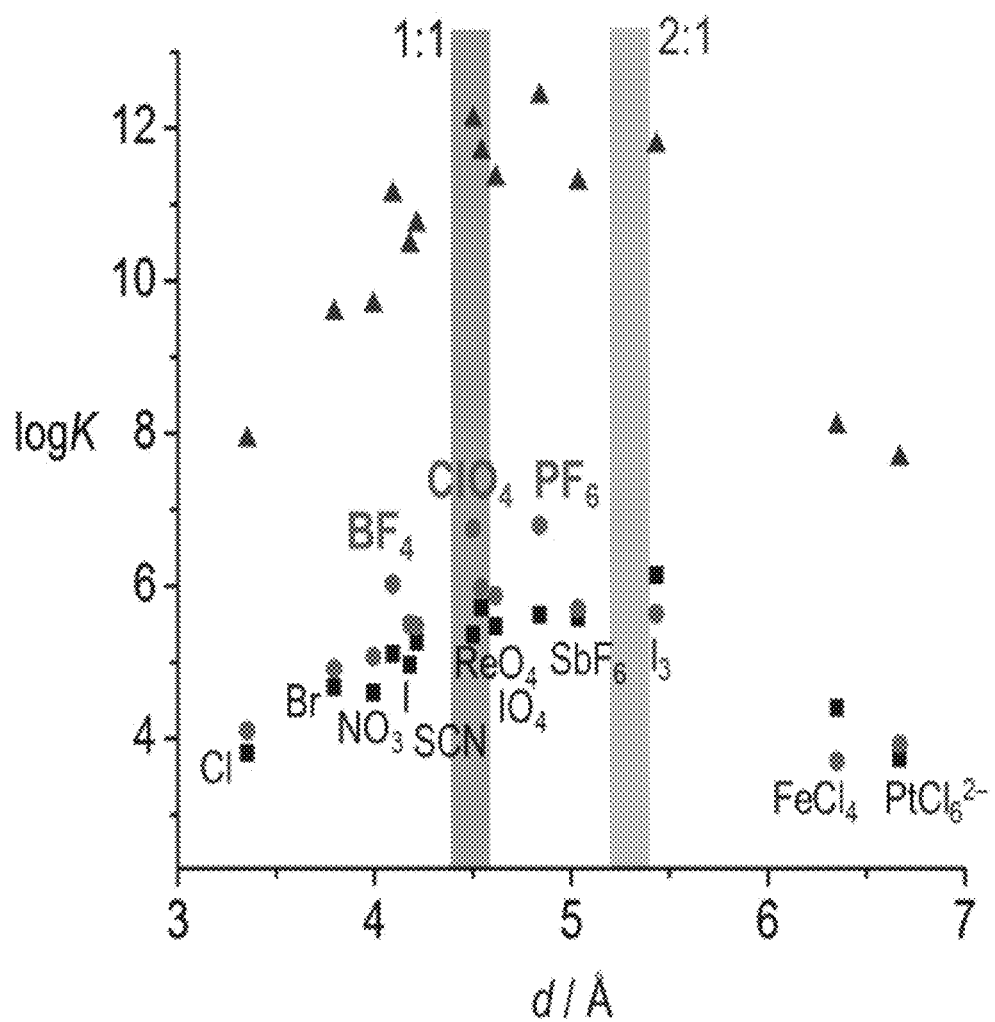
FIG. 2A illustrates and a plot of binding constants between CS and select anions for log $K_{11}$ (squares), log $K_{12}$ (circles) and log $\beta_2$ (triangles). Data obtained from equilibrium-restricted factor analysis implemented with Sivvu (40% MeOH/$CH_2Cl_2$) at RT.
Figure 2B:
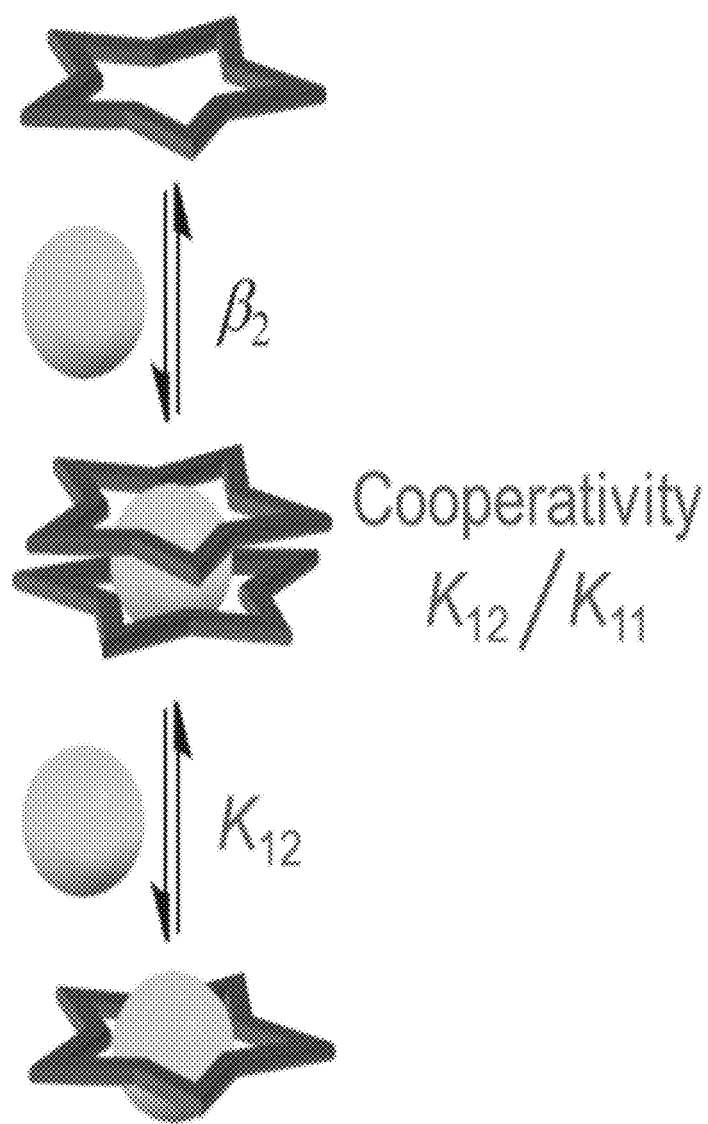
FIG. 2B illustrates the cavity size of CS and anion binding selectivity.

A plot of log $K_{11}$ and log $\beta_2$ versus the anion size (FIG. 2A) shows high binding affinities and a peak preference for bigger anions that match the large central cavity. The breadth of the peak is consistent with a certain degree of flexibility in the receptor. The binding affinities observed for $BF_4^-$, $ClO_4^-$ and $PF_6^-$, log $K_{11}$>5 and log $\beta_2$>11, are unusually large for such "weakly coordinating" anions. Without wishing to be bound to any particular theory, it appears that anion stabilization may be attributed to the electropositive cavity defined by the olefinic and phenylene H-bonding environment as well as the benefits gained from the Hofmeister bias. That is, desolvation of charge-diffuse anions like $PF_6^-$ is favored in more protic solvents like MeOH and this assistance increases with the anion's size. Finally, strong positive cooperativity is observed for $BF_4^-$, $ClO_4^-$ and $PF_6^-$, while all other anions tested weak positive cooperativity (see, for example, FIG. 2B). The marked difference between anions of a similar size, e.g., $ClO_4^-$ shows high positive cooperativity whereas similarly sized $ReO_4^-$ does not, suggests that there may be some specific complementarity between some of these guests and the CS receptor.

Figure 3A:
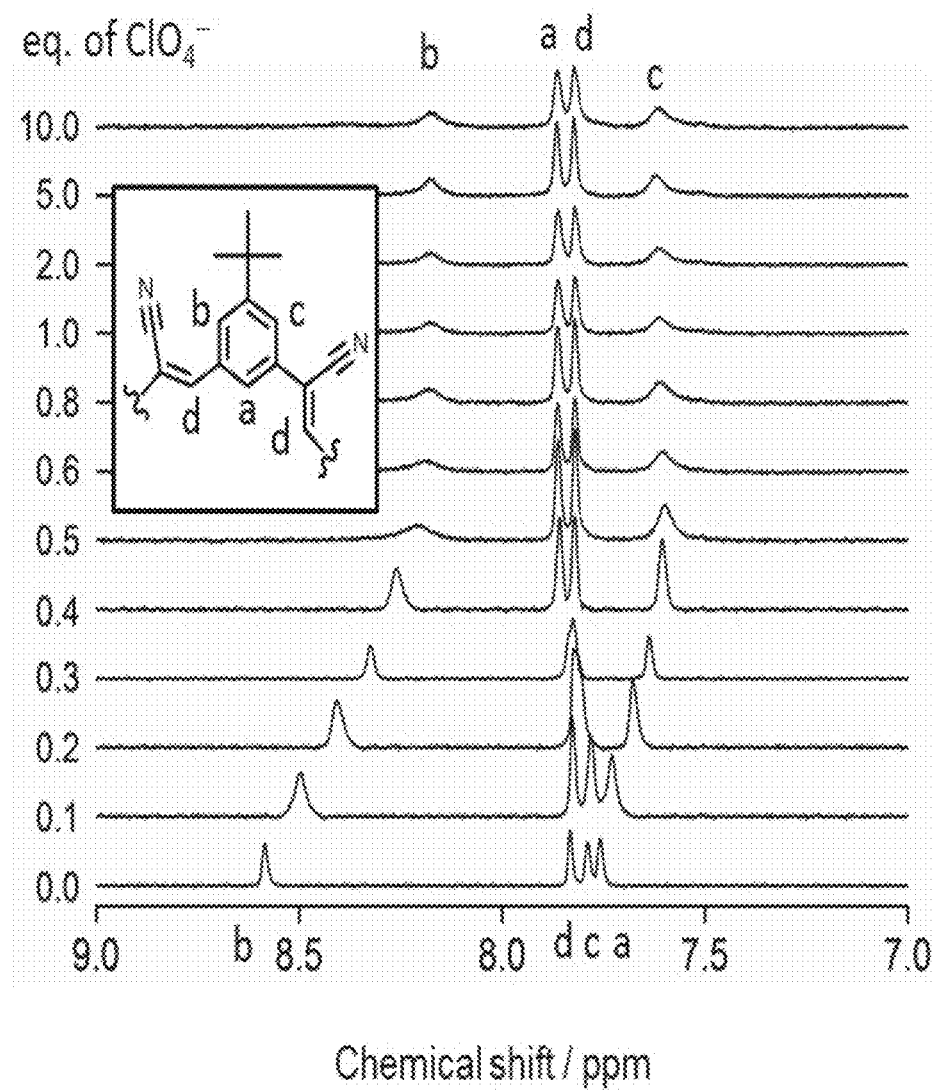
FIG. 3A illustrates an NMR spectroscopic characterization of anion complexes and the [3]rotaxane, wherein an NMR Titration of CS with $TBAClO_4$ (40% $CD_3OD$ in $CD_2Cl_2$, 500 MHz, 298 K) is shown.

The preference for 2:1 sandwiches was made clear from titrations conducted at ~1 mM as monitored using $^1H$ NMR spectroscopy (FIG. 3A). Addition of the tetrabutylammonium ($TBA^+$) salt of $ClO_4^-$ showed monotonic shifts in position that locked into place upon addition of 0.5 eq, while only modest movements occurred during the addition of extra salt, up to 10 equivalents. Similar behavior was observed for $PF_6^-$. Consistent with a π-stacked sandwich complex, the aromatic protons on the outer rim of CS, $H^b$ and $H^c$, shift upfield by ~0.2-0.4 ppm. By contrast, the electropositive hydrogens that line the cavity, $H^a$ and $H^d$ shift downfield for $Cl^-$, $NO_3^-$ and $I^-$ (see Supplementary Information) indicative of CH . . . anion H-bonding. These signals move further downfield during formation of the 1:1 complexes as the π-stacked environment disappears, an assessment made accessible on account of the negligible cooperativity for these anions. Even though the olefinic hydrogens $H^d$ are more electropositive, the hydrogens on the phenylene rings, $H^a$, show larger shifts in position. This outcome is consistent with their closer proximity to the center of the cavity subjecting them to a larger deshielding environment. In the case of $ClO_4^-$ (FIG. 3A) and $PF_6^-$, the olefinic CH hydrogens actually shift upfield by ~0.1 ppm while the phenylene CH hydrogens shift downfield by ~0.1 ppm. This observation emphasizes the large influence of stacking in the sandwich complexes stabilized under conditions of positive cooperativity (vide infra).

Figure 3B:
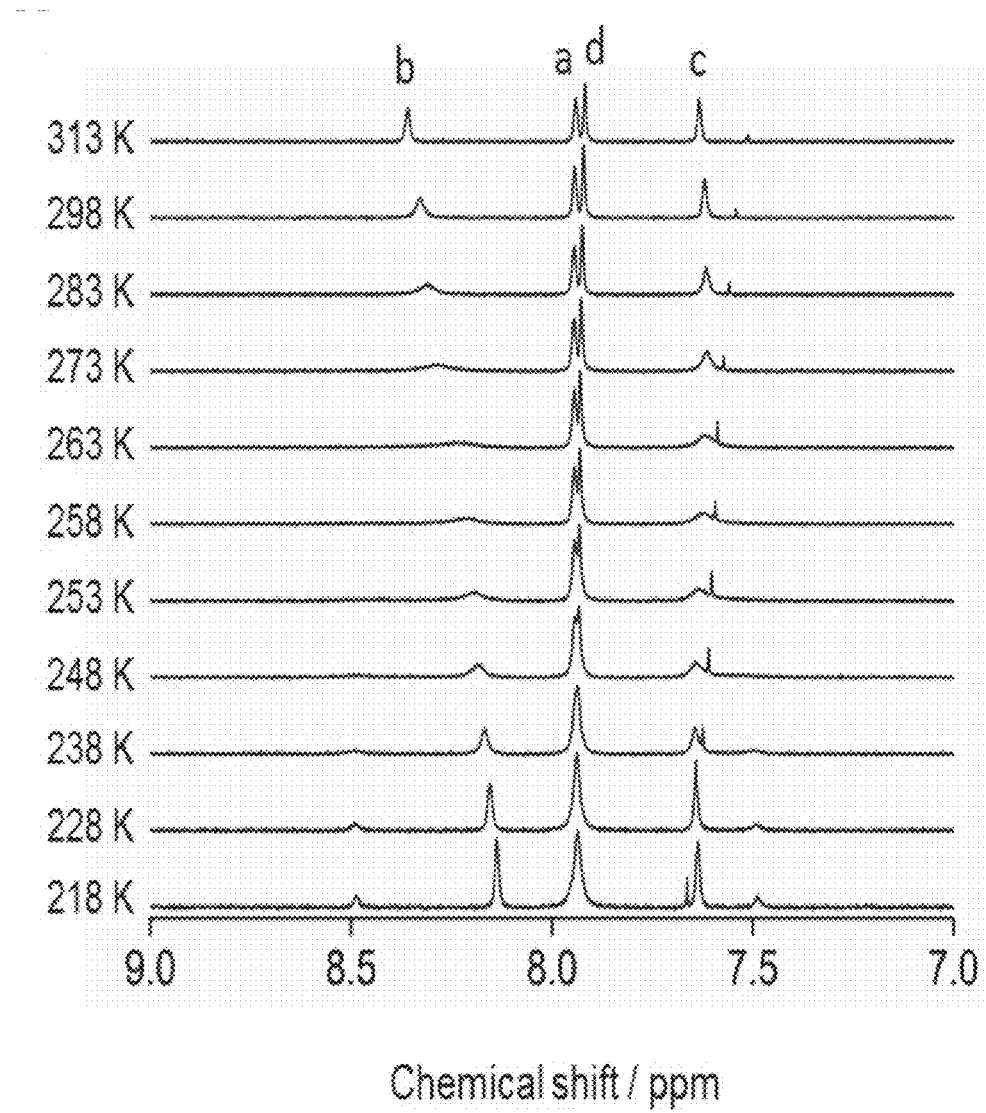
FIG. 3B illustrates variable temperature NMR $^1H$ spectroscopy of the 2:1 complex $CS_2.ClO_4^-.TBA^+$.

The broad signals apparent in the NMR spectra upon addition of 0.5 eq. motivated a variable temperature (VT) study of the 2:1 sandwich formed with $ClO_4^-$ (FIG. 3B) that ultimately indicated the existence of diastereomers. First, the inner protons $H^a$ and $H^d$ largely hold their positions and sharpness during a temperature scan from 313 to 223 K. This finding indicates retention of the 2:1 sandwich; that is, the dynamics do not reflect equilibration amongst the free receptor or the 1:1 complex where the $^1H$ resonances are in different positions. Second, the outer protons $H^b$ and $H^c$ and the t-butyl protons $H^e$ show coalescence behavior consistent with major and minor diastereoisomers present in the ratio ~8:2. These two signals are tentatively ascribed to the meso and chiral dimers, respectively, as implicated from the crystal structure analysis.

Example 17

[3]Rotaxane Formation Using a Dialkylphosphate

Buoyed up by this preference for larger anions, an interlocked molecule in the form of a dialkylphosphate [3]rotaxane was prepared. Examples of anionic templates in which the negatively charged species lives on inside the dumbbell are few. While Vogtle and Schalley used phenolates as templates, they are consumed in the preparation of the rotaxanes Others have generated anions by deprotonation or by photoreduction to switch rotaxanes. However, only one rotaxane reported by Schalley outlines the use and retention of the negatively charged phenolate. A related study by Winpenny and Leigh employed a monoanionic inorganic macrocycle during templation around a dialkylammonium cation. All other accounts make use of labile ions like $Cl^-$ as templates following pioneering work of Beer. Our demonstration also extends effort to expand the diversity of functional groups used as templates, which include Smith's zwitterions that bear large anionic character and Leigh's use of neutral phosphorous compounds.

Figure 4A:
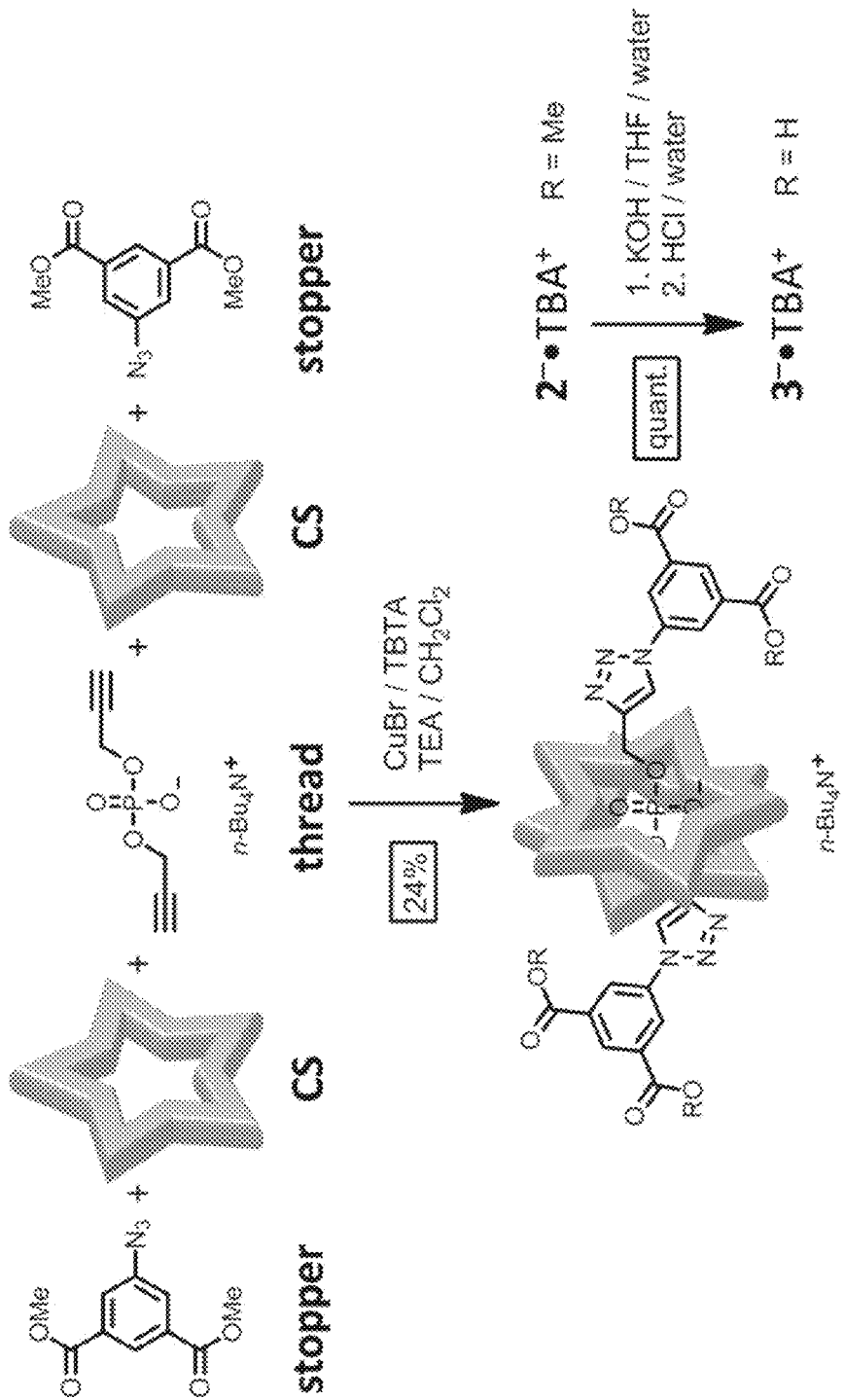
FIG. 4A illustrates synthesis of phosphate templated [3]rotaxanes, wherein an exemplary synthetic scheme for formation of $2^-.TBA^+$ and $3^-.TBA^+$ is shown.
Figure 4B:
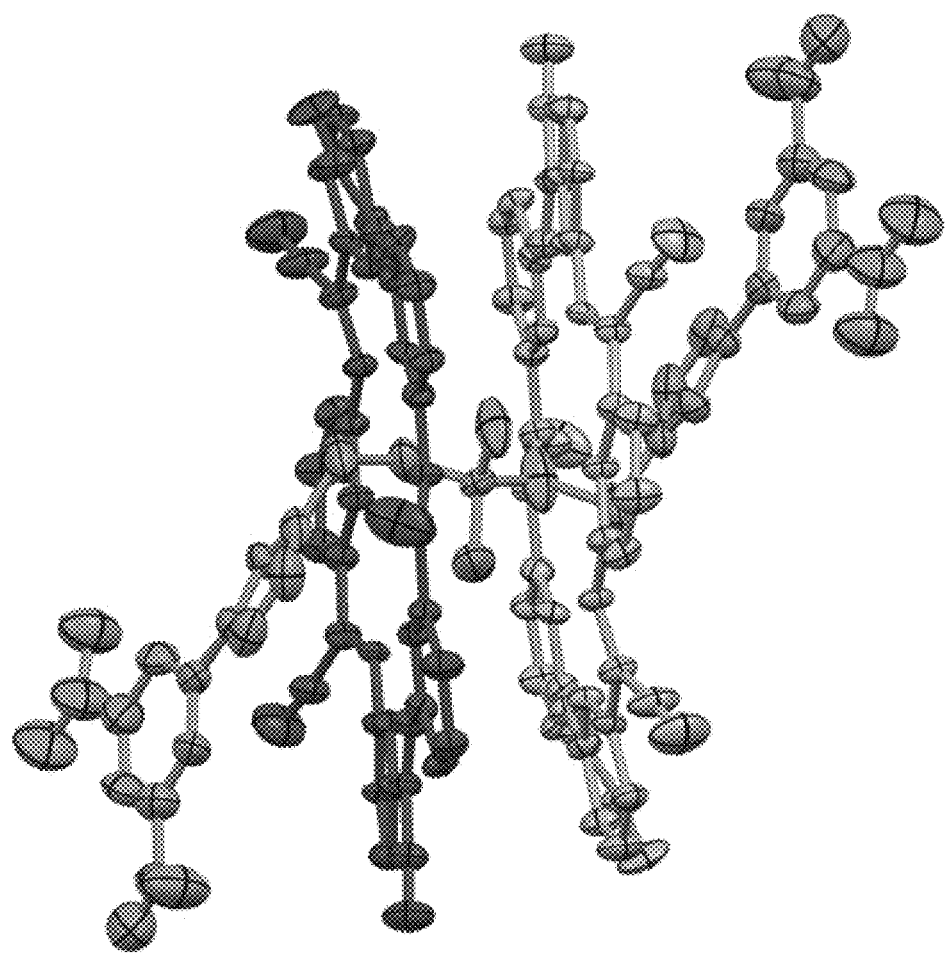
FIG. 4B illustrates the X-ray crystal structure of $3^-.TBA+$, (solvent molecules, $TBA^+$, t-Bu groups and protons are removed for clarity). The M-P isomer is shown.
Figure 4C:
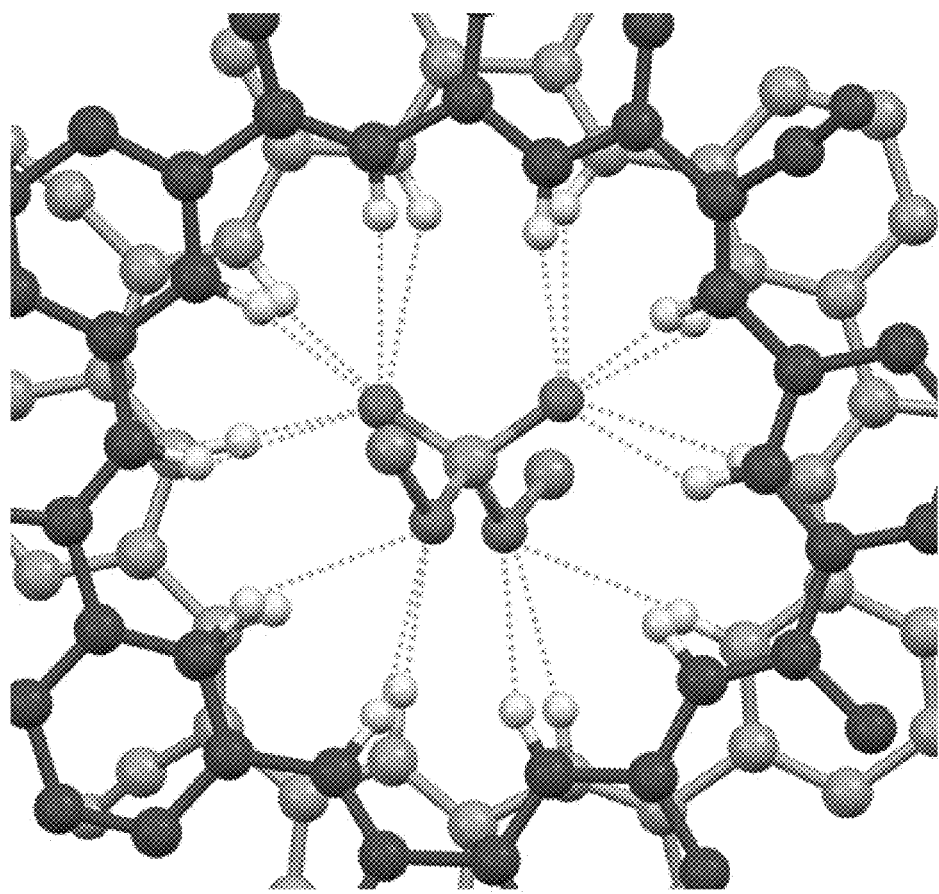
FIG. 4C illustrates CH . . . O hydrogen bonds (d≤3 Å) between CS inner cavity protons and phosphate oxygen atoms.

With the propensity for CS to capture large anions as 2:1 sandwich complexes, we wondered if it would be possible to prepare [3]rotaxanes that rely upon a dialkyl substituted phosphate, —R—$PO_4^-$—R—, as the central template in a manner reminiscent of Stoddart's dialkylammonium rotaxanes. Dipropargylphosphate was employed together with two equivalents of CS for formation of a putative [3]pseudorotaxane. Stoppering with a bulky azide-substituted 3,5-dimethylbenzoate using click chemistry (FIG. 4A) produced the desired [3]rotaxane, $2^-.TBA^+$, and after hydrolysis of the methyl ester, the tetracarboxylic acid, $3^-.TBA^+$. Single crystal X-ray diffraction data of $3^-.TBA^+$ shows a ring-in-rod structure that confirms formation of a [3]rotaxane (FIG. 4B). Akin to the empty CS, the macrocycles are disordered between M and P stereoisomers and the encapsulated phosphate also shows disorder. Short CH . . . O(phosphate) H-bonds, <3 Å, are evident and consistent with other phosphate complexes (FIG. 4C).

Numerous interlocked features were found to be consistent with the interlocked character. First, competition with the high-affinity $PF_6^-$ anion for the CS shows rotaxanes $2^+$ and $3^+$ to be robust to slippage at room temperature. Second, when $2^-$ was prepared as the sodium salt, ion exchange with the lipophilic $TBA^+$ ion was facile on account of the buried phosphate, whereas the hardness of the oxyanion in the corresponding dipropargylphosphate thread was more resistant to the exchange. Third, the phosphate inside rotaxane $3^-$ could not be protonated under conditions viable for the dipropargylphosphate (up to 1 M HCl), consistent with its protection. Fourth, all the regions of the NMR spectrum for rotaxane $2^-$ show the correct ratio of peak intensities corresponding to two macrocycles, a dumbbell and one cation. Fifth, cross peaks observed in the NOESY plots of $3^-$ (Supplementary Information, $d_6$-DMSO, 400 MHz, 298 K), between hydrogens on the macrocycle ($H^a$ and $H^d$) and from the dumbbell ($H^i$ and $H^h$) were observed.

We found that the meso and chiral stereoisomers suggested from the VT NMR study on the sandwich around $ClO_4^-$ could be covalently captured in the interlocked format of a [3]rotaxane. Consistently, the $^1H$ NMR spectrum of [3]rotaxane $3^-.TBA^+$ ($d_6$-DMSO) shows a major and minor component with a ~7:2 integration ratio similar to the $ClO_4^-$ sandwich complex, ~8:2. For example, see the major and minor peaks from the t-butyl peaks ($H^e$ and $H^{e*}$), the dumbbell ($H^h$ and $H^{h*}$) and the CS macrocycles ($H^c$ and $H^{c*}$). The isomers are configurationally stable based on heating $3^-.TBA^+$ to 393 K. Further confirmation that the signals for the two diastereomers originate from different spin systems are provided from unique cross peaks in the through-bond COSY and TOCSY spectra (see Supplementary Information).

The major and minor isomers were assigned to the meso and chiral compounds, respectively, based on the positions of the resonances assigned to the outer aromatic hydrogens of the macrocycles, $H^b$ and $H^c$. These signals show the largest differences between diastereotopic positions and allow us to distinguish their very different chemical environments. Briefly, the crystal structure of the meso compound (M-P) shows $H^b$ located deeper within the phenylene ring current of the neighboring p-stacked macrocycle than for the chiral compound (M-M and P-P). Correspondingly, $H^b$(meso) is located (see Supplementary Information) upfield of $H^{b*}$(chiral). Analysis of $H^c$(meso) and $H^{c*}$(chiral) is perfectly consistent with this assignment.

Example 18

Figure 5A:
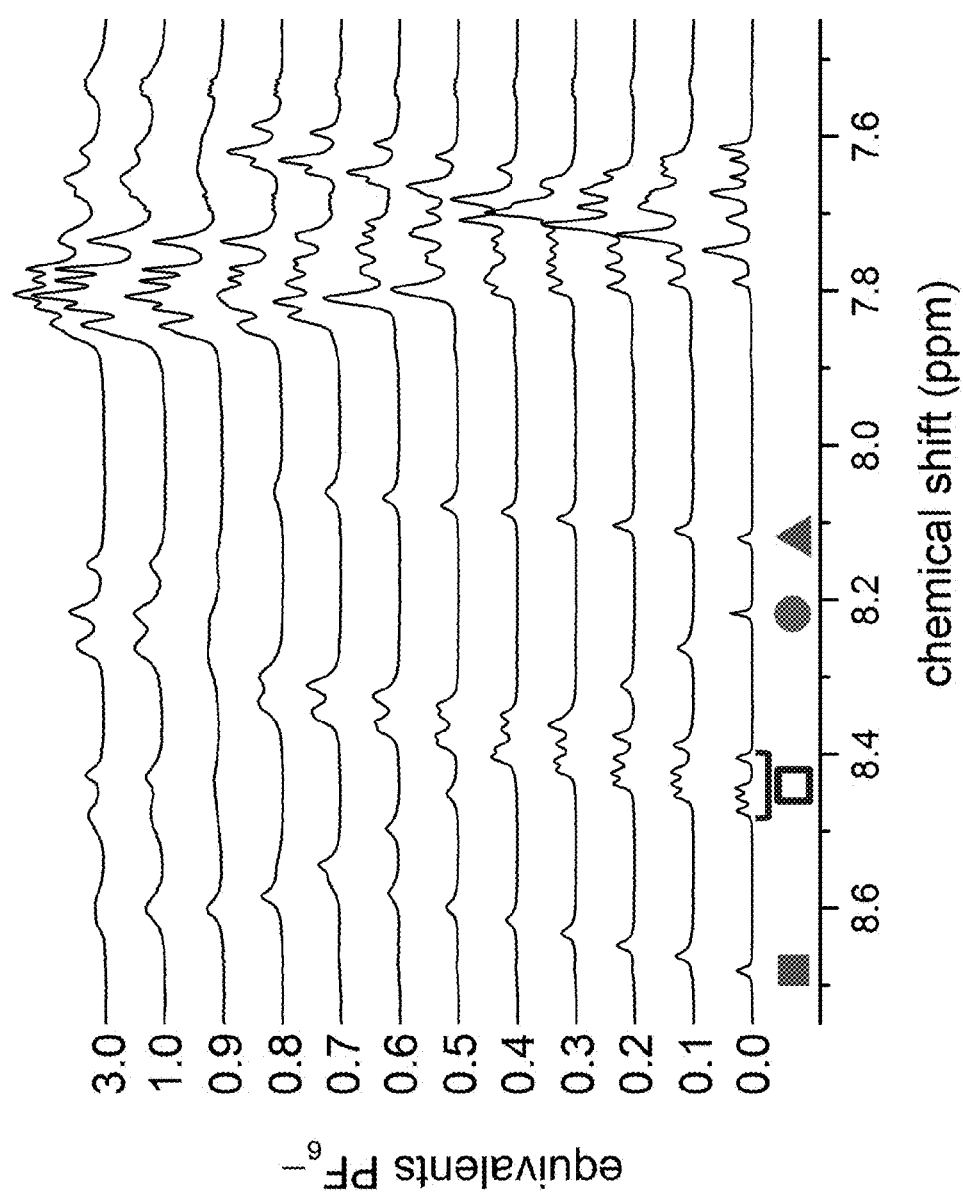
FIG. 5A illustrates partial $^1H$ NMR titration of a dodecylene-bridged bis-cyanostar (1 mM, $CD_2Cl_2$) with increasing equivalents of added $TBAPF_6$. The portions of the NMR spectra showing spectral changes in the dodecylene-bridged bis-cyanostar upon addition of $TBAPF_6$ are depicted by the symbols (black and blue squares, blue triangles, and red circles).
Figure 5B:
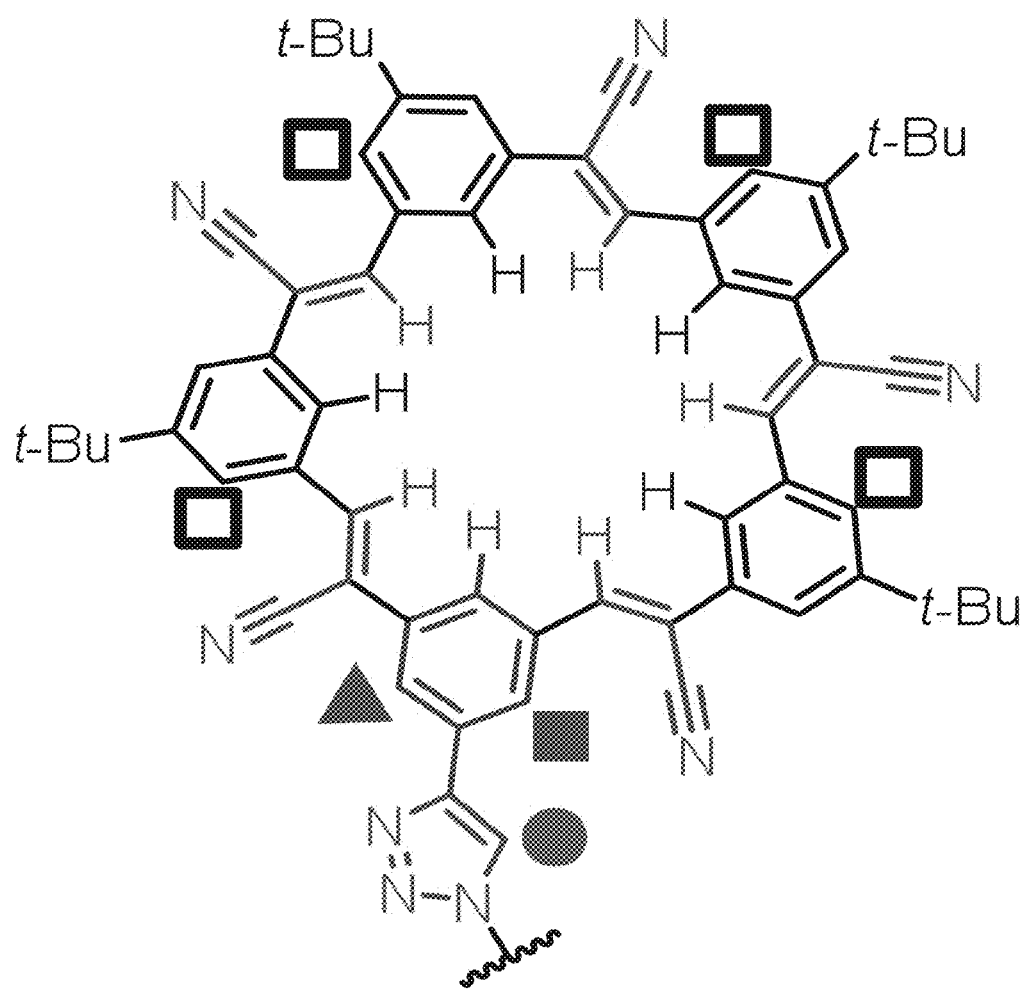
FIG. 5B illustrates the dodecylene-bridged bis-cyanostar structure, wherein the proton sites demonstrating titration-like changes in FIG. 5A are illustrated by the symbols (empty black squares and solid blue squares, blue triangles, and red circles).
Figure 5C:
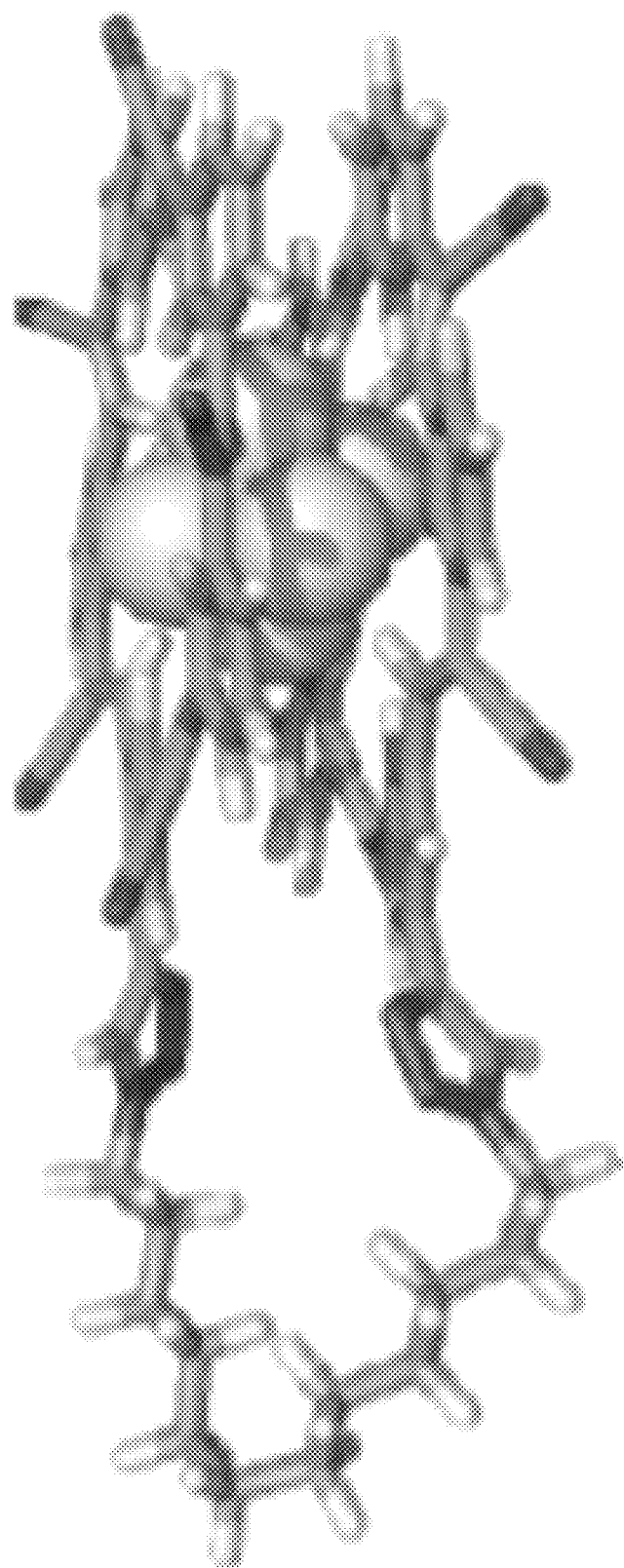
FIG. 5C depicts molecular modeling (MMFF) of a self-complex bismacrocycle having formula (IV-CS-12D) (dodecylene-bridged bis-cyanostar) with $PF_6^-$ supporting a m/z signal of 2164.09 Daltons by ESI-MS.

NMR Titration Data and ESI-MS Evidence of 1:1 Stoichiometry for Bismacrocycle (IV-CS-12D)-Anion Complexes A titration was performed with dodecylene-bridged biscyanostar (IV-CS-12D) with $TBAPF_6$ in the presence of $CD_2Cl_2$ (1 mM) to observe structural changes upon addition of $TBAPF_6$. As increasing amounts of $TBAPF_6$ were added, a gradual upfield shift of the extracavity protons of the cyanostar was observed (black and blue squares, FIGS. 5A and 5B) consistent with sandwich formation. After 1 equivalent of anion had been added, little change in the spectrum was observed consistent with 1:1 stoichiometry (FIG. 5A). Insight into the species present at the final titration point (3.0 eq. $PF_6$) using electrospray ionization mass spectrometry showed only one signal matching the 1:1 $PF_6^-$ self-complex (FIG. 5C) consistent with the clam-shell capture of the anion (m/z signal of 2164.09 Daltons).

Incorporation by Reference

All patents, patent applications and non-patent publications cited herein are incorporated by reference in their entirety.

REFERENCES

1 Pedersen, C. J. Cyclic polyethers and their complexes with metal salts. *J. Am. Chem. Soc.* 89, 2495-2496 (1967)

2 Valeur, B. & Leray, I. Design principles of fluorescent molecular sensors for cation recognition. *Coord. Chem. Rev.* 205, 3-40 (2000).

3 Cram, D. J. & Sogah, G. D. Y. Chiral crown complexes catalyse Michael addition reactions to give adducts in high optical yields. *J. Chem. Soc. Chem. Commun.* 625-628 (1981).

4 Ma, D. et al. Acyclic cucurbit[n]uril molecular containers enhance the solubility and bioactivity of poorly soluble pharmaceuticals. *Nat. Chem.* 4, 503-510 (2012).

5 Stoddart, J. F. The chemistry of the mechanical bond. *Chem. Soc. Rev.* 38, 1802-1820 (2009)

6 Kay, E. R., Leigh, D. A. & Zerbetto, F. Synthetic molecular motors and mechanical machines. *Angew. Chem. Int. Ed.* 46, 72-191 (2007).

7 Höger, S. Shape-persistent phenylene-acetylene macrocycles: Large rings-low yield?*Angew. Chem. Int. Ed.* 44, 3806-3808 (2005)

8 Busch, D. H. The significance of complexes of macrocyclic ligands and their synthesis by ligand reactions. *Rec. Chem. Progr.* 25, 107-126 (1964)

9 Ogoshi, T., Kanai, S., Fujinami, S., Yamagishi, T.-a. & Nakamoto, Y. para-Bridged symmetrical pillar[5]arenes: Their Lewis acid catalyzed synthesis and host-guest property. *J. Am. Chem. Soc.* 130, 5022-5023 (2008)

10 Yuan, L. H. et al. Highly efficient, one-step macrocyclizations assisted by the folding and preorganization of precursor oligomers. *J. Am. Chem. Soc.* 126, 11120-11121 (2004).

11 Zhang, W. & Moore, J. S. Arylene ethynylene macrocycles prepared by precipitation-driven alkyne metathesis. *J. Am. Chem. Soc.*, 126, 12796 (2004)

12 Qin, B. et al. Crystallographic evidence of an unusual, pentagon-shaped folding pattern in a circular aromatic pentamer. *Org. Lett.* 10, 5127-5130 (2008).

13 Guieu, S., Crane, A. K. & MacLachlan, M. J. Campestarenes: Novel shape-persistent Schiff base macrocycles. *Chem. Commun.* 47, 1169-1171 (2011)

14 Zhang, J., Pesak, D. J., Ludwick, J. L. & Moore, J. S. Geometrically-controlled and site-specifically-functionalized phenylacetylene macrocycles. *J. Am. Chem. Soc.* 116, 4227-4239 (1994).

15 Du, Z. et al. BOP-mediated one-pot synthesis of $C_5$-symmetric macrocyclic pyridone pentamers. *Chem. Commun.* 47, 12488-12490 (2011).

16 Qin, B. et al. Persistently folded circular aromatic amide pentamers containing modularly tunable cation-binding cavities with high ion selectivity. *J. Am. Chem. Soc.* 132, 9564-9566 (2010).

17 Ren, C. et al. Crystallographic realization of the mathematically predicted densest all-pentagon packing lattice by $C_5$-symmetric "sticky" fluoropentamers. *Angew. Chem. Int. Ed.* 50, 10612-10615 (2011).

18 Ren, C., Xu, S., Xu, J., Chen, H. & Zeng, H. Planar macrocyclic fluoropentamers as supramolecular organogelators. *Org. Lett.* 13, 3840-3843 (2011)

19 Tahara, K., Balandina, T., Furukawa, S., De Feyter, S. & Tobe, Y. Molecular pentagonal tiling: Self-assemblies of pentagonal-shaped macrocycles at liquid/solid interfaces. *CrystEngComm.* 13, 5551-5558 (2011)

20 Hua, Y. & Flood, A. H. Click chemistry generates privileged CH hydrogen-bonding triazoles: The latest addition to anion supramolecular chemistry. *Chem. Soc. Rev.* 39, 1262-1271 (2010)

21 Bryantsev, V. S. & Hay, B. P. Are C—H groups significant hydrogen bonding sites in anion receptors? Benzene complexes with Cl$^-$, NO$_3^-$, and ClO$_4^-$. *J. Am. Chem. Soc.* 127, 8282-8283 (2005)

22 Li, Y. & Flood, A. H., Pure C—H hydrogen bonding to chloride ions: A preorganized and rigid macrocyclic receptor. *Angew. Chem. Int. Ed.* 47, 2649-2652 (2008)

23 Sessler, J. L. et al. A pyrrolyl-based triazolophane: A macrocyclic receptor with CH and NH donor groups that exhibits a preference for pyrophosphate anions. *J. Am. Chem. Soc.* 132, 14058-14060(2010).

24 Tinant, B. et al. Structural study of stilbenes. 2. Crystal-structure redetermination of trans 4'-dimethylamino-4-nitro-a-cyanostilbene $C_{17}H_{15}N_3O_2$. *Bull. Soc. Chim. Belg.* 92, 403-404 (1983)

25 Yu, G. & Heeger, A. J. Charge separation and photovoltaic conversion in polymer composites with internal donor-acceptor heterojunctions. *J. App. Phys.* 78, 4510-4515 (1995).

26 An, B.-K., Kwon, S.-K., Jung, S.-D. & Park, S. Y. Enhanced emission and its switching in fluorescent organic nanoparticles. *J. Am. Chem. Soc.* 124, 14410-14415 (2002)

27 Brak, K. & Jacobsen, E. N. Asymmetric ion-pairing catalysis. *Angew. Chem. Int. Ed.* 52, 534-561 (2013).

28 Greer, M. A., Goodman, G., Pleus, R. C. & Greer, S. E. Health effects assessment for environmental perchlorate contamination: The dose response for inhibition of thyroidal radioiodine uptake in humans. *Environ. Health Persp.* 110, 927-937 (2002).

29 Etacheri, V., Marom, R., Elazari, R., Salitra, G. & Aurbach, D. Challenges in the development of advanced Li-ion batteries: a review. *Energy Environ. Sci.* 4, 3243-3262 (2011).

Rosenthal, M. R. The myth of the non-coordinating anion. *J. Chem. Educ.* 50, 331-335 (1973)

31 Hristova, Y. R., Smulders, M. M. J., Clegg, J. K., Breiner, B. & Nitschke, J. R. Selective anion binding by a "chameleon" capsule with a dynamically reconfigurable exterior. *Chem. Sci.* 2, 638-641 (2011).

32 Hayashida, O., Shivanyuk, A. & Rebek Jr., J. Molecular encapsulation of anions in a neutral receptor. *Angew. Chem. Int. Ed.* 41, 3423-3426 (2002).

33 Hübner, G. M., Glaser, J., Seel, C. & Vögtle, F. High-yielding rotaxane synthesis with an anion template. *Angew. Chem. Int. Ed.* 38, 383-386 (1999).

34 Keaveney, C. M. & Leigh, D. A. Shuttling through anion recognition. *Angew. Chem. Int. Ed.* 43, 1222-1224 (2004)

35 Brouwer, A. M. et al. Photoinduction of fast, reversible translational motion in a hydrogen-bonded molecular shuttle. *Science* 291, 2124-2128 (2001).

36 Ghosh, P., Mermagen, O. & Schalley, C. A. Novel template effect for the preparation of rotaxanes with functionalized centre pieces. *Chem. Commun.* 2628-2629 (2002)

37 Lee, C. F. et al. Hybrid organic-inorganic rotaxanes and molecular shuttles. *Nature* 458, 314-318 (2009).

38 Wisner, J. A., Beer, P. D., Drew, M. G. B. & Sambrook, M. R. Anion-templated rotaxane formation. *J. Am. Chem. Soc.* 124, 12469-12476 (2002)

39 Yuan, L. et al. Highly efficient, one-step macrocyclizations assisted by the folding and preorganization of precursor oligomers. *J. Am. Chem. Soc.* 126, 11120-11121 (2004).

40 Alcalde, E., Ayala, C., Dinarès, I. & Mesquida, N. Polynucleating open-chain systems with imidazole and proton-ionizable 1,2,4-triazole structural motifs. *J. Org. Chem.* 66, 2291-2295 (2001).

41 Bandera, D., Baldridge, K. K., Linden, A., Dorta, R. & Siegel, J. S. Stereoselective coordination of $C_5$-symmetric corannulene derivatives with an enantiomerically pure [Rh$^J$(nbd*)] metal complex. *Angew. Chem. Int. Ed.* 50, 865-867 (2011).

42 Hanson, J. C. & Nordman, C. E. The crystal and molecular structure of corannulene, $C_{20}H_{10}$. *Acta Cryst. B* 32, 1147-1153 (1976).

43 Li, Y., Pink, M., Karty, J. A. & Flood, A. H. Dipole-promoted and size-dependent cooperativity between pyridyl-containing triazolophanes and halides leads to persistent sandwich complexes with iodide. *J. Am. Chem. Soc.* 130, 17293-17295 (2008).

44 Szumna, A. Inherently chiral concave molecules—from synthesis to applications. *Chem. Soc. Rev.* 39, 4274-4285 (2010).

45 Roobottom, H. K., Jenkins, H. D. B., Passmore, J. & Glasser, L. Thermochemical radii of complex ions. *J. Chem. Educ.* 76, 1570-1573 (1999).

46 Vander Griend, D. A., Bediako, D. K., DeVries, M. J., DeJong, N. A. & Heeringa, L. P. Detailed spectroscopic, thermodynamic, and kinetic characterization of nickel(II) complexes with 2,2'-bipyridine and 1,10-phenanthroline attained via equilibrium-restricted factor analysis. *Inorg. Chem.* 47, 656-662 (2007).

47 Ashton, P. R. et al. Self-assembling [2]- and [3]rotaxanes from secondary dialkylammonium salts and crown ethers. *Chem. Eur. J.* 2, 729-736 (1996).

48 Katayev, E. A., Ustynyuk, Y. A. & Sessler, J. L. Receptors for tetrahedral oxyanions. *Coord. Chem. Rev.* 250, 3004-3037 (2006).

49 Craig, M. R., Claridge, T. D. W., Hutchings, M. G. & Anderson, H. L. Synthesis of a cyclodextrin azo dye [3]rotaxane as a single isomer. *Chem. Commuin.* 1537-1538 (1999)

50 Talotta, C., Gaeta, C., Pierro, T. & Neri, P. Sequence stereoisomerism in calixarene-based pseudo[3]rotaxanes. *Org. Lett.* 13, 2098-2101 (2011)

51. Shen, Q.; Zhang, J.; Zhang, S.; Hao, Y.; Zhang, W.; Zhang, W.; Chen, G.; Zhang, Z.; Zhu, X. Facile one-pot/one-step technique for preparation of side-chain functionalized polymers: Combination of SET-RAFT polymerization of azide vinyl monomer and click chemistry. *J. Polym. Sci., Part A: Polym. Chem.* 2012, 50, 1120-1126.

52. Benson, C R.; Fatila, E. M; Lee, S.; Marzo, M. G.; Pink, M.; Mills, M. B.; Preuss, K. E.; Flood, A. H., "Extreme Stabilization and Redox Switching of Organic Anions and Radical Anions by Large-cavity, CH Hydrogen-Bonding Cyanostar Macrocycles," *J. Am. Chem. Soc.* 2016, 138, 15057-15065.

What is claimed is:

1. A complex comprising:
(a) an anion and
(b) a poly-cyanostilbene macrocycle of Formula (I):

Formula (I)

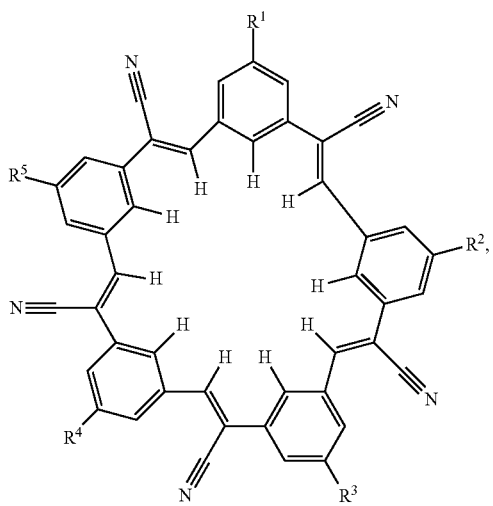

(CS)

wherein $R^1$, $R^2$, $R^3$, $R^4$, and $R^5$ are selected from the group consisting of alkenyl, alkyl, alkoxy, alkyl-NH-alkyl, aryl, cycloalkyl, heteroaryl, heterocycle, haloalkyl, hydrogen, iodo, —$OR^6$, —$N(R^7R^8)$, —$CO_2R^9$, —C(O)—$N(R^{10}R^{11})$, wherein $R^6$, $R^7$, $R^8$, $R^9$, $R^{10}$, and $R^{11}$ are selected from the group consisting of alkenyl, alkyl, alkoxy, alkyl-NH-alkyl, aryl, arylalkyl, cycloalkyl, heteroaryl, heterocycle, haloalkyl, and hydrogen, wherein the anion is selected from $BF_4^-$, $ClO_4^-$, $PF_6^-$, $N(SO_2CF_3)_2^-$, $N(SO_2C_2F_5)_2^-$, $CH_3SO_3^-$, $CF_3SO_3^-$, $AsO_4^{3-}$, $AsF_6^-$, $AlCl_4^-$, $PO_4^{3-}$, $HPO_4^{2-}$, $H_2PO_4^-$, $SO_4^{2-}$, $HSO_4^-$, $B(CN)_4^-$, $Cl^-$, $Br^-$, $I^-$, cyanide, $BrO_4^-$, $IO_4^-$, $F^-$, $HF_2^-$, $TcO_4^-$, $RPO_4^{2-}R_2PO_4^-$, $RSO_3^-$, $SCN^-$, $N_3^-$, $I_3^-$, $CO_3^{2-}HCO_3^-$, $FeCl_4^-$, $PtCl_6^{2-}$, $S_n^{x-}$ where n=1-8, and x=1 or 2, $P_2O_7^{4-}$, $HP_2O_7^{3-}$, $H_2P_2O_7^{2-}$ $H_3P_2O_7^-$, a polyphosphate polyanion, a tetrazine anion, a dithiadiazolide anion, $RBF_3^-$, Ar—$O^-$, wherein R comprises a substituent.

2. The complex of claim 1, wherein $R^1$, $R^2$, $R^3$, $R^4$, and $R^5$ comprise identical substituents.

3. The complex of claim 1, wherein $R^1$, $R^2$, $R^3$, $R^4$, and $R^5$ comprise tert-butyl groups.

4. The complex of claim 1, wherein the poly-cyanostilbene macrocycle having Formula (I) is selected from the following:

(I-1)

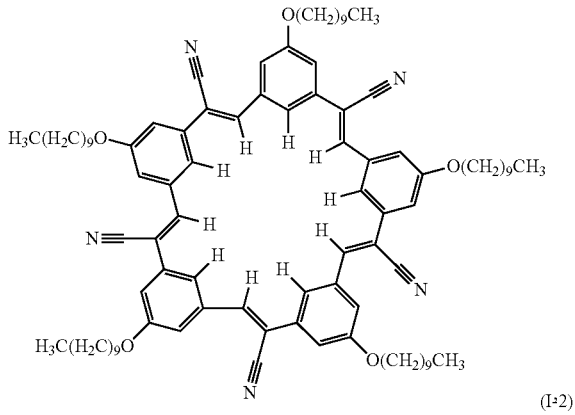

(I-2)

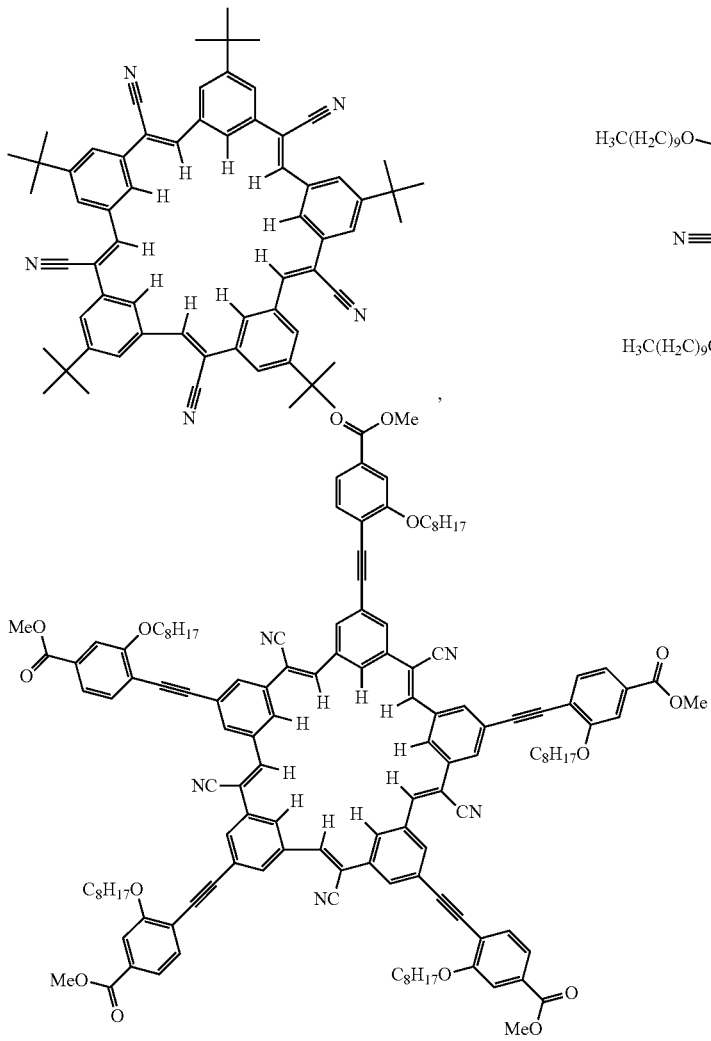

(I-3)
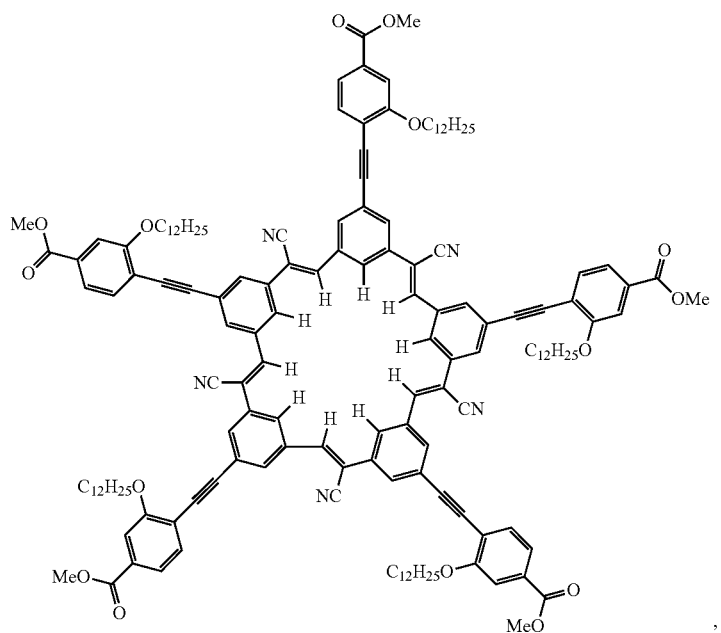
(I-4)
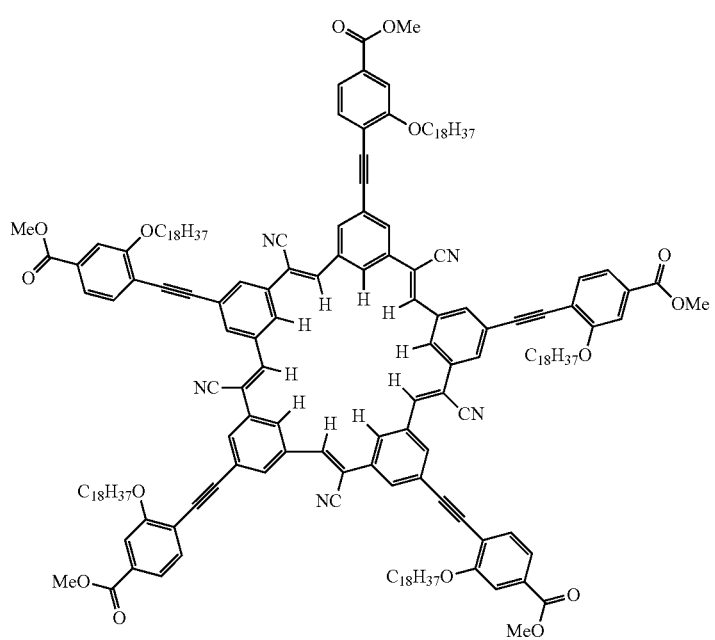

-continued
(I-5)
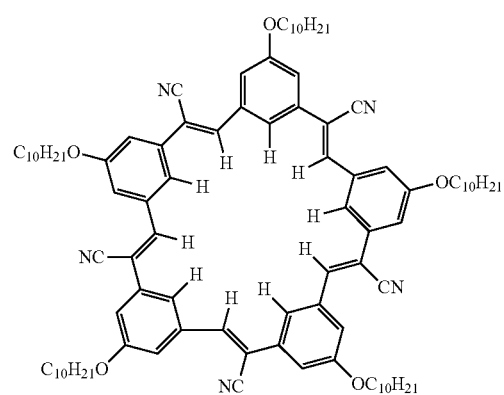
(I-6)
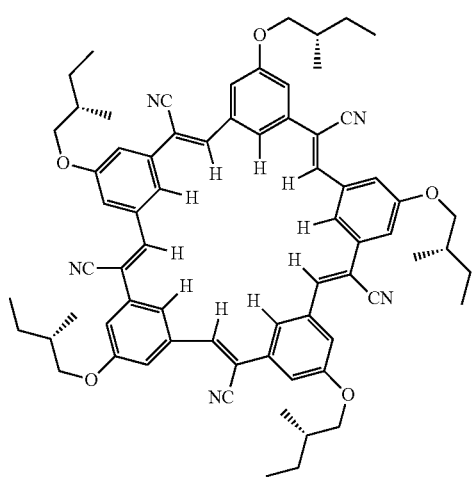
(I-7)
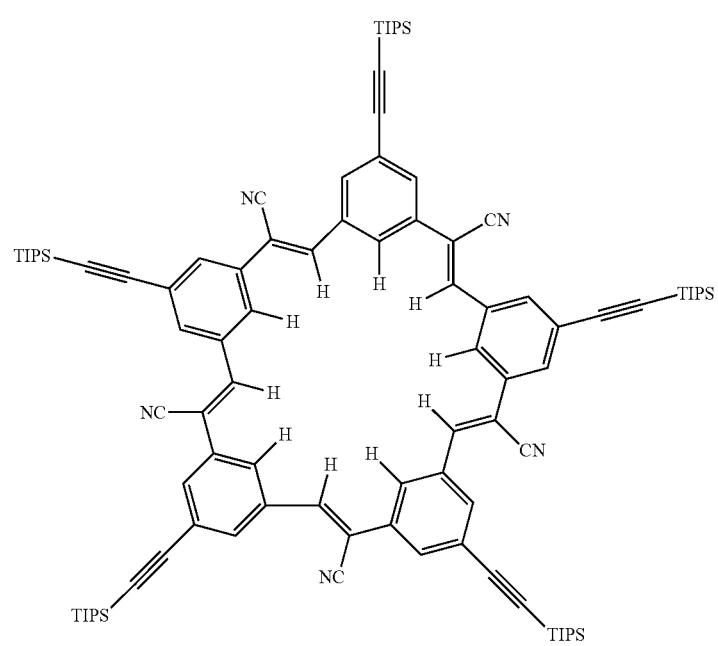

-continued
(I-8)
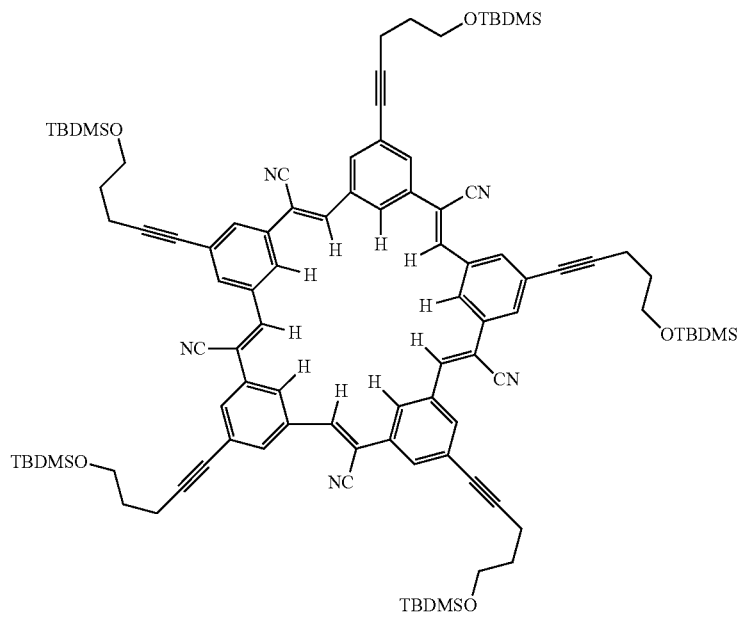
,
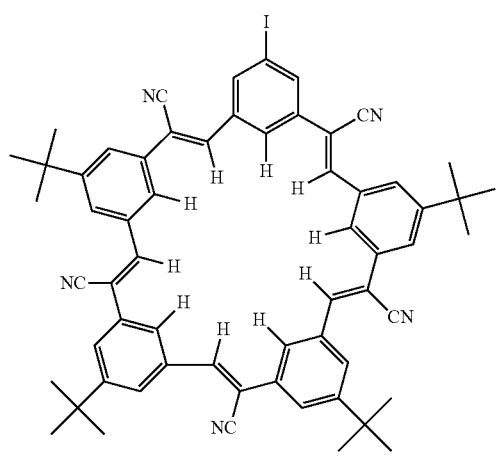
(CS-I)
,
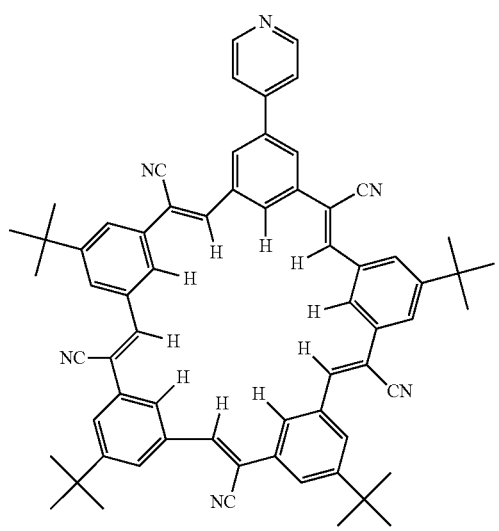
(CS-Py)
,

81
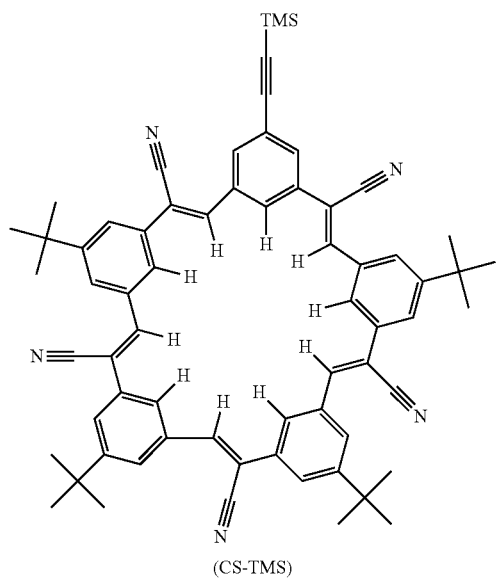
(CS-TMS)
82
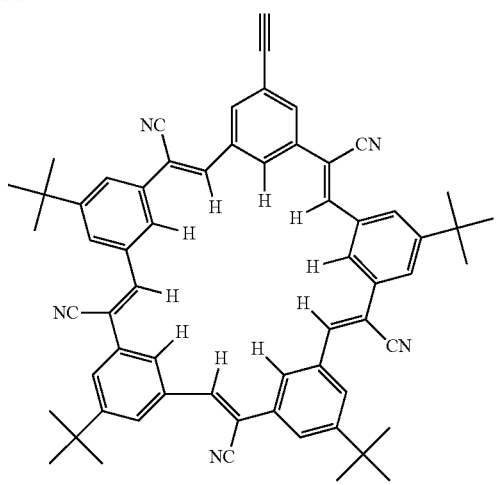
(Cs-Ac)
and
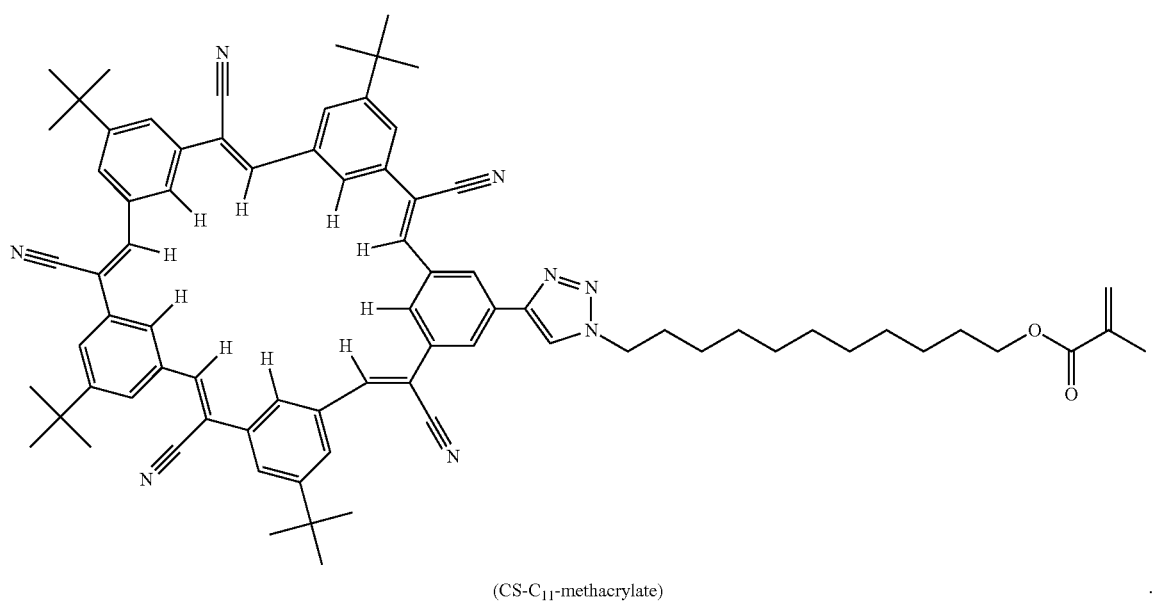
(CS-C$_{11}$-methacrylate)

5. A complex comprising:
(a) an anion and
(b) a poly-cyanostilbene macrocycle of Formula (IV):

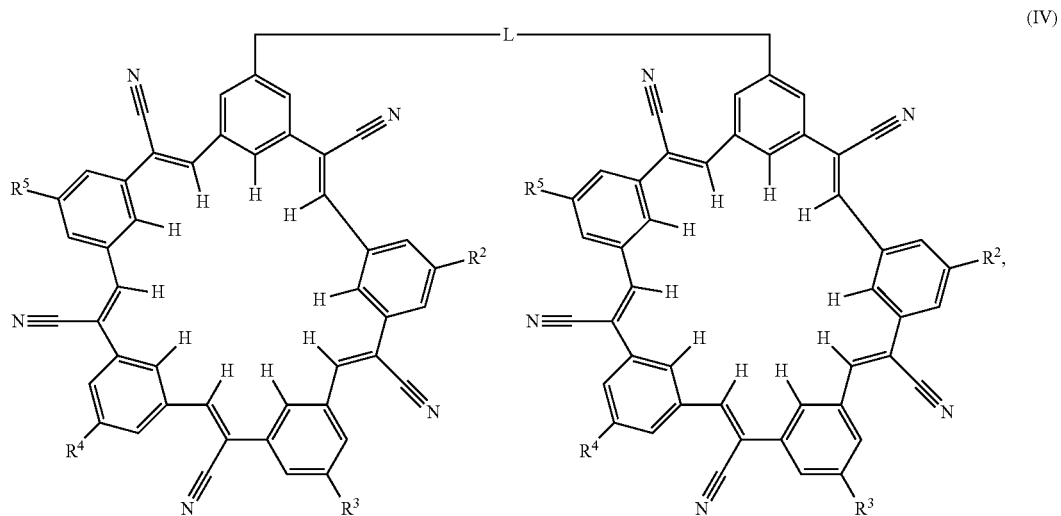

wherein $R^2$, $R^3$, $R^4$, and $R^5$ are selected from the group consisting of alkenyl, alkyl, alkoxy, alkyl-NH-alkyl, aryl, cycloalkyl, heteroaryl, heterocycle, haloalkyl, hydrogen, iodo, —$OR^6$, —$N(R^7R^8)$, —$CO_2R^9$, —C(O)—$N(R^{10}R^{11})$, wherein $R^6$, $R^7$, $R^8$, $R^9$, $R^{10}$, and $R^{11}$ are selected from the group consisting of alkenyl, alkyl, alkoxy, alkyl-NH-alkyl, aryl, arylalkyl, cycloalkyl, heteroaryl, heterocycle, haloalkyl, and hydrogen, and L comprising an alkyl moiety ranging from $C_{1-30}$, said alkyl moiety comprising a saturated or unsaturated alkyl moiety, and optionally comprises substituents, wherein the anion is selected from $BF_4^-$, $ClO_4^-$, $PF_6^-$, $N(SO_2CF_3)_2^-$, $N(SO_2C_2F_5)_2^-$, $CH_3SO_3^-$, $CF_3SO_3^{31}$, $AsO_4^{3-}$, $AsF_6^-$, $AlCl_4^-$, $PO_4^{3-}$, $HPO_4^{2-}$, $H_2PO_4^-$, $SO_4^{2-}$, $HSO_3^-$, $B(CN)_4^-$, $Cl^-$, $Br^-$, $I^-$, cyanide, $BrO_4^{31}$, $IO_4^-$, $F^-$, $HF_2^-$, $TcO_4^-$, $RPO_4^{2-}$, $R_2PO_4^-$, $RSO_3^-$, $SCN^-$, $N_3^-$, $I_3^-$, $CO_3^{2-}$, $HCO_3^-$, $FeCl_4^-$, $PtCl_6^{2-}$, $S_n^{x-}$ where n=1-8, and x=1 or 2, $P_2O_7^{4-}$, $HP_2O_7^{3-}$, $H_2P_2O_7^{2-}$, $H_3P_2O_7^-$, a polyphosphate polyanion, a tetrazine anion, a dithiadiazolide anion, $RBF_3^-$, Ar—$O^-$, wherein R comprises a substituent.

6. The complex of claim 5, wherein $R^2$, $R^3$, $R^4$, and $R^5$ comprise identical substituents.

7. The complex of claim 5, wherein $R^2$, $R^3$, $R^4$, and $R^5$ comprise tert-butyl groups.

8. The complex of claim 5, wherein the poly-cyanostilbene macrocycle of Formula (IV) comprises:

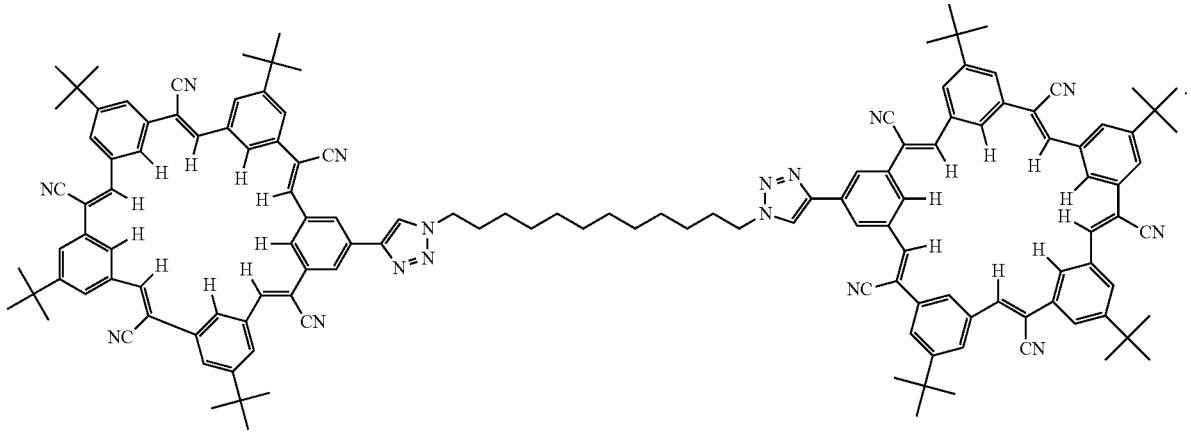

(IV-CS-12D)

* * * * *